US010287592B2

(12) United States Patent
Van Rij et al.

(10) Patent No.: US 10,287,592 B2
(45) Date of Patent: May 14, 2019

(54) *BACILLUS* HOST

(71) Applicant: DSM IP Assets B.V., Heerlen (NL)

(72) Inventors: Evert Tjeerd Van Rij, Echt (NL); Martine Spaans, Echt (NL); Hendrikus Bernardus Carolus Hillebrand, Echt (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 15/116,933

(22) PCT Filed: Feb. 6, 2015

(86) PCT No.: PCT/EP2015/052552
§ 371 (c)(1),
(2) Date: Aug. 5, 2016

(87) PCT Pub. No.: WO2015/118126
PCT Pub. Date: Aug. 13, 2015

(65) Prior Publication Data
US 2017/0175130 A1    Jun. 22, 2017

(30) Foreign Application Priority Data
Feb. 7, 2014   (EP) .................................. 14154317

(51) Int. Cl.
*C12N 15/63* (2006.01)
*C12N 15/75* (2006.01)
(Continued)

(52) U.S. Cl.
CPC ............ *C12N 15/75* (2013.01); *C12N 9/2411* (2013.01); *C12N 9/2482* (2013.01); *C12N 9/54* (2013.01);
(Continued)

(58) Field of Classification Search
CPC ....................................................... C12N 15/63
See application file for complete search history.

(56) References Cited

U.S. PATENT DOCUMENTS 8,426,182 B1    4/2013  Parenicova
8,551,732 B2   10/2013  Lehmann et al.
(Continued)

FOREIGN PATENT DOCUMENTS

EP    0501765 A1    9/1992
EP    1391502 A1    2/2004
(Continued)

OTHER PUBLICATIONS

Perkins et al., "Genetic engineering of Bacillus subtilis for the commercial production of riboflavin," J Industrial Microbiol & Biotechnol 22:8-18, 1999.*
(Continued)

*Primary Examiner* — Rosanne Kosson
(74) *Attorney, Agent, or Firm* — McBee Moore Woodward & Vanik IP, LLC; Susan McBee; Chester Moore

(57) ABSTRACT

The invention provides *Bacillus* host cell deficient in the production of a neutral protease and of a alkaline protease which host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence. Said host cell can advantageously be used in a method of production of a compound of interest.

20 Claims, 9 Drawing Sheets
Specification includes a Sequence Listing.

(51) Int. Cl.
C12N 9/54 (2006.01)
C12P 21/02 (2006.01)
C12N 9/26 (2006.01)
C12N 9/24 (2006.01)
C12P 21/00 (2006.01)

(52) U.S. Cl.
CPC .............. *C12P 21/00* (2013.01); *C12P 21/02* (2013.01); *C12Y 302/01008* (2013.01); *C12Y 302/01133* (2013.01); *C12Y 304/21062* (2013.01); *C12Y 304/24028* (2013.01)

(56) References Cited

U.S. PATENT DOCUMENTS

2003/0186380 A1* 10/2003 Thomas ......... C12Y 305/01001
　　　　　　　　　　　　　　　　　　　　　　　　435/69.1
2010/0173353 A1　7/2010 Lehmann et al.

FOREIGN PATENT DOCUMENTS

| EP | 2186880 A1 * | 5/2010 | ............ C07K 14/32 |
| WO | 2008101857 A2 | 8/2008 | |
| WO | 2008148575 A2 | 12/2008 | |

OTHER PUBLICATIONS

Lee et al., "Conserved nucleotide sequences in temporally controlled bacteriophage promoters," J Mol Biol 152:247-265, 1981.*
Yansura and D.J. Hener D.G.; "Use of the *Escherichia coli* lac repressor and operator to control gene expression in Bacillus subtilis"; Proceedings of the National Academy of Sciences, National Academy of Sciences, US; vol. 81, Jan. 1, 1984; pp. 439-443, XP002131397.
Marcia S. Osburne et al.; " Short Communication Activity of Two Strong Promoters Cloned into Bacillus Subtilis"; Journal of General Microbiology; Jan. 1, 1986; pp. 565-568, XP055183272.
Kawamura F. et al.; "Construction of a Bacillus Subtilis Double Mutant Deficient in Extracellular Alkaline and Neutral Proteases"; Journal of Bacteriology, American Society for Microbiology, Washington DC, US; vol. 160, No. 1; Oct. 1, 1984; pp. 442-444; XP002999435.
Stewart C.R. et al.; "The Genome of Bacillus Subtilis Bacteriophage SP01"; Journal of Molecular Biology, Academic Press, UK; vol. 388, No. 1; Apr. 24, 2009; pp. 48-70; XP026066960.
Wang P-Z et al.; "Overlapping Promoters Transcribed by Bacillus Subtilis Sigma 55 and Sigma 37 RNA Polymerase Holoenzymes during Growth and Stationary Phases"; Journal of Biological Chemistry (microfilms); American Society of Biological Chemists, Baltimore, MD, US; vol. 259; No. 13; Jul. 10, 1984; pp. 8619-8625; XP002042749.

* cited by examiner

BACILLUS HOST

CROSS REFERENCE TO RELATED APPLICATIONS

This application is a § 371 National Stage Application of PCT/EP2015/052552, filed Feb. 6, 2015, which claims priority to EP14154317.3, filed Feb. 7, 2014.

FIELD OF THE INVENTION

The present invention relates to a novel *Bacillus* host cell, to a method for producing said host cell, to a method for producing a compound of interest using said host cell, to the use of said host cell in methods of producing a compound of interest.

BACKGROUND OF THE INVENTION

*Bacillus* strains produce and secrete a large number of useful proteins and metabolites. Because of their GRAS (General Recognised As Safe) status, *Bacillus* hosts, e.g. belonging to the species *Bacillus subtilis, Bacillus amyloliquefaciens* and *Bacillus licheniformis*, are largely used in the production of important proteins for the food, feed and pharmaceutical industry.

A common problem in the application of *Bacillus* hosts in the expression of heterologous or the overexpression of homologous proteins of interest is related to the presence in said host cells of genes coding for several extracellular proteases which are co-expressed together with the proteins of interest. For those heterologous proteins of interest which are sensitive to protease degradation, the co-expression of homologous proteases in *Bacillus* leads to loss of yield, while the homologous *Bacillus* proteins of interest are contaminated by said co-expressed *Bacillus* proteases leading to purification problems.

The major extracellular protease in *Bacillus* hosts are extracellular neutral proteases (also known as bacillolysin EC 3.4.24.28) and alkaline proteases (also known as subtilisin EC 3.4.21.62). The problem caused by extracellular proteases in the production of useful proteins by *Bacillus* strains can be solved by using a *Bacillus* strain which is deficient in said extracellular neutral and alkaline proteases (see for example Kawamura et al (Journal of Bacteriology, (1984) p. 442-444, which describes a mutant strain of *Bacillus subtilis* which is deficient in the structural genes for extracellular neutral (nprE) and alkaline (aprA) proteases).

Other genes present in *Bacillus* strains have been shown to decrease the productivity of proteins of interest in said production hosts. U.S. Pat. No. 7,585,674 discloses that the productivity of a protein or polypeptide of interest in host cells, e.g. *Bacillus* cells, can be improved by deleting from the genome of said host cell specific genes participating in sporulation stage II, III, IV or V.

However there still remains a need for methods to increase expression of proteins in *Bacillus* hosts.

SUMMARY OF THE INVENTION

It has been surprisingly found that a recombinant *Bacillus* host cell deficient in neutral and/or alkaline proteases, can be used in the production of a protein of interest with high yield when the gene of interest coding for the protein of interest is operably linked to a bacteriophage promoter, preferably a bacteriophage SPO1 promoter, allowing for expression of the protein of interest in the host cell.

Therefore the invention provides a recombinant *Bacillus* host cell deficient in the production of a neutral protease and/or of an alkaline protease which host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.

Throughout this specification with the term "neutral protease" it is intended an enzyme classified according to the Enzyme Commission number EC 3.4.24.28. Throughout this specification with the term "alkaline protease" it is intended an enzyme classified according to the Enzyme Commission number EC 3.4.21.62.

According to the invention there is also provided a method of producing a recombinant *Bacillus* host cell according to the invention comprising:
  a. providing a *Bacillus* host cell deficient in the production of a neutral protease and/or in the production of an alkaline protease, optionally deficient in the production of a neutral α-amylase, optionally deficient in a sporulation-related gene;
  b. transforming the *Bacillus* host cell with a nucleic acid construct comprising a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.

The invention further provides a method for the production of a compound of interest comprising
  a) culturing a recombinant *Bacillus* host cell according to the invention or a recombinant *Bacillus* host cell produced according to the method for the production of a recombinant host cell according to the invention, under conditions conducive to the production of the compound of interest, and
  b) optionally isolating the compound of interest from the culture broth.

The invention also provides with the use of the recombinant *Bacillus* host cell according to the invention or produced according to a method for producing a recombinant *Bacillus* host cell according to the invention in the production of a compound of interest.

DESCRIPTION OF THE SEQUENCE LISTING

Figure 1:
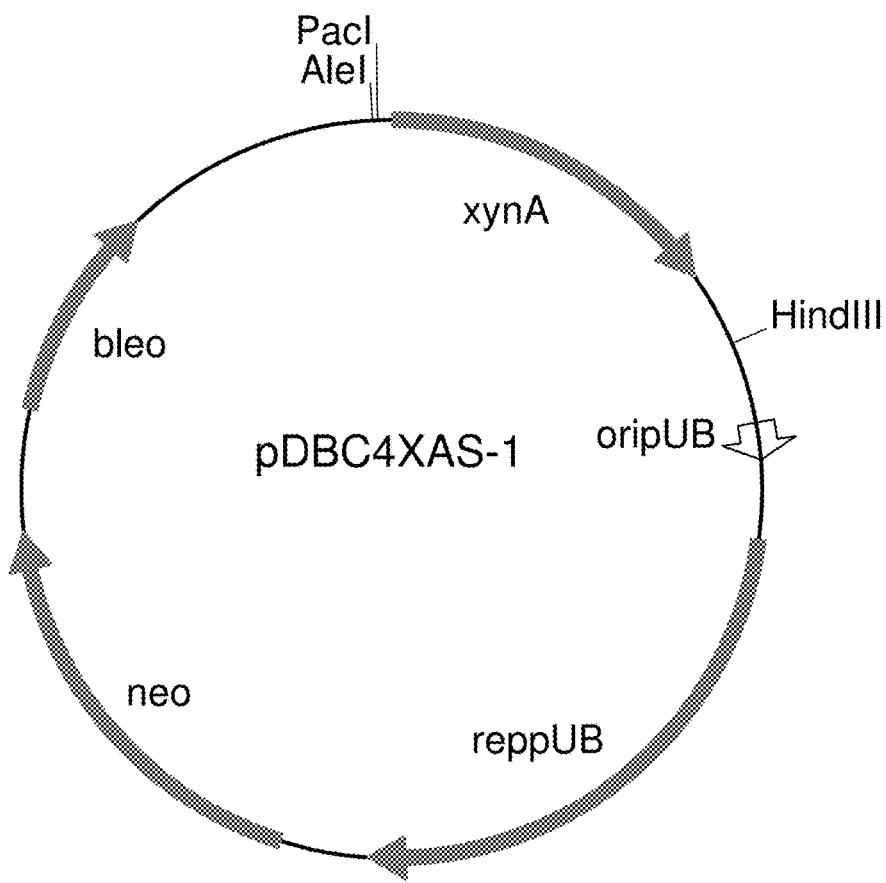
FIG. 1 sets out a schematic representation of the xynA expression plasmid pDBC4XAS-1.

SEQ ID NO: 1 sets out the sequence of the promoter PE4 of the *B. subtilis* bacteriophage SPO1 (indicated herewith as P15 promoter).

SEQ ID NO: 2 sets out the sequence of the promoter PE5 of the *B. subtilis* bacteriophage SPO1.

SEQ ID NO: 3 sets out the sequence of the forward primer for the 5'-flanking region of the xynA gene (including AleI, and PacI sites).

SEQ ID NO: 4 sets out the sequence of the reverse primer for the 3'-flanking region of the xynA gene (including HindIII site).

SEQ ID NO: 5 sets out the polynucleotide sequence of gene aprE coding for alkaline protease in *Bacillus subtilis*.

SEQ ID NO: 6 sets out the amino acid sequence of alkaline protease AprE in *Bacillus subtilis* encoded by the aprE gene of SEQ ID NO: 5.

SEQ ID NO: 7 sets out the polynucleotide sequence of the gene nprE coding for neutral protease NprE in *Bacillus subtilis*.

SEQ ID NO: 8 sets out the amino acid sequence of neutral protease NprE in *Bacillus subtilis* encoded by the nprE gene of SEQ ID NO: 7.

SEQ ID NO: 9 sets out the sequence of a synthetic DNA fragment containing a TthIIII site, 340 bp of 5'-amyE, BsmBI site, chloramphenicol selection marker, amyM terminator, BsmBI site, lox 66 site, spectinomycin selection marker, lox71 site, 120 bp of 3'-amyE and AsisI site.

SEQ ID NO: 10 sets out the sequence of the forward primer to amplify the xynA gene from *B. subtilis* 168 and introducing a BsmBI site.

SEQ ID NO: 11 sets out the sequence of the reverse primer to amplify the xynA gene from *B. subtilis* 168 and introducing a BsmBI site.

SEQ ID NO: 12 sets out the sequence of expression module G00 containing the *B. amyloliquefaciens* amyQ promoter sequence, the mobU ribosome binding site sequence as present on plasmid pDBC4XAS-1, including a NdeI site at the ATG start and two BsmBI sites at the 5' and 3' ends.

SEQ ID NO: 13 sets out the sequence of the expression module G01, $P_{Spo15}$_RK41_SWITCH deletion containing the P15 promoter, modified RNA leader sequence as described in EP2186880 and Ribosome binding site.

SEQ ID NO: 14 sets out the sequence of the expression module G01 according to SEQ ID NO: 13, modified by inclusion of a NdeI site at the ATG start and two BsmBI sites at the 5' and 3' ends.

SEQ ID NO: 15 sets out the sequence of the expression module G02 $P_{15\Omega grpE}$, containing the P15 promoter, mRNA stabilizing element as described in WO2008148575 and Ribosome binding site.

SEQ ID NO: 16 sets out the sequence of the expression module G02 of SEQ ID NO: 14, modified by inclusion of a NdeI site at the ATG start and two BsmBI sites at the 5' and 3' ends.

SEQ ID NO: 17 sets out the sequence of the forward primer to amplify on the amyE locus.

SEQ ID NO: 18 sets out the sequence of the reverse primer on xynA.

SEQ ID NO: 19 sets out the sequence of the amyE gene coding for neutral amylase in *Bacillus subtilis*.

SEQ ID NO: 20 sets out the amino acid sequence of neutral amylase from *Bacillus subtilis* coded by the amyE gene.

SEQ ID NO: 21 sets out the sequence of the forward primer to amplify the 5'-amyE region and introduce a StuI site.

SEQ ID NO: 22 sets out the sequence of the reverse primer to amplify the 5'-amyE region and introducing NotI, HindIII and KnpI sites.

SEQ ID NO: 23 sets out the sequence of the forward primer to amplify the 3'-amyE region and introducing NotI, HindIII and KnpI sites.

SEQ ID NO: 24 sets out the sequence of the reverse primer to amplify the 3'-amyE region and introduce a XhoI site.

SEQ ID NO: 25 sets out the sequence of the forward primer to amplify the amyM gene and introduce a NotI site and amyQ promoter sequence, PacI and NdeI site.

SEQ ID NO: 26 sets out the sequence of the reverse primer to amplify the amyM gene and introduce a HindIII site.

SEQ ID NO: 27 sets out the sequence of the amyM gene obtained from *Geobacillus stearothermophilus* coding for the glucan 1,4-α-maltohydrolase.

SEQ ID NO: 28 sets out the sequence of the glucan 1,4-α-maltohydrolase from *Geobacillus stearothermophilus* coded by the amyM gene according to SEQ ID NO: 27.

SEQ ID NO: 29 sets out the sequence of the modified expression module G03, containing the dual sigma 37 and sigma 55 promoter (Wang, P. Z., Doi R. H. (1984) "Overlapping promoters transcribed by *Bacillus subtilis* sigma 55 and sigma 37 RNA polymerase holoenzymes during growth and stationary phases." J Biol. Chem. 259(13): 8619-8625), the mobU ribosome binding site, and further containing a NotI site at the 5' end and a NdeI site at the 3' end.

SEQ ID NO: 30 sets out the sequence of the modified expression module G04, containing the rapA promoter, the mobU ribosome binding site and further containing a NotI site at the 5' end and a NdeI site at the 3' end.

SEQ ID NO: 31 sets out the sequence of the modified expression module G05 containing the PE5 promoter, the mobU ribosome binding site and further containing a NotI site at the 5' end and a NdeI site at the 3' end.

SEQ ID NO: 32 sets out the sequence of the modified expression module G06 containing the P15 and PE5 promoter, the mobU ribosome binding site, and further containing a NotI site at the 5' end and a NdeI site at the 3' end.

SEQ ID NO: 33 sets out the sequence of the modified expression module G07 containing the P15 promoter, the mobU ribosome binding site, and further containing a NotI site at the 5' end and a NdeI site at the 3' end.

SEQ ID NO: 34 sets out the sequence of the expression module G01 according to SEQ ID NO: 13, modified by inclusion of a NotI site at the 5' end and a NdeI site at the 3' end.

SEQ ID NO: 35 sets out the sequence of the expression module G02 of SEQ ID NO: 14, modified by inclusion of a NotI site at the 5' end and a NdeI site at the 3' end.

SEQ ID NO: 36 sets out the polynucleotide sequence of nucleotides 22 to 50 of the promoter PE4 of the *B. subtilis* bacteriophage SPO1 (indicated herewith as P15 promoter) of SEQ ID NO: 1.

SEQ ID NO: 37 sets out the sequence of forward primer to amplify the amyE locus outside the 5'-flank.

SEQ ID NO: 38 sets out the sequence of the reverse primer to amplify the amyE locus outside the 3'-flank.

SEQ ID NO: 39 sets out the sequence of the gene spoIIE from *B. subtilis*.

SEQ ID NO: 40 sets out the amino acid sequence of the polypeptide coded by the spoIIE gene from *B. subtilis*.

SEQ ID NO: 41 sets out the polynucleotide sequence of the xynA gene encoding the endo-1,4-beta-xylanase enzyme from *B. subtilis* 168.

SEQ ID NO: 42 sets out the polynucleotide sequence of the gene npr coding for neutral protease Npr in *Bacillus amyloliquefaciens*.

SEQ ID NO: 43 sets out the amino acid sequence of neutral protease Npr in *Bacillus amyloliquefaciens* encoded by the npr gene of SEQ ID NO: 42.

SEQ ID NO: 44 sets out the polynucleotide sequence of gene apr coding for alkaline protease in *Bacillus amyloliquefaciens*.

SEQ ID NO: 45 sets out the amino acid sequence of alkaline protease Apr in *Bacillus amyloliquefaciens* encoded by the apr gene of SEQ ID NO: 44.

SEQ ID NO: 46 sets out the polynucleotide sequence of gene apr coding for alkaline protease in *Bacillus licheniformis*.

SEQ ID NO: 47 sets out the amino acid sequence of alkaline protease Apr in *Bacillus licheniformis* encoded by the apr gene of SEQ ID NO: 46.

SEQ ID NO: 48 sets out the nucleic acid sequence of the mRNA stabilizing element (aprE) according to SEQ ID NO: 1 of WO08148575.

SEQ ID NO: 49 sets out the nucleic acid sequence of the mRNA stabilizing element (grpE) according to SEQ ID NO: 2 of WO08148575.

SEQ ID NO: 50 sets out the nucleic acid sequence of the mRNA stabilizing element (cotG) according to SEQ ID NO: 3 of WO08148575.

SEQ ID NO: 51 sets out the nucleic acid sequence of the mRNA stabilizing element according to SEQ ID NO: 4 of WO08148575.

SEQ ID NO: 52 sets out the nucleic acid sequence of the mRNA stabilizing element according to SEQ ID NO: 5 of WO08148575.

SEQ ID NO: 53 sets out the nucleic acid sequence of the mRNA stabilizing element according to SEQ ID NO: 4 of WO08140615.

SEQ ID NO: 54 sets out the nucleic acid sequence of the mRNA stabilizing element according to SEQ ID NO: 6 of WO08140615.

SEQ ID NO: 55 sets out the nucleic acid sequence of the rib leader according to SEQ ID NO: 42 of EP2186880.

SEQ ID NO: 56 sets out the polynucleotide sequence of the amy gene coding for neutral amylase in *Bacillus amyloliquefaciens*.

SEQ ID NO: 57 sets out the amino acid sequence of neutral amylase from *Bacillus amyloliquefaciens* coded by the amy gene according to SEQ ID NO: 56.

SEQ ID NO: 58 sets out the polynucleotide sequence of the amy gene coding for neutral amylase in *Bacillus licheniformis*.

SEQ ID NO: 59 sets out the amino acid sequence of neutral amylase from *Bacillus licheniformis* coded by the amy gene according to SEQ ID NO: 58.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

In a first aspect the invention provides a recombinant *Bacillus* host cell deficient in the production of a neutral protease and/or of an alkaline protease which host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.

*Bacillus* host cells deficient in the production of neutral protease (Npr, also known as bacillolysin or metalloprotease) and/or alkaline protease (Apr, also known as subtilisin) have e.g. been described by Kawamura et al (cited herewith) and in EP246678.

In the contest of the present invention "a host cell deficient in the production of compound" is herein defined as a host cell derived from a parent host cell which parent host cell contains the gene coding for the compound and expresses said compound. In the contest of the present invention the compound may be e.g. neutral protease and/or alkaline protease and/or α-amylase and/or a compound coded by a sporulation related gene. Preferably the *Bacillus* host cell is deficient in the production of neutral protease and alkaline protease. Said host cell derived from the parent host cell has been modified, preferably in its genome, to result in a phenotypic feature wherein the cell: a) produces less or substantially no compound, and/or b) produces a compound, which has substantially less or no biological activity, e.g. enzymatic activity as compared to the compound, produced by the parent host cell that has not been modified, when analysed under the same conditions and/or a combination of a) and b). In one embodiment a host cell which is deficient in the production of a compound is a host cell which has been modified, preferably in its genome, and which produces substantially no compound.

Deficiency in the production of a compound, as defined herein may be measured by methods known to those skilled in the art, e.g. it can be measured by determining the concentration and/or (specific) activity of the compound and/or it may be measured by determining the concentration of mRNA transcribed from the genes coding for the compound as described herein and/or it may be measured by gene or genome sequencing if compared to the parent host cell which has not been modified.

A modification in the genome can be determined by comparing the DNA sequence of the host cell deficient in the production of compound to the DNA sequence of the parent (non-modified) microbial host cell. Sequencing of DNA and genome sequencing can be done using standard methods known to the person skilled in the art, for example using Sanger sequencing technology and/or next generation sequencing technologies such as Illumina GA2, Roche 454, etc. as reviewed in Elaine R. Mardis (2008), Next-Generation DNA Sequencing Methods, Annual Review of Genomics and Human Genetics, 9: 387-402. (doi:10.1146/annurev.genom.9.081307.164359)

Deficiency in the production of a compound as described herein can be measured using any assay suitable to the measurement of the biological activity of the compound, e.g. polypeptide enzymatic activity as defined herein available to the skilled person, by e.g. measuring levels, concentrations and/or fluxes of metabolites involved in the enzymatic reaction, by quantitative proteomics techniques such as APEX or iTRAQ tools, by transcriptional profiling, by Northern blotting RT-PCR, by Q-PCR or by Western blotting. In particular quantifying the concentration of mRNA present in a cell may for example be achieved by northern blotting (in Molecular Cloning: A Laboratory Manual, Sambrook et al., New York: Cold Spring Harbour Press, 1989). Quantifying the concentration of polypeptide present in a cell may for example be achieved by western blotting. The difference in mRNA concentration may also be quantified by DNA array analysis (Eisen, M. B. and Brown, P.O. DNA arrays for analysis of gene expression. Methods Enzymol. 1999, 303:179-205). For example deficiency in the production of a protease as described herein or deficiency in the production of an α-amylase as described herein can be measured using any assay known to those skilled in the art, suitable to the measurement of the polypeptide enzymatic activity. α-amylase activity may for example be measured using a Megazyme CERALPHA alpha amylase assay kit (Megazyme International Ireland Ltd., Co. Wicklow, Ireland) according to the manufacturer's instruction. Protease activity may for example be measured on skim milk plate assay as described in Kawamura et at J. Bacteriol (1984) p 442-444 and/or by measuring the protease activity in the supernatant as described in Kawamura and according to a method by Millet J. Appl. Bacteriol (1970) 33: 207-219.

Deficiency of the host cell deficient in the production of a compound is preferably measured relative to the parent cell that is not deficient. A host cell deficient in the production of a compound produces less or substantially no compound and/or produces a compound which has less or substantially no biological activity, e.g. substantially no enzymatic activity.

In one embodiment the *Bacillus* host cell produces 1% less compound as defined herein if compared with the parent host cell which has not been modified and measured under the same conditions, at least 5% less, at least 10% less, at least 20% less, at least 30% less, at least 40% less, at least 50% less, at least 60% less, at least 70% less, at least 80% less, at least 90% less, at least 91% less, at least 92% less, at least 93% less, at least 94% less at least 95% less, at least 96% less, at least 97% less, at least 98% less, at least 99% less, or at least 99.9% less. Preferably the *Bacillus* host cell produces substantially no compound as described herein if compared with the parent microbial host cell which has not been modified and measured under the same conditions.

In one embodiment the *Bacillus* host cell produces a compound as defined herein with 1% less biological activity (e.g. enzymatic activity) as defined herein, if compared with the parent host cell which has not been modified and measured under the same conditions, at least 5% less activity, at least 10% less activity, at least 20% less activity, at least 30% less activity, at least 40% less activity, at least 50% less activity, at least 60% less activity, at least 70% less activity, at least 80% less activity, at least 90% less activity, at least 91% less activity, at least 92% less activity, at least 93% less activity, at least 94% less activity, at least 95% less activity, at least 96% less activity, at least 97% less activity, at least 98% less activity, at least 99% less activity, or at least 99.9% less activity. Preferably the *Bacillus* host cell produces a compound with substantially no activity if compared with the parent host cell which has not been modified and analysed under the same conditions.

The host cell may produce at least 80% less of the compound, and/or may have at least 80% reduced expression level of the mRNA transcribed from the gene coding for the compound and/or may have an at least 80% decreased biological activity, e.g. 80% decreased (specific) enzymatic activity of the compound as compared to the parent cell which has not been modified. Preferably the host cell produces at least 85% less, preferably at least 90% less, even more preferably at least 95% less, at least 96% less, at least 97% less, at least 98% less, at least 99% less, at least 99.5% less, at least 99.9% less of the compound, and/or has an at least 85%, preferably at least 90%, even more preferably at least 95%, at least 96%, at least 97%, at least 98%, at least 99%, at least 99.5%, at least 99.9% reduced expression level of the mRNA transcribed from the gene coding for the compound and/or has an at least 85%, preferably at least 90%, even more preferably at least 95%, at least 96%, at least 97%, at least 98%, at least 99%, at least 99.5%, at least 99.9% decreased biological activity, e.g. decreased (specific) enzymatic activity of the compound as compared to the parent cell which has not been modified when measured under the same conditions. Most preferably the host cell produces no compound, and/or has no expression level of the mRNA transcribed from the gene coding for the compound and/or produces a compound which has no biological activity, e.g. no (specific) enzymatic activity if compared to the parent cell which has not been modified.

Within the context of the present invention "measured under the same conditions" or "analysed under the same conditions" means that the *Bacillus* host cell deficient in the production of the compound and the host cell to which it is compared, e.g. the parent host cell, are cultivated under the same conditions and that the amount and/or biological activity of the compound in the *Bacillus* host cell deficient in the compound, if compared to host cell of comparison, is measured in both host cells, using the same conditions, preferably by using the same assay and/or methodology, more preferably within the same experiment.

In one embodiment according to the invention, the *Bacillus* host cell is deficient in a neutral protease Npr (such as NprE), or homologue thereto, coded by a npr gene (such as nprE gene) or a gene homologous thereto.

Within the context of the present invention the term "homologous" can be understood as referring to gene or protein from the same or different but usually related species, which correspond in function to each other or are very similar to each other. The term encompasses ortholog genes or proteins and paralog genes or proteins. Orthologs genes or proteins refer to genes or proteins in different species that have evolved from a common ancestral gene by speciation and which typically retain the same function during evolution. The term homologous also encompasses paralog gene or protein. Paralog gene or protein relate to genes or protein that are related by duplication within a genome, i.e. to genes or proteins having the same or a related function within the same species.

Homologous genes or proteins may be characterised by a high level of sequence identity. For example the neutral protease protein from *B. subtilis* has a sequence identify of 82% with the neutral protease protein from *B. amyloliquefaciens*. The alkaline protease from *B. subtilis* AprE has 86% identity with Apr from *B. amyloliquefaciens* and has 65% identity with Apr from *B. licheniformis*.

Preferably the neutral protease is encoded by a polynucleotide sequence according to SEQ ID NO: 7 or SEQ ID NO: 42 or a by a polynucleotide sequence at least 60% identical to SEQ ID NO: 7 or SEQ ID NO: 42, preferably by a polynucleotide sequence at least 65%, 70%, 75%, 80%, 85%, 90%, 95%, 96%, 97%, 98%, 99% identical to SEQ ID NO: 7 or SEQ ID NO: 42. Preferably the neutral protease has an amino acid sequence according to SEQ ID NO: 8 or SEQ ID NO: 43 or an amino acid sequence at least 60% identical to SEQ ID NO: 8 or SEQ ID NO: 43, preferably an amino acid sequence at least 65%, 70%, 75%, 80%, 85%, 90%, 95%, 96%, 97%, 98%, 99% identical to SEQ ID NO: 8 or SEQ ID NO: 43.

Preferably the neutral protease is encoded by a polynucleotide sequence according to SEQ ID NO: 7 or a by a polynucleotide sequence at least 60% identical to SEQ ID NO: 7, preferably by a polynucleotide sequence at least 65%, 70%, 75%, 80%, 85%, 90%, 95%, 96%, 97%, 98%, 99% identical to SEQ ID NO: 7. Preferably the neutral protease has an amino acid sequence according to SEQ ID NO: 8 or an amino acid sequence at least 60% identical to SEQ ID NO: 8, preferably an amino acid sequence at least 65%, 70%, 75%, 80%, 85%, 90%, 95%, 96%, 97%, 98%, 99% identical to SEQ ID NO: 8.

In another embodiment according to the invention, the *Bacillus* host cell is deficient in an alkaline protease Apr or homologue thereto, coded by a apr gene or a gene homologous thereto.

Preferably the alkaline protease is encoded by a polynucleotide sequence according to SEQ ID NO: 5, SEQ ID NO: 44 or SEQ ID NO: 46 or a by a polynucleotide sequence at least 60% identical to SEQ ID NO: 5, SEQ ID NO: 44 or SEQ ID NO: 46, preferably by a polynucleotide sequence at least 65%, 70%, 75%, 80%, 85%, 90%, 95%, 96%, 97%, 98%, 99% identical to SEQ ID NO: 5, SEQ ID NO: 44 or SEQ ID NO: 46. Preferably the alkaline protease has an amino acid sequence according to SEQ ID NO: 6, SEQ ID NO: 45 or SEQ ID NO: 47 or an amino acid sequence at least 60% identical to SEQ ID NO: 6, SEQ ID NO: 45 or SEQ ID NO: 47, preferably an amino acid sequence at least 65%, 70%, 75%, 80%, 85%, 90%, 95%, 96%, 97%, 98%, 99% identical to SEQ ID NO: 6, SEQ ID NO: 45 or SEQ ID NO: 47.

Preferably the alkaline protease is encoded by a polynucleotide sequence according to SEQ ID NO: 5 or a by a polynucleotide sequence at least 60% identical to SEQ ID NO: 5, preferably by a polynucleotide sequence at least 65%, 70%, 75%, 80%, 85%, 90%, 95%, 96%, 97%, 98%, 99% identical to SEQ ID NO: 5. Preferably the alkaline protease has an amino acid sequence according to SEQ ID NO: 6 or an amino acid sequence at least 60% identical to SEQ ID NO: 6, preferably an amino acid sequence at least 65%, 70%, 75%, 80%, 85%, 90%, 95%, 96%, 97%, 98%, 99% identical to SEQ ID NO: 6.

In yet another embodiment according to the invention, the *Bacillus* host cell is further deficient in the production of a neutral α-amylase, preferably it is deficient in the production of a natural α-amylase encoded by the amy (e.g. amyE) gene.

Preferably the neutral α-amylase is encoded by a polynucleotide sequence according to SEQ ID NO: 19, SEQ ID NO: 56 or SEQ ID NO: 58 or a by a polynucleotide sequence at least 60% identical to SEQ ID NO: 19, SEQ ID NO: 56 or SEQ ID NO: 58, preferably by a polynucleotide sequence at least 65%, 70%, 75%, 80%, 85%, 90%, 95%, 96%, 97%, 98%, 99% identical to SEQ ID NO: 19, SEQ ID NO: 56 or SEQ ID NO: 58. Preferably the neutral α-amylase has an amino acid sequence according to SEQ ID NO: 20, SEQ ID NO: 57 or SEQ ID NO: 59 or an amino acid sequence at least 60% identical to SEQ ID NO: 20, SEQ ID NO: 57 or SEQ ID NO: 59, preferably an amino acid sequence at least 65%, 70%, 75%, 80%, 85%, 90%, 95%, 96%, 97%, 98%, 99% identical to SEQ ID NO: 20, SEQ ID NO: 57 or SEQ ID NO: 59.

Preferably the neutral α-amylase is encoded by a polynucleotide sequence according to SEQ ID NO: 19 or a by a polynucleotide sequence at least 60% identical to SEQ ID NO: 19, preferably by a polynucleotide sequence at least 65%, 70%, 75%, 80%, 85%, 90%, 95%, 96%, 97%, 98%, 99% identical to SEQ ID NO: 19. Preferably the neutral α-amylase has an amino acid sequence according to SEQ ID NO: 20 or an amino acid sequence at least 60% identical to SEQ ID NO: 20, preferably an amino acid sequence at least 65%, 70%, 75%, 80%, 85%, 90%, 95%, 96%, 97%, 98%, 99% identical to SEQ ID NO: 20.

In the contest of the present invention ortholog may be understood as a polynucleotide or amino acid sequence derived from other *Bacillus* host cells than the *Bacillus* host cell from which the protease (e.g. NprE or AprE) coded by the protease gene or the neutral α-amylase (e.g. AmyE) coded by the neutral α-amylase gene (e.g. amyE) is derived.

Paralog may be understood as a polynucleotide sequences or amino acid sequence homologous to the protease gene (e.g. nprE or aprE) or homologous to the protease (e.g. NprE or AprE) or homologous to the neutral α-amylase (e.g. AmyE) or homologous to the neutral α-amylase gene (e.g. amyE) and derived from the same *Bacillus* host.

For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region. Preferably the percentage of sequence identity is calculated over the full length of the amino acid sequence or over the full length of the nucleotide sequence.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percentage of sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp. 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

The recombinant *Bacillus* host cell according to the invention comprises a nucleic acid construct comprising a polynucleotide encoding a compound of interest or encoding a compound involved in the synthesis of a compound of interest operably linked to a promoter sequence allowing for expression of the polynucleotide in the host cell.

In the context of the present invention the term "nucleic acid construct" is synonymous with expression cassette or expression vector and is herein defined as a nucleic acid molecule, either single- or double-stranded, which is isolated from a naturally occurring gene or which has been modified to contain segments of nucleic acid which are combined and juxtaposed in a manner which would not otherwise exist in nature. The nucleic acid construct contains all the control sequences required for expression of DNA coding sequence, e.g. of a polynucleotide encoding a compound of interest or encoding a compound involved in the synthesis of a compound of interest, wherein said control sequences are operably linked to said polynucleotide. Typically the nucleic acid construct will comprise at least a promoter operably linked to the coding sequence to be expressed in a host cell and a terminator sequence.

The term "operably linked" as used herein refers to two or more nucleic acid sequence elements that are physically linked and are in a functional relationship with each other. For instance, a control sequence, e.g. a promoter, is operably linked to a DNA coding sequence if the promoter is able to initiate or regulate the transcription or expression of a coding sequence, i.e. in a configuration in which the control sequence is appropriately placed at a position relative to the coding sequence such that the control sequence directs the production of an RNA or an mRNA and optionally of a polypeptide translated from said (m)RNA, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

The term "control sequences" is defined herein to include all components, which are necessary or advantageous for the expression of mRNA and/or a polypeptide, either in vitro or in a host cell. Each control sequence may be native or foreign to the nucleic acid sequence encoding the compound of interest or a compound related to the compound of interest. Such control sequences include, but are not limited to, a leader, Shine-Delgarno sequence (also indicated as Ribosome Binding Site), a polyadenylation sequence, a pro-peptide sequence, a pre-pro-peptide sequence, a promoter, a signal sequence, and a transcription terminator.

The control sequences may be provided with linkers for the purpose of introducing specific restriction sites facilitating ligation of the control sequences with the coding region of the nucleic acid sequence encoding a polypeptide.

The control sequence may be an appropriate promoter sequence (promoter).

The control sequence may also be a suitable transcription terminator (terminator) sequence, a sequence recognized by a host cell to terminate transcription. The terminator sequence is operably linked to the 3'-terminus of the nucleic acid sequence encoding the polypeptide. Any terminator, which is functional in the cell, may be used in the present invention. The person skilled in the art knows which types of terminators can be used in the host cell as described herein.

The control sequence may also be a 5'-untranslated sequence (also known as leader sequence), a non-translated region of a mRNA which is important for translation by the host cell. The translation initiation sequence or 5'-untranslated sequence is operably linked to the 5'-terminus of the coding sequence encoding the compound of interest of the compound related to the compound of interest. Any leader sequence, which is functional in the cell, may be used in the present invention. Leader sequences may be those originating from bacterial α-amylase (amyE, amyQ and amyL) and bacterial alkaline protease aprE and neutral protease genes nprE (*Bacillus*), or signal sequences as described in WO2010/121933, in WO2013007821 and WO2013007820.

Each control sequence may be native or foreign to the nucleic acid sequence encoding the polypeptide. Control sequences may be optimized to their specific purpose.

The control sequence may also be a polyadenylation sequence, a sequence which is operably linked to the 3'-terminus of the nucleic acid sequence and which, when transcribed, is recognized by the host cell (mutated or parent) as a signal to add polyadenosine residues to transcribed mRNA. Any polyadenylation sequence, which is functional in the cell, may be used in the present invention.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors.

In the context of the present invention an "expression module" is herewith defined as a part of a nucleic acid construct comprising at least a promoter and a sequence coding for a Ribosome biding site and optionally comprising a mRNA stabilizing element and/or a modified rib leader.

In the context of the invention a Ribosome Binding Site (RBS) is a sequence present on the mRNA that is bound by the ribosome when initiating protein translation. A genome analysis of *B. subtilis* learns that about 90% of the RBS are located between −5 and −11 and most frequently at −8 from the start codon and strong RBS are close to the consensus sequence AAAGGAGG. (Rocha E.P., Danchin A., Viari A. Translation in *Bacillus subtilis*: roles and trends of initiation and termination, insights from a genome analysis Nucleic Acids Res. 1999 27(17):3567-3576). Analyses of 30 prokaryotic genomes demonstrated that most RBS sequences harboured at least four bases of the AGGAGG core motif (Ma J., Campbell A., Karlin S. J. Correlations between Shine-Dalgarno sequences and gene features such as predicted expression levels and operon structures. Bacteriol. 2002 184(20):5733-45).

The *Bacillus* host cell according to the invention comprises a promoter sequence allowing for expression of the polynucleotide encoding a compound of interest or encoding a compound involved in the synthesis of a compound of interest in the host cell, wherein the promoter comprises a bacteriophage promoter sequence, more preferably a bacteriophage SPO1 promoter sequence.

A bacteriophage promoter sequence is herewith defined as a promoter sequence derived from a bacteriophage, i.e. derived from a virus that infects and replicates in bacteria.

The term "derived from" also includes the terms "originated from," "obtained from," "obtainable from," "isolated from," and "created from," and generally indicates that one specified material find its origin in another specified material or has features that can be described with reference to the another specified material. As used herein, a substance (e.g., a nucleic acid molecule or polypeptide) "derived from" a microorganism preferably means that the substance is native to that microorganism.

Suitable bacteriophage promoters are promoters which may be recognized by *Bacillus* RNA polymerases and which therefore allow for expression of the polynucleotide encoding a compound of interest or encoding a compound involved in the synthesis of a compound of interest operably linked to said bacteriophage promoter in the *Bacillus* host cell. Typically suitable bacteriophage promoters may be derived from a bacteriophage that infects and replicates in *Bacillus* host cells. Suitable bacteriophages that infect *Bacillus* host cells are phie, SPO1, SP82, SP5, SP6, SP7, SP8, SP9, SP13, SP3, SP10, PBS1, SP alpha, and SP beta (Anna M. Brodetskyl and W. R. Romig J Bacteriol. 1965 90(6): 1655-1663. Characterization of *Bacillus subtilis* Bacteriophages). The bacteriophage promoter may be selected for its efficiency in directing the expression of the polynucleotide encoding the compound of interest or a compound involved in the synthesis of the compound of interest in a *Bacillus* host. A suitable promoter may be one which is an "inducible promoter" is one which causes mRNA synthesis of a gene to be initiated temporally under specific conditions. Alternatively, a promoter may be a "constitutive" promoter, i.e. one that permits the gene to be expressed under virtually all environmental conditions, i.e. a promoter that directs constant, non-specific gene expression. A "strong constitutive promoter", i.e., a promoter which causes mRNAs to be initiated at high frequency compared to a native host cell may be used.

In a preferred embodiment according to the invention the bacteriophage promoter sequence is a bacteriophage SPO1 promoter sequence, i.e. promoter sequences derived from *B. subtilis* bacteriophage SPO1. Bacteriophage SPO1 promoter sequences have been described in Stewart et al VIROLOGY 246, 329-340 (1998). Suitable bacteriophage SPO1 promoter sequences may be any of PE1, PE2, PE3, PE4, PE5, PE6, PE7, PE8, PE9, PE10, PE11 or PE12 bacteriophage SPO1 promoter sequences as described in FIG. 2 of Stewart et al cited herein. A suitable promoter sequence may be a fusion of any of PE1 to PE12 bacteriophage SPO1 promoter with at least one of any of PE1 to PE12 bacteriophage SPO1 promoter wherein said fusion is operably linked to the polynucleotide encoding a compound of interest or encoding a compound involved in the synthesis of a compound of interest.

Preferably the *Bacillus* host cell according to the invention, comprises a bacteriophage SPO1 promoter sequence wherein the SPO1 bacteriophage promoter sequence comprises a polynucleotide sequence according to SEQ ID NO: 36 or a polynucleotide sequence at least 70% identical to SEQ ID NO: 36, preferably a polynucleotide sequence at least 75%, 80%, 85%, 90%, 95%, 96%, 97%, 98%, 99% identical to SEQ ID NO: 36.

In a more preferred embodiment the bacteriophage SPO1 promoter is a polynucleotide sequence according to SEQ ID NO: 1 or a polynucleotide sequence at least 70% identical to SEQ ID NO: 1, preferably a polynucleotide sequence at least 75%, 80%, 85%, 90%, 95%, 96%, 97%, 98%, 99% identical to SEQ ID NO: 1. Preferably the bacteriophage SPO1 promoter is a PE4 or PE5, more preferably a promoter according to SEQ ID NO: 1 or SEQ ID NO: 2. In the context of the present invention the PE4 bacteriophage SPO1 promoter may be indicated as P15 promoter.

It has been surprisingly found that when a *Bacillus* host cell according to the invention comprising a nucleic acid construct wherein the polynucleotide encoding a compound of interest or encoding a compound involved in the synthesis of a compound of interest is operably linked to a bacteriophage SPO1 promoter sequence, e.g. a PE4 and/or PE5 promoter sequence, higher expression of the polynucleotide can be obtained if compared to host cells comprising other promoters largely used in *Bacillus* host cells such as the *Bacillus amyloliquefaciens* amyQ promoter.

In a preferred embodiment, the bacteriophage promoter, preferably the SPO1 bacteriophage promoter, more preferably the PE4 and/or PE5 SPO1 bacteriophage promoter, such as the promoter according to SEQ ID NO: 1 or 2 or a promoter sequence at least 70% identical thereto as indicated herewith present in the *Bacillus* cell according to the invention, is part of an expression module.

Said expression module comprises the promoter, a sequence coding for a RBS and optionally a mRNA stabilizing element and/or or a modified rib leader. Preferably the expression module comprises the promoter, a mRNA stabilizing element and/or a modified rib leader and a sequence coding for a RBS. More preferably the expression module comprises a mRNA stabilizing element and/or modified rib leader located downstream of the promoter and upstream of a sequence coding for a RBS. In one embodiment the expression module comprises a mRNA stabilizing element located downstream of the promoter and upstream of a sequence coding for a to a RBS.

In the context of the present invention, the term "mRNA stabilizing element" as used herein refers to a DNA sequence located downstream of the promoter region and upstream of the translation initiation site (i.e. RBS) of the polynucleotide encoding a compound of interest or encoding a compound involved in the synthesis of a compound of interest to which the promoter region is operably linked such that all mRNAs synthesized from the promoter region may be processed to generate mRNA transcript with a stabilizer sequence at the 5'-end of the transcript. The presence of such a stabilizer sequence at the 5'end of the mRNA transcripts increases their half-life (Hue et al, (1995) *Journal of Bacteriology* 177: 3465-3471). Suitable mRNA stabilizing elements are those described in WO08148575 (preferably SEQ ID NO: 1 to 5 of WO08140615), or fragments of these sequences which maintain the mRNA stabilizing function) and in WO08140615 (preferably *Bacillus thuringiensis* CryIIIA mRNA stabilising sequence or bacteriophage SP82 mRNA stabilising sequence, more preferably a mRNA stabilising sequence according to SEQ ID NO: 4 or 5 of WO08140615, more preferably a modified mRNA stabilising sequence according to SEQ ID NO: 6 of WO08140615), or fragments of these sequences which maintain the mRNA stabilizing function. Preferred mRNA stabilizing elements are selected from the group consisting of aprE, grpE, cotG, SP82, RSBgsiB, CryIIIA mRNA stabilizing elements, preferably mRNA stabilising elements according to SEQ ID NO: 48 to 52 respectively (corresponding to SEQ ID NO: 1 to 5, respectively, of WO08148575), and according to SEQ ID NO: 53 or 54 (corresponding to SEQ ID NO: 4 and 6, respectively of WO08140615), or according to fragments of these sequences which maintain the mRNA stabilizing function. A preferred mRNA stabilizing element is the grpE mRNA stabilizing element, preferably according to SEQ ID NO: 49 (corresponding to SEQ ID NO: 2 of WO08148575).

In another embodiment the expression module comprises a modified rib leader located downstream of the promoter and upstream of a sequence coding for a to a RBS.

In the context of the present invention a rib leader is herewith defined as the leader sequence upstream of the riboflavin biosynthetic genes (rib operon) in a *Bacillus* cell, more preferably in a *Bacillus subtilis* cell. In *Bacillus subtilis*, the rib operon, comprising the genes involved in riboflavin biosynthesis, include ribG (ribD), ribB (ribE), ribA, and ribH genes. Transcription of the riboflavin operon from the rib promoter (Prib) in *B. subtilis* is controlled by a riboswitch involving an untranslated regulatory leader region (the rib leader) of almost 300 nucleotides located in the 5'-region of the rib operon between the transcription start and the translation start codon of the first gene in the operon, ribG.

In one embodiment the non-modified rib leader is a rib leader according to SEQ ID NO: 55 (corresponding to SEQ ID NO: 42 of EP2186880). A modified rib leader may contain one or more ribO mutations i.e. one or more, such as e.g. 1, 2, 3, 4, 5, 6, 7, 8, 9, 10, 11, 12, ribO mutations, i.e. substitution(s), on a position corresponding to a position as depicted in SEQ ID NO: 55 which is selected from e.g. position 31, 39, 40, 41, SS, 85, 86, 88, 93, 116, 121, and 128. Preferably, the ribO mutation is selected from T31G, G39A, G40A, G41A, C55T, C85T, C86T, G88A, C93T, A116C, G121A, C128G, and combinations thereof wherein the nucleotides correspond to positions as depicted in SEQ ID NO: 55. More preferably the modified rib leader is a rib leader comprising the ribO mutation C85T, even more preferably it is a rib leader according to SEQ ID NO: 55 comprising the ribO mutation C85T (named RK41 in EP2186880 and herewith) in the corresponding position of SEQ ID NO: 55. A modified rib leader may contain a deletion of nucleotides corresponding to nucleotides 166 to 263 of SEQ ID NO: 55 named "SWITCH deletion" herewith and in EP2186880, optionally in combination with one or more ribO mutations, preferably in combination with the ribO mutation C85T. Therefore in a preferred embodiment the modified rib leader is a rib leader according to SEQ ID NO: 55 comprising the ribO mutation C85T (named RK41) in the corresponding position of SEQ ID NO: 55 and a deletion of nucleotides corresponding to nucleotides 166 to 263 of SEQ ID NO:55 (SWITCH deletion).

In one embodiment according to the invention, the *Bacillus* host cell according to the invention comprises an expression module comprising the promoter, a RBS and optionally a mRNA stabilizing element as defined herein and/or or a modified rib leader as defined herein.

The sequence coding for the RBS can be a sequence coding for the RBS which is naturally present in the gene comprising a polynucleotide encoding a compound of interest or encoding a compound involved in the synthesis of a compound of interest when said polynucleotide is derived from a prokaryote. Alternatively it can be any suitable sequence coding for an RBS known to those skilled in the art which may be used in *Bacillus* host cell. Suitable sequences coding for an RBS in the expression module according to the invention are sequence coding for 16S RBS, for a ribD RBS, for mobU RBS.

Preferred expression modules according to the invention have a polynucleotide sequence selected from SEQ ID NO:

13, SEQ ID NO: 14, SEQ ID NO: 15, SEQ ID NO: 16, SEQ ID NO: 31, SEQ ID NO: 32, SEQ ID NO: 33, SEQ ID NO: 34, SEQ ID NO: 35.

The *Bacillus* host cell according to the invention comprises a nucleic acid construct as herein defined comprising a polynucleotide encoding a compound of interest or encoding a compound involved in the synthesis of a compound of interest operably linked to a promoter sequence or expression module allowing for expression of the polynucleotide in the host cell as herein defined.

The nucleic acid construct comprises a polynucleotide encoding a compound of interest or a polynucleotide encoding a compound involved in the synthesis of a compound of interest. In one embodiment the compound of interest is a biopolymer selected from a nucleic acid, polyamine, polyol, polypeptide (or polyamide), or polysaccharide, preferably the polypeptide may be an enzyme.

The compound of interest can be any biological compound. The biological compound may be biomass or a biopolymer or metabolite. The biological compound may be encoded by a single polynucleotide or a series of polynucleotides composing a biosynthetic or metabolic pathway or may be the direct result of the product of a single polynucleotide or products of a series of polynucleotides. The biological compound may be native to the host cell or heterologous.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptide may be native or may be heterologous to the host cell. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, an amylase, ceramidases, epoxide hydrolase, aminopeptidase, acylases, aldolase, hydroxylase, aminopeptidase, lipase. The polypeptide may also be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, a maltogenic amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, galactolipase, chlorophyllase, polyphenoloxidase, ribonuclease, transglutaminase, chlorophyllase, pheophytinase, or glucose oxidase, hexose oxidase, monooxygenase.

According to the present invention, a polypeptide or enzyme can also be a product as described in WO2010/102982. According to the present invention, a polypeptide can also be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell. Example of fusion polypeptides and signal sequence fusions are for example as described in WO2010/121933.

The biopolymer may be a polysaccharide. The polysaccharide may be any polysaccharide, including, but not limited to, a mucopolysaccharide (e. g., heparin and hyaluronic acid) and nitrogen-containing polysaccharide (e.g., chitin). In a more preferred option, the polysaccharide is hyaluronic acid.

The polynucleotide coding for the compound of interest or coding for a compound involved in the production of the compound of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are citric acid, gluconic acid, adipic acid, fumaric acid, itaconic acid, levulinic acid and succinic acid.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams. Other preferred metabolites are exo-metabolites. Examples of exo-metabolites are Aurasperone B, Funalenone, Kotanin, Nigragillin, Orlandin, Other naphtho-γ-pyrones, Pyranonigrin A, Tensidol B, Fumonisin B2 and Ochratoxin A.

The biological compound may also be the product of a selectable marker. A selectable marker is a product of a polynucleotide of interest which product provides for biocide or viral resistance, resistance to heavy metals, prototrophy to auxotrophs, and the like. Selectable markers include, but are not limited to, amdS (acetamidase), argB (ornithinecarbamoyltransferase), bar (phosphinothricinacetyltransferase), hygB (hygromycin phosphotransferase), niaD (nitrate reductase), pyrG (orotidine-5'-phosphate decarboxylase), sC (sulfate adenyltransferase), trpC (anthranilate synthase), ble (phleomycin resistance protein), hyg (hygromycin), NAT or NTC (Nourseothricin), kanamicine, tetracycline, chloramphenicol, neomycin, spectinomycin as well as equivalents thereof.

According to the invention, the compound of interest is preferably a polypeptide as described in the list of compounds of interest.

Preferably the compound of interest is an amylase, e.g. an α- or a β-amylase, e.g. a glucan 1,4-α-maltohydrolase such as the enzyme according to SEQ ID NO: 28. In another preferred embodiment the compound of interest is a endo-1,4-beta-xylanase protein as retrieved from EMBL Nucleotide Sequence Database (http://www.ebi.ac.uk/embl/iNdex.html) Accession numbers CDS:CAB13776 (SEQ ID NO: 41).

According to another embodiment of the invention, the compound of interest is preferably a metabolite.

The polynucleotide encoding the compound of interest or encoding a compound involved in the synthesis of the compound of interest may be cDNA or genomic DNA. The polynucleotide molecule can be single-stranded or double-stranded, but preferably is double-stranded DNA. Genomic DNA may refer to a nucleic acid molecule coding for a polypeptide chain that will typically include control sequences as defined herein preceding and following the Open Reading Frame. Genomic DNA may include nucleic acids that do not encode polypeptide, but rather provide templates for transcription of functional RNA molecules such as transfer RNAs, ribosomal RNAs, ribozymes, microRNAs, etc. The Open Reading Frame is herewith defined as the region of a gene that is transcribed and translated into polypeptide and which starts with a start codon, generally with the start codon ATG, and which does not contain any stop codon (TAA, TAG, TGA). Alternative start codons which can be found in e.g. *Bacillus* host cells are TTG and GTG (Rocha E.P., Danchin A., Viari A. Translation in *Bacillus subtilis*: roles and trends of initiation and termination, insights from a genome analysis Nucleic Acids Res. 1999 27(17):3567-3576). The Open Reading Frame in the context of the present invention contains coding sequences (exons) and may not contain intervening sequences (introns). In the context of the present invention when the polynucleotide encoding for a compound of interest or encoding for a compound involved in the synthesis of a compound of interest is derived from genomic DNA said genomic DNA typically will not include the promoter sequence naturally present in said genomic DNA and optionally will not include the RBS sequence naturally present in said genomic DNA.

A polynucleotide encoding the compound of interest or encoding a compound involved in the synthesis of the compound of interest, may be produced recombinantly, for example using PCR (polymerase chain reaction) cloning techniques, synthetically, or by any means available to those of skill in the art. They may also be cloned by standard techniques. A polynucleotide is typically provided in isolated and/or purified form.

To increase the likelihood that the introduced enzyme is expressed in active form by a cell of the invention, the corresponding encoding nucleotide sequence may be adapted to optimise its codon usage. Several methods for codon optimisation are known in the art. A preferred method to optimise codon usage of the nucleotide sequences to that of the chosen host cell is a codon pair optimization technology as disclosed in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

When the compound of interest is a polypeptide the polynucleotide may encode the mature polypeptide and the wild type signal sequence. Alternatively the polynucleotide may encode the mature polypeptide and a non-native signal sequence. For example when the polynucleotide is coding for glucan 1,4-α-maltohydrolase such as the enzyme according to SEQ ID NO: 28, any one of signal sequences yurI fliL, vpr, glpQ, phy, lytC, ywsB, ybbD, ybxI, yolA, ylqB, ybbC, pel, yckD, ywaD, ywmD, yweA, yraJ, dacF, yfjS, yybN, yrpD, yvcE, wprA, yxaL, ykwD, yncM2, sacB, phrC, SacC, yoqM, ykoJ, lip, yfkN, yurI, ybfO, yfkD, yoaJ, xynA, penP, ydjM, yddT, yojL, yomL, yqxI, yrvJ, yvpA, yjcM, yjfA, ypjP, ggt, yoqH, ywtD, ylaE, yraJ, lytB, lytD, nprB, nucB, rplR, yfhK, yjdB, ykvV, ybbE, yuiC, ylbL, yacD, yvpB and ynfF can be used to increase the secretion of glucan 1,4-α-maltohydrolase according to SEQ ID NO: 28 in *Bacillus subtilis* (WO2013007820). Other preferred signal sequences are those described in WO2013007821.

The polynucleotide encoding the compound of interest or encoding a compound involved in the synthesis of a compound of interest may be an isolated polynucleotide. An "isolated polynucleotide" is a DNA or RNA that is not immediately contiguous with both of the coding sequences with which it is immediately contiguous (one on the 5' end and one on the 3' end) in the naturally occurring genome of the organism from which it is obtained.

In the context of the present invention the nucleic acid construct is synonymous with expression vector. The expression vector according to the invention comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.

The expression vector may comprise the following elements operably linked to each other in a consecutive order from the 5'-end to 3'-end relative to the coding strand of the sequence encoding the compound of interest or encoding a compound involved in the synthesis of the compound of interest: (1) the promoter sequence capable of directing transcription of the nucleotide sequence encoding the compound of interest or the compound involved in the synthesis of the compound of interest; (2) optionally a sequence to facilitate the translation of the transcribed RNA, for example a ribosome binding site (also indicated as Shine Delgarno sequence) (3) optionally, a signal sequence capable of directing secretion of the compound of interest or a compound involved in the synthesis of a compound of interest from the Bacillus host cell into a culture medium; (4) a polynucleotide encoding a compound of interest or a polynucleotide encoding a compound involved in the synthesis of a compound of interest, as defined herein; and preferably also (5) a transcription termination region (terminator) capable of terminating transcription downstream of the nucleotide sequence encoding the compound of interest or a compound involved in the synthesis of a compound of interest. Element (1) and optionally element (2) can be part of an expression module as herein defined.

The origin of the terminator is not critical. The terminator can, for example, be native to the DNA sequence encoding the compound of interest or the compound involved in the synthesis of the compound of interest. However, preferably a bacterial terminator is used in bacterial host cells. More preferably, the terminator is endogenous to the host cell (in which the nucleotide sequence is to be expressed). The vector may comprise these and/or other control sequences as defined herein.

The coding portion of the mature transcripts expressed by the constructs will include a start codon, usually AUG (or ATG), but there are also alternative start codons, such as for example GUG (or GTG) and UUG (or TTG), which are used in prokaryotes. Also a stop or translation termination codon is appropriately positioned at the end of the polypeptide to be translated.

The expression vector may be any vector (e.g., a plasmid or virus), which can be conveniently subjected to recombinant DNA procedures and can bring about the expression of the polynucleotide encoding the compound of interest or encoding a compound involved in the synthesis of the compound of interest. The choice of the vector will typically depend on the compatibility of the vector with the Bacillus host cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. An autonomously replicating vector will typically further comprise an autonomous replication sequence. The autonomous replication sequence may be any suitable sequence available to the person skilled in the art that allows for plasmid replication that is independent of chromosomal replication. The origin of replication may be any plasmid replicator mediating autonomous replication that functions in a cell. The term "origin of replication" or "plasmid replicator" is defined herein as a nucleotide sequence that enables a plasmid or vector to replicate in vivo. Examples of bacterial origins of replication are the origins of replication of plasmids pBR322, pUC19, pACYC177, and pACYC184 permitting replication in *E. coli*, RSF1010 permitting replication in *Pseudomonas* is described, e.g., by F. Heffron et al., in Proc. Nat'l Acad. Sci. USA 72(9):3623-27 (September 1975), and pUB110, pE194, pTA1060, and pAMß1 permitting replication in *Bacillus*.

Alternatively, the vector may be one which, when introduced into the host cell, is integrated into the genome and replicated together with the chromosome(s) into which it has been integrated. The integrative vector may integrate at random or at a predetermined target locus in the chromosomes of the host cell. In a preferred embodiment of the invention, the integrative vector comprises a DNA fragment, which is homologous to a DNA sequence in a predetermined target locus in the genome of host cell for targeting the integration of the cloning vector to this predetermined locus. In order to promote targeted integration, the vector is preferably linearized prior to transformation of the cell. Linearization is preferably performed such that at least one but preferably either end of the vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb.

In one embodiment according to the invention the nucleic acid construct comprising a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence as described herein is integrated into the host cell genome.

In one embodiment of the invention the nucleic acid construct is integrated into a locus selected from the npr locus, the apr locus, or the amy locus. More preferably the nucleic acid construct is integrated into a locus selected from nprE locus, the amyE locus or the aprE locus, more preferably it is integrated into the amyE locus, or homologous loci thereof.

In another embodiment of the invention the Bacillus host cell according to the invention comprises more than one copy of the nucleic acid constructs as defined herein, more preferably it comprises more than one copy of the nucleic acid construct integrated into the host cell genome.

More than one copy of a nucleic acid construct may be inserted into the Bacillus host cell according to the invention to increase production of the compound (over-expression) encoded by said sequence. This can be done, preferably by integrating into its genome more copies of the DNA sequence. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The expression vector may be a single vector or plasmid or two or more vectors or plasmids, which together contain the total DNA to be introduced into the genome of the host cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. The selectable marker may be introduced into the cell on the expression vector as the expression cassette or may be introduced on a separate expression vector.

Markers which can be used in bacteria include ATP synthetase, subunit 9 (oliC), orotidine-5'-phosphatedecarboxylase (pvrA), the bacterial G418 resistance gene, resistance genes for neomycin, kanamycin, tetracycline, spectinomycin, erythromycin, chloramphenicol, phleomycin, hygromycin, bleomycin, methotrexate, orbenomyl resistance (benA) (*Bacillus*) and the *E. coli* uidA gene, coding for β-glucuronidase (GUS).

Alternatively, specific selectable markers can be used such as auxotrophic markers which require corresponding mutant host strains: e. g. D-alanine racemase (from *Bacillus*), or trpC. In a preferred embodiment the selection marker is deleted from the transformed host cell after introduction of the expression construct so as to obtain transformed host cells capable of producing the compound of interest or a compound involved in the synthesis of a compound of interest which are free of selection marker genes. Therefore in one embodiment of the invention the recombinant *Bacillus* host cell is a marker-free host cell.

In one embodiment the one or more nucleic acid constructs as defined herein to be integrated into the genome of the *Bacillus* host cell comprise a selectable marker located between two lox sites, wherein upon selection of those cells wherein integration into the genome has taken place by use of the selectable marker, said marker is deleted by site-specific recombination of the two lox sites by the action of Cre recombinase protein. The latter results in the deletion of the selectable marker from the genome and leave a single lox site in the genome of the *Bacillus* host cell. The term "lox site" as used herein refers to a nucleotide sequence at which the product of the cre gene of bacteriophage P1, the Cre recombinase, can catalyze a site-specific recombination event. The lox sites are site-specific recombination sites for the Cre recombinase. A variety of lox sites are known in the art, including the naturally occurring loxP, loxB, loxL and loxR, as well as a number of mutant, or variant, lox sites, such as lox66, lox71, loxP511, loxP514, loxΔ86, loxΔ117, loxC2, loxP2, loxP3 and lox P23. The site-specific recombination sites may be such that out-recombination following recombinase expression gives rise to a single mutant site-specific recombination site at the target locus which is not recognized by the recombinase. In particular, the lox sites may be lox66 and lox 71 (Albert, H., Dale, E. C., Lee, E., & Ow, D. W. (1995). Site-specific integration of DNA into wild-type and mutant lox sites placed in the plant genome. *Plant Journal*, 7(4), 649-659). In a specific embodiment, the lox66 and lox71 site-specific recombination sites may be such that out-recombination following recombinase expression gives rise to a lox72 mutant site-specific recombination site at the target locus which is not recognized by the recombinase.

Therefore in one embodiment according to the invention, in the recombinant *Bacillus* host cell according to the invention one or more nucleic acid constructs comprise a selectable marker located between two lox sites, preferably located between a lox66 and a lox71 site.

A Cre-lox system, can also be used to perform other recombination transformations in the *Bacillus* host cell according to the invention. For example it can be used to insert, replace or delete polynucleotide sequences at a target locus in the genome of the *Bacillus* host cell without leaving selectable markers in the host cell. A method for carrying out a recombination at a target locus in a host cell using the Cre-lox system for example as described in WO2013/135729 can be used at this regard.

Therefore in another embodiment the recombinant *Bacillus* host cell according to the invention is a marker-free host cell, preferably a marker-free host cell comprising one or more single lox sites in the genome, more preferably a marker-free host cell comprising one or more lox72 sites in the genome.

Those skilled in the art know how to produce marker-free host cells using a Cre-lox system.

The procedures used to ligate the elements described above to construct the recombinant expression vectors of the present invention are well known to those skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley InterScience, NY, 1995).

Furthermore, standard molecular cloning techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

The person skilled in the art knows how to transform cells with the one or more expression vectors and the selectable marker.

In the context of the present invention a *Bacillus* host cell as defined herein or a parent of said host cell may be any type of *Bacillus* host cell and includes all species within the genus *Bacillus* as known to those skilled in the art, including but not limited to *B. agaradherens, B. alkalophilus, B. amyloliquefaciens, B. anthracis, B. atrophaeus, B. brevis, B. cereus, B. circulans, B. clausii, B. coagulans, B. firmus, B. halodurans, B. lautus, B. lentus, B. licheniformis, B. megaterium, B. mojavensis, B. pumilus, B. puntis, B. sphaericus, B. stearothermophilus, B. subtilis, B. thuringiensis, B. vallismortis*. It is recognized that the genus *Bacillus* continues to undergo taxonomical reorganization. Thus it is intended that the genus includes species which have been reclassified, including but not limited to such organisms as *B. stearothermoplilus*, which is now named *Geobacillus stearothermophilus*.

In one embodiment the *Bacillus* host cell according to the invention belongs to a species selected from the group consisting of *B. agaradherens, B. alkalophilus, B. amyloliquefaciens, B. anthracis, B. atrophaeus, B. brevis, B. cereus, B. circulans, B. clausii, B. coagulans, B. firmus, B. halodurans, B. lautus, B. lentus, B. licheniformis, B. megaterium, B. mojavensis, B. pumilus, B. puntis, B. sphaericus, B. stearothermophilus, B. subtilis, B. thuringiensis, B. vallismortis*, more preferably belongs to *B. subtilis, B. amyloliquefaciens*, or *Bacillus licheniformis*. Most preferably the *Bacillus* host cell is a *B. subtilis* host cell.

In a preferred embodiment of the invention the *Bacillus* host cell according to the invention is a *Bacillus subtilis* host cell deficient in the production of neutral protease and in the production of alkaline protease, preferably wherein the neutral protease has an amino acid sequence according to SEQ ID NO: 8 or according to an amino acid sequence at least 60% identical to SEQ ID NO: 8, preferably an amino acid sequence at least 65%, 70%, 75%, 80%, 85%, 90%, 95%, 96%, 97%, 98%, 99% identical to SEQ ID NO: 8, and wherein the alkaline protease has an amino acid sequence according to SEQ ID NO: 6 or according to an amino acid sequence at least 60% identical to SEQ ID NO: 6, preferably an amino acid sequence at least 65%, 70%, 75%, 80%, 85%, 90%, 95%, 96%, 97%, 98%, 99% identical to SEQ ID NO: 6. Preferably the *Bacillus subtilis* host cell is further deficient in the production of neutral amylase, preferably wherein the neutral amylase has an amino acid sequence according to SEQ ID NO: 20 or according to an amino acid sequence at least 60% identical to SEQ ID NO: 20, preferably an amino acid sequence at least 65%, 70%, 75%, 80%, 85%, 90%, 95%, 96%, 97%, 98%, 99% identical to SEQ ID NO: 20.

In another embodiment the *Bacillus* host cell according to the invention is a *Bacillus amyloliquefaciens* host cell deficient in the production of neutral protease and in the production of alkaline protease, preferably wherein the neutral protease has an amino acid sequence according to SEQ ID NO: 43 or according to an amino acid sequence at least 60% identical to SEQ ID NO: 43, preferably an amino acid sequence at least 65%, 70%, 75%, 80%, 85%, 90%, 95%, 96%, 97%, 98%, 99% identical to SEQ ID NO: 43 and wherein the alkaline protease has an amino acid sequence according to SEQ ID NO: 45 or according to an amino acid sequence at least 60% identical to SEQ ID NO: 45, preferably an amino acid sequence at least 65%, 70%, 75%, 80%, 85%, 90%, 95%, 96%, 97%, 98%, 99% identical to SEQ ID NO: 45. Preferably the *Bacillus amyloliquefaciens* host cell is further deficient in the production of neutral amylase, preferably wherein the neutral amylase has an amino acid sequence according to SEQ ID NO: 57 or according to an amino acid sequence at least 60% identical to SEQ ID NO: 57, preferably an amino acid sequence at least 65%, 70%, 75%, 80%, 85%, 90%, 95%, 96%, 97%, 98%, 99% identical to SEQ ID NO: 57.

In yet another embodiment the *Bacillus* host cell according to the invention is a *Bacillus licheniformis* host cell deficient in the production of alkaline protease, preferably wherein the alkaline protease has an amino acid sequence according to SEQ ID NO: 47 or according to an amino acid sequence at least 60% identical to SEQ ID NO: 47, preferably an amino acid sequence at least 65%, 70%, 75%, 80%, 85%, 90%, 95%, 96%, 97%, 98%, 99% identical to SEQ ID NO: 47. Preferably the *Bacillus licheniformis* host cell is further deficient in the production of neutral amylase, preferably wherein the neutral amylase has an amino acid sequence according to SEQ ID NO: 59 or according to an amino acid sequence at least 60% identical to SEQ ID NO: 59, preferably an amino acid sequence at least 65%, 70%, 75%, 80%, 85%, 90%, 95%, 96%, 97%, 98%, 99% identical to SEQ ID NO: 59.

The host cell may additionally be deficient in the production of other compounds which are detrimental to the production of the compound of interest or a compound involved in the synthesis of the compound of interest, or detrimental to the recovery and/or application of the compound of interest, e.g. a compound of interest being a polypeptide, e.g. an enzyme. In a preferred aspect the *Bacillus* host cell is a protease deficient host cell. In another preferred aspect the *Bacillus* host cell is further deficient in one or more proteases coded by the genes selected from the group consisting of: nprB, vpr, epr, wprA, mpr, bpr.

In another preferred aspect the *Bacillus* host cell does not produce spores, preferably it is deficient in a sporulation related gene, more preferably it is deficient in a gene selected from the group consisting of spo0A, spoIISA, spoIIAC, sigE, sigF, spoIISB, spoIIE, sigG, spoIVCB, spoIIIC, spoIIGA, spoIIAA, spoIVFB, spoIIR, spoIIIJ. In a preferred embodiment the *Bacillus* host cell is deficient in a spoIIAC gene. In another preferred embodiment the *Bacillus* host cell is deficient in a spoIIE gene, preferably a gene with a polynucleotide sequence according to SEQ ID NO: 39 or with a polynucleotide sequence at least 60% identical to SEQ ID NO: 39, preferably a polynucleotide sequence at least 65%, 70%, 75%, 80%, 85%, 90%, 95%, 96%, 97%, 98%, 99% identical to SEQ ID NO: 39. Preferably the spoIIE gene codes for a polypeptide with an amino acid sequence according to SEQ ID NO: 40 or an amino acid sequence at least 60% identical to SEQ ID NO: 40, preferably an amino acid sequence at least 65%, 70%, 75%, 80%, 85%, 90%, 95%, 96%, 97%, 98%, 99% identical to SEQ ID NO: 40.

Microorganisms which can be used for the present invention may be publicly available from different sources, e.g., Deutsche Sammlung von Mikroorganismen and Zeilkulturen (DSMZ), Inhoffenstrasse 7B, D-38124 Braunschweig, Germany, American Type Culture Collection (ATCC), P.O, Box 1549, Manassas, Va. 20108 USA, Agricultural Research Culture Collection (NRRL), Peoria, Ill., USA, Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Juso-honmachi 2-chome, Yodogawa-ku, Osaka 532-8686, Japan) or the *Bacillus* Genetic Stock Center (BGSC), The Ohio State University, Columbus, Ohio 43210 USA.

In a more preferred embodiment the *Bacillus* host cell is *Bacillus subtilis* BS154, *Bacillus subtilis* 168, *Bacillus subtilis* CBS136327 or a derivatives thereof.

The *Bacillus* host cells according to the invention may be recombinant host cells. The term "recombinant" when used in reference to a host cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant) form of the cell or express native genes that are otherwise abnormally expressed, under expressed or not expressed at all. The term "recombinant" is synonymous with "genetically modified".

In another aspect the invention relates to a method of producing a recombinant *Bacillus* host cell according to the invention comprising:
  a. providing a *Bacillus* host cell deficient in the production of a neutral protease and/or in the production of an alkaline protease, optionally deficient in the production of a neutral α-amylase, optionally deficient in a sporulation-related gene;
  b. transforming the *Bacillus* host cell with a nucleic acid construct comprising a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.

Within this context it will be clear to those skilled in the art that embodiments applicable to the recombinant *Bacillus* host cell according to the invention may also be applicable to other aspects of the invention.

In step a. the method of producing a *Bacillus* host cell according to the invention comprises providing a *Bacillus* host cell deficient in the production of a neutral protease and in the production of an alkaline protease, optionally deficient in the production of a neutral α-amylase, optionally deficient in a sporulation-related gene.

In one embodiment the *Bacillus* host cell in step a. is deficient in the production of a neutral protease and/or in the production of an alkaline protease, and in a sporulation-related gene.

In another embodiment the *Bacillus* host cell in step a. is deficient in the production of a neutral protease and/or in the production of an alkaline protease, and in the production of a neutral α-amylase.

In yet another embodiment the *Bacillus* host cell in step a. is deficient in the production of a neutral protease and/or in the production of an alkaline protease, in the production of a neutral α-amylase, and deficient in a sporulation-related gene.

In yet another embodiment the *Bacillus* host cell in step a. is deficient in the production of a neutral protease and in the production of an alkaline protease, in the production of a neutral α-amylase, and deficient in a sporulation-related gene.

The *Bacillus* host cell may be a *Bacillus* host cell as defined herein.

In one embodiment of the invention step a) comprises providing a parent *Bacillus* host cell and modifying the parent host cell to make it deficient in the production of a neutral protease and/or of an alkaline protease, optionally deficient in a sporulation-related gene, optionally deficient in the production of a neutral α-amylase.

Provision of a *Bacillus* host cell deficient in the production of a neutral protease and of an alkaline protease, optionally deficient in a sporulation-related gene, optionally deficient in the production of a neutral α-amylase in step a) of the invention may be performed with methods known to those skilled in the art.

The deficiency in the host cell may be performed starting from a parent host cell which parent host cell is not deficient by modifying said parent host cell, preferably in its genome, to result in a phenotypic feature wherein the cell: a) produces less or no neutral protease and/or less or no alkaline protease, optionally produces less or no neutral α-amylase, optionally produces less or no compound coded by a sporulation-related gene and/or b) produces a neutral protease, an alkaline protease, optionally a neutral α-amylase and optionally a compound coded by a sporulation-related gene which has less or substantially no (biological or enzymatic) activity or substantially no specific (biological or enzymatic) activity and combinations of one or more of these possibilities as compared to the parent host cell that has not been modified, when analysed under the same conditions. A modification, preferably in the genome, is construed as one or more modifications. The modification, preferably in the genome, can either be effected by
 a) subjecting the parent host cell to recombinant genetic manipulation techniques; and/or
 b) subjecting the parent host cell to (classical) mutagenesis; and/or
 c) subjecting the parent host cell to an inhibiting compound or composition.

Modification of a genome of a host cell is herein defined as any event resulting in a change in a polynucleotide sequence in the genome of the cell. In a preferred embodiment the *Bacillus* host cell deficient in the production of a neutral protease and in the production of the alkaline protease, optionally deficient in the production of a neutral α-amylase, optionally deficient in a sporulation-related gene as herein defined is a host cell having a modification, preferably in its genome comprising:
 a) a modification which results in substantially no production of neutral protease and/or no production of alkaline protease, optionally no production of neutral α-amylase, optionally no production of a compound coded by a sporulation-related gene as defined herein if compared to the parent host cell that has not been modified, when analysed under the same conditions and/or
 b) a modification which results in a neutral protease and/or in an alkaline protease, optionally in a neutral α-amylase, optionally in a compound coded by a sporulation-related gene as defined herein with substantially no (enzymatic or biological) activity as defined herein if compared to the parent host cell that has not been modified, when analysed under the same conditions.

Modification can be introduced by classical strain improvement, random mutagenesis followed by selection. Modification can also be introduced by site-directed mutagenesis.

Modification may be accomplished by the insertion (introduction), substitution (replacement) or deletion (removal) of one or more nucleotides in a polynucleotide sequence. A full or partial deletion of the gene coding for neutral protease, and/or of the gene coding for alkaline protease, optionally of the gene coding for neutral α-amylase, optionally of a sporulation-related gene as defined herein may be achieved. The gene coding for neutral protease, and/or the gene coding for alkaline protease, optionally the gene coding for neutral α-amylase, optionally the sporulation-related gene as defined herein may be partially or fully replaced with a polynucleotide sequence which does not code for the for neutral protease, and/or for the gene coding for alkaline protease, optionally for the gene coding for neutral α-amylase, optionally for a sporulation-related gene or which code for a partially or fully inactive form of the neutral protease, and/or of the alkaline protease, optionally of the neutral α-amylase, optionally of the compound coded by a sporulation-related gene as defined herein. In yet another alternative one or more nucleotides can be inserted into the gene coding for neutral protease, and/or the gene coding for alkaline protease, optionally the gene coding for neutral α-amylase, optionally in the compound coded by a sporulation-related gene as defined herein resulting in the disruption of said gene and consequent partial of full inactivation of the polypeptide or compound coded by said gene.

In one embodiment the *Bacillus* host cell deficient in the production of a neutral protease and/or in the production of an alkaline protease, optionally deficient in the production of a neutral α-amylase, optionally deficient in a sporulation-related gene as defined herein comprises a modification in its genome selected from
 a) a full or partial deletion of the gene coding for neutral protease, and/or of the gene coding for alkaline protease, optionally of the gene coding for neutral α-amylase, optionally of the sporulation-related gene,
 b) a full or partial substitution of the gene coding for neutral protease, and/or of the gene coding for alkaline protease, optionally of the gene coding for neutral α-amylase, optionally of the sporulation-related gene with a polynucleotide sequence which does not code for neutral protease, and/or which does not code for alkaline protease, optionally of the gene coding for neutral α-amylase, optionally of the sporulation-related gene as defined herein or which codes for a partially or fully inactive form of the corresponding polypeptide or compound as defined herein c) a disruption of the gene coding for neutral protease, and/or of the gene coding for alkaline protease, optionally of the gene coding for neutral α-amylase, optionally of the sporulation-related gene as defined herein by the insertion of one or more nucleotides in the polynucleotide sequence of said gene and consequent partial or full inactivation of the corresponding polypeptide as defined herein coded by the disrupted polynucleotide.

This modification may for example be in a coding sequence or a regulatory element required for the transcription or translation of the essential gene. For example, nucleotides may be inserted or removed so as to result in the introduction of a stop codon, the removal of a start codon or a change or a frame-shift of the open reading frame of a coding sequence. The modification of a coding sequence or a regulatory element thereof may be accomplished by site-directed or random mutagenesis, DNA shuffling methods, DNA reassembly methods, gene synthesis (see for example Young and Dong, (2004), *Nucleic Acids Research* 32, (7) electronic access http://nar.oupjournals.org/cgi/reprint/32/7/e59 or Gupta et al. (1968), *Proc. Natl. Acad. Sci USA*, 60: 1338-1344; Scarpulla et al. (1982), *Anal. Biochem.* 121: 356-365; Stemmer et al. (1995), *Gene* 164: 49-53), or PCR generated mutagenesis in accordance with methods known in the art. Examples of random mutagenesis procedures are well known in the art, such as for example chemical (NTG for example) mutagenesis or physical (UV for example) mutagenesis. Examples of site-directed mutagenesis procedures are the QuickChange™ site-directed mutagenesis kit (Stratagene Cloning Systems, La Jolla, Calif.), the 'The Altered Sites® II in vitro Mutagenesis Systems' (Promega Corporation) or by overlap extension using PCR as described in Gene. 1989 Apr 15; 77(1):51-9. (Ho S N, Hunt H D, Horton R M, Pullen J K, Pease L R "Site-directed mutagenesis by overlap extension using the polymerase chain reaction") or using PCR as described in *Molecular Biology: Current Innovations and Future Trends*. (Eds. A. M. Griffin and H. G. Griffin. ISBN 1-898486-01-8; 1995 Horizon Scientific Press, PO Box 1, Wymondham, Norfolk, U.K.).

Preferred methods of modification are based on recombinant genetic manipulation techniques such as partial or complete gene substitution or partial or complete gene deletion.

For example, in case of substitution of a polynucleotide, nucleic acid construct or expression cassette, an appropriate DNA sequence may be introduced at the target locus to be replaced. The appropriate DNA sequence is preferably present on a cloning vector. Preferred integrative cloning vectors comprise a DNA fragment, which is homologous to the polynucleotide and/or has homology to the polynucleotides flanking the locus to be replaced for targeting the integration of the cloning vector to this pre-determined locus. In order to promote targeted integration, the cloning vector is preferably linearized prior to transformation of the cell. Preferably, linearization is performed such that at least one but preferably either end of the cloning vector is flanked by sequences homologous to the DNA sequence (or flanking sequences) to be replaced. This process is called homologous recombination and this technique may also be used in order to achieve (partial) gene deletion.

For example, the gene coding for a relevant compound (e.g. neutral protease, alkaline protease, neutral α-amylase, a compound coded by the sporulation-related gene) may be replaced by a defective polynucleotide, that is a polynucleotide that fails to produce a (fully functional) relevant compound. By homologous recombination, the defective polynucleotide replaces the endogenous polynucleotide. It may be desirable that the defective polynucleotide also encodes a marker, which may be used for selection of transformants in which the nucleic acid sequence has been modified.

Alternatively, modification, wherein said host cell produces no or less neutral protease, no or less alkaline protease, optionally no or less neutral α-amylase, optionally no or less compound coded by the sporulation-related gene as defined herein, may be performed by established anti-sense techniques using a nucleotide sequence complementary to the nucleic acid sequence of the relevant gene. More specifically, expression of the gene by a host cell may be reduced or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

In one embodiment the provision of a *Bacillus* host cell deficient in the production of a neutral protease and/or in the production of an alkaline protease, optionally deficient in the production of a neutral α-amylase, optionally deficient in a compound coded by a sporulation-related gene can be achieved by eliminating production of the mRNA encoding said polypeptide if compared with a parent host cell which is not deficient and measured under the same conditions. In another embodiment the host cell is inducibly deficient the production of a neutral protease and/or in the production of an alkaline protease, optionally deficient in the production of a neutral α-amylase, optionally deficient in a sporulation-related gene. The provision of a host cell inducibly deficient the production of a neutral protease and/or in the production of an alkaline protease, optionally deficient in the production of a neutral α-amylase, optionally deficient in a sporulation-related gene can be achieved by placing the corresponding gene in the host genome under the control of an inducible promoter. The inducible promoter may be any inducible promoter suitable for the purpose, be it a chemically or physically induced promoter (such as by temperature or light). The person skilled in the art knows how to select such promoter. Suitable promoters from Gram-positive microorganisms include, but are not limited to, gnt (gluconate operon promoter); penP from *Bacillus licheniformis*; glnA (glutamine synthetase); xylAB (xylose operon); araABD (L-arabinose operon) and $P_{spac}$ promoter. Other examples are promoters activated by sporulation specific sigma factors: $\sigma^F$, $\sigma^E$, $\sigma^G$ and $\sigma^K$ and general stress sigma factor, σB. Yet other promoters from Gram-positive microorganisms include, but are not limited to, trp operon and sacB gene.

A modification which results in no amount of the mRNA transcribed from the relevant gene as described herein may be obtained via the RNA interference (RNAi) technique (FEMS Microb. Lett. 237 (2004): 317-324). In this method identical sense and antisense parts of the nucleotide sequence, which expression is to be affected, are cloned behind each other with a nucleotide spacer in between, and inserted into an expression vector. After such a molecule is transcribed, formation of small nucleotide fragments will lead to a targeted degradation of the mRNA, which is to be affected. The elimination of the specific mRNA can be to various extents. A modification which results in a neutral protease and/or in a alkaline protease, optionally in a neutral α-amylase, optionally in a compound coded by a sporulation-related gene with less or no (enzymatic or biological) activity as defined herein can be obtained by different methods, for example by an antibody directed against such a polypeptide or a chemical inhibitor or a protein inhibitor or a physical inhibitor (Tour O. et al, (2003) Nat. Biotech: Genetically targeted chromophore-assisted light inactivation. Vol. 21. no. 12:1505-1508) or peptide inhibitor or an anti-sense molecule or RNAi molecule (R. S. Kamath_et al, (2003) Nature: Systematic functional analysis of the *Caenorhabditis elegans* genome using RNAi. vol. 421, 231-237).

In addition of the above-mentioned techniques or as an alternative, it is also possible to inhibiting the activity of the neutral protease and/or of an alkaline protease, optionally of a neutral α-amylase, optionally of a compound coded by a sporulation-related gene as defined herein, or to re-localize the corresponding polypeptide as defined herein by means of alternative signal sequences.

Alternatively or in combination with above-mentioned techniques, inhibition of polypeptide enzymatic activity as defined herein can also be obtained, e.g. by UV or chemical mutagenesis or by the use of inhibitors inhibiting enzymatic activity of a polypeptide as described herein (e.g. nojirimycin, which function as inhibitor for β-glucosidases (Carrel F.L.Y. and Canevascini G. *Canadian Journal of Microbiology* (1991) 37(6): 459-464; Reese E. T., Parrish F. W. and Ettlinger M. *Carbohydrate Research* (1971) 381-388)).

In one embodiment of the method of producing a *Bacillus* host cell according to the invention, the parent host cell is modified in its genome by one of the following methods: a) partially or fully deleting a gene; b) partially or fully replacing a gene with a polynucleotide sequence; c) disrupting the gene by insertion of one or more nucleotides in the polynucleotide sequence of said gene; d) placing a gene in the host cell genome under the control of an inducible promoter and culturing the host cell under conditions which repress transcription of the gene into mRNA, wherein the gene is a gene coding for neutral protease and/or a gene coding for alkaline protease, optionally a gene coding for neutral α-amylase, optionally a sporulation-related gene, wherein the host cell i) produce no product encoded by the gene or ii) produce a product with no (biological or enzymatic) activity or a combination of i) and ii).

In step b. of the method of producing a *Bacillus* host cell according to the invention the *Bacillus* host cell is transformed with a nucleic acid construct comprising a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence. The *Bacillus* host cell, the nucleic acid construct, the polynucleotide encoding a compound of interest or encoding a compound involved in the synthesis of a compound of interest, the promoter comprising a bacteriophage promoter sequence, more preferably a bacteriophage SPO1 promoter sequence have been herein described.

The nucleic acid construct can be introduced into *Bacillus* host cells via natural competence, conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook & Russell, *Molecular Cloning: A Laboratory Manual*, 3rd Ed., CSHL Press, Cold Spring Harbor, N.Y., 2001, and other laboratory manuals and are well known to those skilled in the art. Those of skilled in the art know how to introduce polynucleotide sequences into *Bacillus* cells (See e.g., Ferrari et al., "Genetics," Harwood et al. (ed.), *Bacillus*, Plenum Publishing Corp. (1989) pages 57-72; Saunders et al., J. Bacteriol, 157:718-726 (1984); Hoch et al., J. Bacteriol, 93:1925-1937 (1967); Mann et al., Current Microbiol, 13:131-135 (1986); and Holubova, Folia Microbiol, 30:97 (1985); for *B. subtilis*, Chang et al., *Mol. Gen. Genet.*, 168:11-115 (1979); for *B. megaterium*, Vorobjeva et al., FEMS Microbiol Lett., 7:261-263 [1980]; for *B amyloliquefaciens*, Smith et al., Appl Env. Microbiol, 51:634 (1986); for *B. thuringiensis*, Fisher et al., Arch. Microbiol, 139:213-217 (1981); and for *B. sphaericus*, McDonald, J. Gen. Microbiol, 130:203 (1984)). Such methods include protoplast transformation and congression, transduction, and protoplast fusion. Methods of transformation are particularly preferred to introduce a nucleic acid construct provided by the present invention into a host cell. Introduction of the nucleic acid construct into the host cell includes those physical and chemical methods known in the art to introduce DNA into a host cell without insertion into a plasmid or vector. Such methods include, but are not limited to calcium chloride precipitation, electroporation, naked DNA, liposomes and the like. In additional embodiments, DNA constructs are co-transformed with a plasmid, without being inserted into the plasmid.

In order to enhance the amount of copies of the polynucleotide coding for the compound of interest or coding for a compound involved in the production of the compound of interest in the *Bacillus* host cell, multiple transformations of the host cell may be required. In this way, the ratios of the different enzymes produced by the host cell may be influenced. Also, a nucleic acid construct may comprise multiple expression cassettes to increase the amount of copies of the polynucleotide(s) to be transformed.

Another way could be to choose different control sequences for the different polynucleotides, which—depending on the choice—may cause a higher or a lower production of the desired polypeptide(s).

The cells transformed with the selectable marker can be selected based on the presence of the selectable marker. In further embodiments, a selectable marker is deleted from the altered *Bacillus* strain by methods known in the art (See, Stahl et al., (1984) J. Bacteriol., 158:411-418; and Palmeros et al, (2000) Gene 247:255-264).

In a further aspect the invention provides a method for the production of a compound of interest comprising
  a) culturing a recombinant *Bacillus* host cell according to the invention or a recombinant *Bacillus* host cell produced according to the method of producing a recombinant *Bacillus* host cell according to the invention, under conditions conducive to the production of the compound of interest, and
  b) optionally isolating the compound of interest from the culture broth.

The compound of interest may be any compound of interest as herein defined.

The recombinant *Bacillus* host cell deficient in the production of a neutral protease and/or of an alkaline protease comprising a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence, has been herein described. All embodiments of said host cell as herein described are equally applicable to the method for the production of a compound of interest as described herein.

Step a) of the method of production of a compound of interest according to the invention comprises culturing the recombinant *Bacillus* host cell deficient in the production of a neutral protease and/or of an alkaline protease, wherein said host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence, under conditions conducive to the production of the compound of interest. The host cells may be cultivated in a nutrient medium suitable for production of the compound of interest using methods known in the art. For example, the cells may be cultivated by shake flask cultivation, small-scale or large-scale fermentation (including continuous, batch, fed-batch, or solid state fermentations) in laboratory or industrial fermenters performed in a suitable medium and under conditions allowing the compound of interest to be produced and/or isolated. The cultivation takes place in a suitable nutrient medium comprising carbon and nitrogen sources and inorganic salts, using procedures known in the art. Suitable media are available from commercial suppliers or may be prepared using published compositions (e. g., in catalogues of the American Type Culture Collection). If the compound of interest is secreted into the nutrient medium, the compound can be isolated directly from the medium. If the compound of interest is not secreted, it can be isolated from cell lysates.

In one embodiment the method of production of a compound of interest according to the invention may comprise prior to step a) providing a recombinant *Bacillus* host cell deficient in the production of a neutral protease and/or of an alkaline protease which host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence, as defined herein. Methods to produce the *Bacillus* host cell may be those herein described.

Step b) of the method of production of a compound of interest according to the invention may comprise isolating the compound of interest from the culture broth. The compound of interest as described herein may be isolated by methods known in the art.

For example, the compound of interest may be isolated from the nutrient medium by conventional procedures including, but not limited to, centrifugation, filtration, extraction, spray drying, evaporation, or precipitation. The isolated compound of interest may then be further purified by a variety of procedures known in the art including, but not limited to, chromatography (e. g., ion exchange, affinity, hydrophobic, chromatofocusing, and size exclusion), electrophoretic procedures (e.g., preparative isoelectric focusing), differential solubility (e. g., ammonium sulfate precipitation), or extraction (see, e.g., Protein Purification, J.-C. Janson and Lars Ryden, editors, VCH Publishers, New York, 1989). In some applications the compound of interest may be used without substantial isolation from the culture broth; separation of the culture medium from the biomass may be adequate.

In preferred embodiment of the method for the production of a compound of interest according to the invention, the yield of the compound of interest is improved if compared to a method wherein a second host cell is used, wherein said second host cell differs from the host cell only in that the nucleic acid construct comprises a different promoter and/or the *Bacillus* host cell is not deficient in the production of a neutral protease and/or of a alkaline protease as defined herein, wherein the two methods are performed under the same conditions.

Preferably the yield increases with at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90% or at least 100%, more preferably, with at least 110%, at least 120%, at least 130%, at least 140%, at least 150%, at least 160%, at least 170%, at least 180%, at least 190% or at least 200%, even more preferably with at least 210%, at least 220%, at least 230%, at least 240%, at least 250%, at least 260%, at least 270%, at least 280%, at least 290% or at least 300%.

In a further embodiment, the invention provides the use of a recombinant *Bacillus* host cell deficient in the production of a neutral protease and/or of an alkaline protease comprising a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence according to the invention, in a method for producing a compound of interest.

Embodiments of the Invention

1. A recombinant *Bacillus* host cell deficient in the production of a neutral protease and/or of an alkaline protease which host cell comprises a nucleic acid construct, wherein the nucleic acid construct comprises
   a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.
2. A host cell according to embodiment 1 wherein the bacteriophage SPO1promoter sequence comprises a polynucleotide sequence according to SEQ ID NO: 36 or a polynucleotide sequence at least 70% identical to SEQ ID NO: 36.
3. A host cell according to embodiment 1 or 2 wherein the bacteriophage SPO1promoter is a polynucleotide sequence according to SEQ ID NO: 1 or a polynucleotide sequence at least 70% identical to SEQ ID NO: 1, preferably the bacteriophage SPO1promoter is a PE4 or PE5, more preferably a promoter according to SEQ ID NO: 1 or SEQ ID NO: 2.

4. A host cell according to any one of embodiments 1 to 3 wherein the bacteriophage SPO1promoter sequence is part of an expression module comprising the promoter, a sequence coding for a Ribosome Binding Site (RBS) and optionally a mRNA stabilizing element and/or or a modified rib leader.

5. A host cell according to embodiment 4 wherein the expression module comprises the bacteriophage SPO1promoter, a mRNA stabilizing element and/or a modified rib leader and a sequence coding for a RBS, more preferably the expression module comprises a mRNA stabilizing element and/or modified rib leader located downstream of the promoter and upstream of a sequence coding for a RBS.

6. A host cell according to embodiment 5 wherein the mRNA stabilizing element is selected from aprE, grpE, cotG, SP82, RSBgsiB, CryIIIA mRNA stabilizing elements, preferably mRNA stabilizing elements according to SEQ ID NO: 48 to 54, more preferably a grpE mRNA stabilizing element, even more preferably a mRNA stabilizing element according to SEQ ID NO: 49.

7. A host cell according to embodiment 5 or 6 wherein the modified rib leader is a rib leader comprising the ribO mutation C85T, even more preferably it is a rib leader according to SEQ ID NO: 55 comprising the ribO mutation C85T, even more preferably a rib leader according to SEQ ID NO: 55 comprising the ribO mutation C85T in the corresponding position of SEQ ID NO: 55 and a deletion of nucleotides corresponding to nucleotides 166 to 263 of SEQ ID NO:55.

8. A host cell according to any one of embodiments 4 to 7 wherein the sequence coding for a RBS is selected from a sequence coding for a 16S RBS and a sequence coding for a ribD RBS.

9. A host cell according to any one of embodiments 1 to 8 wherein the expression module has a polynucleotide sequence selected from SEQ ID NO: 13, SEQ ID NO: 14, SEQ ID NO: 15, SEQ ID NO: 16, SEQ ID NO: 31, SEQ ID NO: 32, SEQ ID NO: 33, SEQ ID NO: 34, SEQ ID NO: 35.

10. A host cell according to any one of embodiments 1 to 9 wherein the neutral protease is a neutral protease encoded by a npr gene, preferably the neutral protease is encoded by a polynucleotide sequence according to SEQ ID NO: 7 or SEQ ID NO: 42 or a by a polynucleotide sequence at least 70% identical to SEQ ID NO: 7 or SEQ ID NO: 42, preferably wherein the neutral protease is encoded by a polynucleotide sequence according to SEQ ID NO: 7 or a by a polynucleotide sequence at least 70% identical to SEQ ID NO: 7.

11. A host cell according to any one of embodiments 1 to 10 wherein the neutral protease has an amino acid sequence according to SEQ ID NO: 8 or SEQ ID NO: 43 or an amino acid sequence at least 70% identical to SEQ ID NO: 8 or SEQ ID NO: 43, preferably wherein the neutral protease has an amino acid sequence according to SEQ ID NO: 8 or an amino acid sequence at least 70% identical to SEQ ID NO: 8.

12. A host cell according to any one of embodiments 1 to 11 wherein the alkaline protease is an alkaline protease encoded by a apr gene, preferably an alkaline protease encoded by a polynucleotide sequence according to SEQ ID NO: 5, SEQ ID NO: 44 or SEQ ID NO: 46 or a polynucleotide sequence at least 70% identical to SEQ ID NO: 5, SEQ ID NO: 44 or SEQ ID NO: 46, preferably an alkaline protease encoded by a polynucleotide sequence according to SEQ ID NO: 5 or a polynucleotide sequence at least 70% identical to SEQ ID NO: 5.

13. A host cell according to any one of embodiments 1 to 12 wherein the alkaline protease has an amino acid sequence according to SEQ ID NO: 6, SEQ ID NO: 45 or SEQ ID NO: 47 or an amino acid sequence at least 70% identical to SEQ ID NO: 6, SEQ ID NO: 45 or SEQ ID NO: 47, preferably wherein the alkaline protease has an amino acid sequence according to SEQ ID NO: 6 or an amino acid sequence at least 70% identical to SEQ ID NO: 6.

14. A host cell according to any one of embodiments 1 to 13 which belongs to a species selected from the group consisting of: *B. agaradherens, B. alkalophilus, B. amyloliquefaciens, B. anthracis, B. atrophaeus, B. brevis, B. cereus, B. circulans, B. clausii, B. coagulans, B. firmus, B. halodurans, B. lautus, B. lentus, B. licheniformis, B. megaterium, B. mojavensis, B. pumilus, B. puntis, B. sphaericus, B. stearothermophilus, B. subtilis, B. thuringiensis, B. vallismortis*, more preferably which belongs to *B. subtilis* or *B. amyloliquefaciens*, most preferably a host cell which is a *B. subtilis* host cell.

15. A host cell according to any one of embodiments 1 to 14 which does not produce spores, preferably a host cell which is deficient in a sporulation-related gene, preferably deficient in a gene selected from the group consisting of spo0A, spoIISA, spoIIAC, sigE, sigF, spoIISB, spoIIE, sigG, spoIVCB, spoIIIC, spoIIGA, spoIIAA, spoIVFB, spoIIR, spoIII, preferably deficient in a spoIIE or deficient in a spoIIAC gene.

16. A host cell according to any one of embodiments 1 to 15 which is further deficient in the production of a neutral α-amylase, preferably a host cell which is deficient in the production of a neutral α-amylase encoded by a amyE gene, even more preferably a host cell which is deficient in neutral α-amylase encoded by a polynucleotide according to SEQ ID NO: 19, SEQ ID NO: 56 or SEQ ID NO: 58 or a polynucleotide at least 70% identical to SEQ ID NO: 19, SEQ ID NO: 56 or SEQ ID NO: 58, more preferably neutral α-amylase encoded by a polynucleotide according to SEQ ID NO: 19 or a polynucleotide at least 70% identical to SEQ ID NO: 19.

17. A host cell according to any one of embodiments 1 to 16 which is further deficient in the production of an α-amylase having an amino acid sequence according to SEQ ID NO: 20, SEQ ID NO: 57 or SEQ ID NO: 59 or an amino acid sequence at least 70% identical to SEQ ID NO: 20, SEQ ID NO: 57 or SEQ ID NO: 59, even more preferably an α-amylase having an amino acid sequence according to SEQ ID NO: 20 or an amino acid sequence at least 70% identical to SEQ ID NO: 20.

18. A host cell according to any one of embodiments 1 to 17 wherein the nucleic acid construct is integrated into the host cell genome, preferably it is integrated into a locus selected from the nprE locus, the amyE locus or the aprE locus, more preferably the amyE locus.

19. A host cell according to any one of embodiments 1 to 18 comprising more than one copy of the nucleic acid construct, more preferably it comprises more than one copy of the nucleic acid construct integrated into the host cell genome.

20. A host cell according to any one of embodiments 1 to 19 wherein the compound of interest is a biopolymer selected from a nucleic acid, polyamine, polyol, polypeptide (or polyamide), or polysaccharide, preferably the polypeptide may be an enzyme.

21. A host cell according to any one of embodiments 1 to 20 wherein one or more nucleic acid constructs comprise a selectable marker located between two lox sites, preferably located between a lox 66 and a lox 71 site.
22. A host cell according to any one of embodiments 1 to 21 which is a marker-free host cell, preferably a marker-free host cell comprising one or more single lox sites in the genome, more preferably a marker-free host cell comprising one or more lox 72 sites in the genome.
23. A host cell according to any one of embodiments 1 to 22 which is a *Bacillus subtilis* host cell deficient in the production of neutral protease and in the production of alkaline protease, preferably wherein the neutral protease has an amino acid sequence according to SEQ ID NO: 8 or according to an amino acid sequence at least 70% identical to SEQ ID NO: 8 and wherein the alkaline protease has an amino acid sequence according to SEQ ID NO: 6 or according to an amino acid sequence at least 70% identical to SEQ ID NO: 6.
24. A host cell according to embodiment 23 wherein the *Bacillus subtilis* host cell is further deficient in the production of neutral amylase, preferably wherein the neutral amylase has an amino acid sequence according to SEQ ID NO: 20 or according to an amino acid sequence at least 70% identical to SEQ ID NO: 20.
25. A host cell according to any one of embodiments 1 to 22 which is a *Bacillus amyloliquefaciens* host cell deficient in the production of neutral protease and in the production of alkaline protease, preferably wherein the neutral protease has an amino acid sequence according to SEQ ID NO: 43 or according to an amino acid sequence at least 70% identical to SEQ ID NO: 43 and wherein the alkaline protease has an amino acid sequence according to SEQ ID NO: 45 or according to an amino acid sequence at least 70% identical to SEQ ID NO: 45.
26. A host cell according to embodiment 25 wherein the *Bacillus amyloliquefaciens* host cell is further deficient in the production of neutral amylase, preferably wherein the neutral amylase has an amino acid sequence according to SEQ ID NO: 57 or according to an amino acid sequence at least 70% identical to SEQ ID NO: 57.
27. A host cell according to any one of embodiments 1 to 22 which is a *Bacillus licheniformis* host cell deficient in the production of alkaline protease, preferably wherein the alkaline protease has an amino acid sequence according to SEQ ID NO: 47 or according to an amino acid sequence at least 70% identical to SEQ ID NO: 47.
28. A host cell according to embodiment 27 wherein the *Bacillus licheniformis* host cell is further deficient in the production of neutral amylase, preferably wherein the neutral amylase has an amino acid sequence according to SEQ ID NO: 59 or according to an amino acid sequence at least 70% identical to SEQ ID NO: 59.
29. Method of producing a recombinant *Bacillus* host cell according to any one of embodiments 1 to 28 comprising:
  a. providing a *Bacillus* host cell deficient in the production of a neutral protease and/or in the production of an alkaline protease, optionally deficient in the production of a neutral α-amylase, optionally deficient in a sporulation-related gene;
  b. transforming the *Bacillus* host cell with a nucleic acid construct comprising a polynucleotide encoding a compound of interest or encoding a compound involved in the synthesis of a compound of interest operably linked to a promoter sequence allowing for expression of the polynucleotide in the host cell, wherein the promoter comprises a bacteriophage promoter sequence, more preferably a bacteriophage SPO1 promoter sequence.
30. A method according to embodiment 29 wherein the *Bacillus* host cell in step a. is deficient in the production of a neutral protease and/or in the production of an alkaline protease, and in a sporulation-related gene.
31. A method according to embodiment 29 wherein the *Bacillus* host cell in step a. is deficient in the production of a neutral protease and/or in the production of an alkaline protease, and in the production of a neutral α-amylase.
32. A method according to embodiment 29 wherein the *Bacillus* host cell in step a. is deficient in the production of a neutral protease and/or in the production of an alkaline protease, in the production of a neutral α-amylase, and in a sporulation-related gene.
33. A method according to embodiment 29 wherein the *Bacillus* host cell in step a. is deficient in the production of a neutral protease and in the production of an alkaline protease, in the production of a neutral α-amylase, and in a sporulation-related gene.
34. A method according to any one of embodiments 29 to 33 wherein step a. is performed by modifying a parent host cell in its genome by one of the following methods: a) partially or fully deleting a gene; b) partially or fully replacing a gene with a polynucleotide sequence; c) disrupting the gene by insertion of one or more nucleotides in the polynucleotide sequence of said gene; d) placing a gene in the host cell genome under the control of an inducible promoter and culturing the host cell under conditions which repress transcription of the gene into mRNA, wherein the gene is a gene coding for neutral protease and/or a gene coding for alkaline protease, optionally a gene coding for neutral α-amylase, optionally a sporulation-related gene, wherein the host cell i) produce no product encoded by the gene or ii) produce a product with no (biological or enzymatic) activity or a combination of i) and ii).
35. A method according to any one of embodiments 29 to 34 wherein the bacteriophage SPO1 promoter sequence comprises a polynucleotide sequence according to SEQ ID NO: 36 or a polynucleotide sequence at least 70% identical to SEQ ID NO: 36.
36. A method according to any one of embodiments 29 to 35 wherein the bacteriophage SPO1 promoter is a polynucleotide sequence according to SEQ ID NO: 1 or a polynucleotide sequence at least 70% identical to SEQ ID NO: 1, preferably the SPO1 bacterial phage promoter is a PE4 or PE5, more preferably a promoter according to SEQ ID NO: 1 or SEQ ID NO: 2.
37. A method according to any one of embodiments 29 to 36 wherein the promoter sequence is part of an expression module comprising the promoter, a sequence coding for a RBS and optionally a mRNA stabilizing element and/or or a modified rib leader.
38. A method according to embodiments 37 wherein the expression module comprises the promoter, a mRNA stabilizing element and/or the modified rib leader and a sequence coding for a RBS, more preferably the expression module comprises a mRNA stabilizing element and/or rib leader located downstream of the promoter and upstream of a sequence coding for a RBS.
39. A method according to embodiment 38 wherein the mRNA stabilizing element is selected from aprE, grpE, cotG, SP82, RSBgsiB, CryIIIA mRNA stabilizing elements, preferably mRNA stabilising elements according to SEQ ID NO: 48 to 54, more preferably a grpE mRNA stabilizing element, even more preferably a mRNA stabilising element according to SEQ ID NO: 49.

40. A method according to embodiment 38 or 39 wherein the modified rib leader is a rib leader comprising the ribO mutation C85T, even more preferably it is a rib leader according to SEQ ID NO: 55 comprising the ribO mutation C85T, even more preferably a rib leader according to SEQ ID NO: 55 comprising the ribO mutation C85T in the corresponding position of SEQ ID NO: 55 and a deletion of nucleotides corresponding to nucleotides 166 to 263 of SEQ ID NO:55.

41. A method according to any one of embodiments 38 to 40 wherein the sequence coding for a RBS is selected from a sequence coding for a 16S RBS and a sequence coding for a ribD RBS.

42. A method according to any one of embodiments 29 to 41 wherein the expression module has a polynucleotide sequence selected from SEQ ID NO: 13, SEQ ID NO: 14, SEQ ID NO: 15, SEQ ID NO: 16, SEQ ID NO: 31, SEQ ID NO: 32, SEQ ID NO: 33, SEQ ID NO: 34, SEQ ID NO: 35.

43. A method according to any one of embodiments 29 to 42 wherein the neutral protease is a neutral protease encoded by a nprE gene, preferably the neutral protease is encoded by a polynucleotide sequence according to SEQ ID NO: 7 or SEQ ID NO: 42 or a by a polynucleotide sequence at least 70% identical to SEQ ID NO: 7 or SEQ ID NO: 42, preferably wherein the neutral protease is encoded by a polynucleotide sequence according to SEQ ID NO: 7 or a by a polynucleotide sequence at least 70% identical to SEQ ID NO: 7.

44. A method according to any one of embodiments 29 to 43 wherein the neutral protease has an amino acid sequence according to SEQ ID NO: 8 or SEQ ID NO: 43 or an amino acid sequence at least 70% identical to SEQ ID NO: 8 or SEQ ID NO: 43, preferably wherein the neutral protease has an amino acid sequence according to SEQ ID NO: 8 or an amino acid sequence at least 70% identical to SEQ ID NO: 8.

45. A method according to any one of embodiments 29 to 44 wherein the alkaline protease is an alkaline protease encoded by a apr gene, preferably an alkaline protease encoded by a polynucleotide sequence according to SEQ ID NO: 5, SEQ ID NO: 44 or SEQ ID NO: 46 or a polynucleotide sequence at least 70% identical to SEQ ID NO: 5, SEQ ID NO: 44 or SEQ ID NO: 46, preferably an alkaline protease encoded by a polynucleotide sequence according to SEQ ID NO: 5 or a polynucleotide sequence at least 70% identical to SEQ ID NO: 5.

46. A method according to any one of embodiments 29 to 45 wherein the alkaline protease has an amino acid sequence according to SEQ ID NO: 6, SEQ ID NO: 45 or SEQ ID NO: 47 or an amino acid sequence at least 70% identical to SEQ ID NO: 6, SEQ ID NO: 45 or SEQ ID NO: 47, preferably wherein the alkaline protease has an amino acid sequence according to SEQ ID NO: 6 or an amino acid sequence at least 70% identical to SEQ ID NO: 6.

47. A method according to any one of embodiments 29 to 46 wherein the host cell belongs to a species selected from the group consisting of: *B. agaradherens, B. alkalophilus, B. amyloliquefaciens, B. anthracis, B. atrophaeus, B. brevis, B. cereus, B. circulans, B. clausii, B. coagulans, B. firmus, B. halodurans, B. lautus, B. lentus, B. licheniformis, B. megaterium, B. mojavensis, B. pumilus, B. puntis, B. sphaericus, B. stearothermophilus, B. subtilis, B. thuringiensis, B. vallismortis*, more preferably which belongs to *B. subtilis* or *B. amyloliquefaciens*, most preferably a host cell which is a *B. subtilis* host cell.

48. A method according to any one of embodiments 29 to 47 wherein the sporulation-related gene is a gene selected from the group consisting of spo0A, spoIISA, spoIIAC, sigE, sigF, spoIISB, spoIIE, sigG, spoIVCB, spoIIIC, spoIIGA, spoIIAA, spoIVFB, spoIIR, spoIII, more preferably deficient in a spoIIE or in a spoIIAC.

49. A method according to any one of embodiments 29 to 48 wherein the neutral α-amylase is encoded by a amyE gene, even more preferably the neutral α-amylase is encoded by a polynucleotide according to SEQ ID NO: 19, SEQ ID NO: 56 or SEQ ID NO: 58 or a polynucleotide at least 70% identical to SEQ ID NO: 19, SEQ ID NO: 56 or SEQ ID NO: 58, more preferably neutral α-amylase encoded by a polynucleotide according to SEQ ID NO: 19 or a polynucleotide at least 70% identical to SEQ ID NO: 19.

50. A method according to any one of embodiments 29 to 49 wherein the α-amylase has an amino acid sequence according to SEQ ID NO: 20, SEQ ID NO: 57 or SEQ ID NO: 59 or an amino acid sequence at least 70% identical to SEQ ID NO: 20, SEQ ID NO: 57 or SEQ ID NO: 59, even more preferably an α-amylase having an amino acid sequence according to SEQ ID NO: 20 or an amino acid sequence at least 70% identical to SEQ ID NO: 20.

51. A method according to any one of embodiments 29 to 50 wherein in step b. the nucleic acid construct is integrated into the host cell genome, preferably it is integrated into a locus selected from the nprE locus, the amyE locus or the aprE locus, more preferably the amyE locus.

52. A method according to any one of embodiments 29 to 51 wherein in step b. the *Bacillus* host cell is transformed with more than one copy of the nucleic acid construct, more preferably more than one copy of the nucleic acid construct are integrated into the host cell genome.

53. A method according to any one of embodiments 29 to 52 wherein the compound of interest is a biopolymer selected from a nucleic acid, polyamine, polyol, polypeptide (or polyamide), or polysaccharide, preferably the polypeptide may be an enzyme.

54. A method according to any one of embodiments 29 to 53 wherein in step b. one or more nucleic acid constructs comprise a selectable marker located between two lox sites, preferably located between a lox 66 and a lox 71 site.

55. A method according to embodiment 54 wherein the method further comprises the steps of
c. selecting the *Bacillus* host cells which have been transformed with the one or more nucleic acid constructs using the selectable marker; and optionally
d. removing the selectable marked by Cre recombinase-mediated recombination of the lox sites, preferably of the lox66 and the lox 71 sites to yield a lox 72 site in the *Bacillus* host cell genome.

56. A method according to any one of embodiments 29 to 55 wherein the *Bacillus* host cell in step a. is a *Bacillus subtilis* host cell deficient in the production of neutral protease and in the production of alkaline protease, preferably wherein the neutral protease has an amino acid sequence according to SEQ ID NO: 8 or according to an amino acid sequence at least 70% identical to SEQ ID NO: 8 and wherein the alkaline protease has an amino acid sequence according to SEQ ID NO: 6 or according to an amino acid sequence at least 70% identical to SEQ ID NO: 6.

57. A method according to embodiment 56 wherein the *Bacillus subtilis* host cell in step a. is further deficient in the production of neutral amylase, preferably wherein the neutral amylase has an amino acid sequence according to SEQ ID NO: 20 or according to an amino acid sequence at least 70% identical to SEQ ID NO: 20.

58. A method according to any one of embodiments 29 to 55 wherein the *Bacillus* host cell in step a. is a *Bacillus amyloliquefaciens* host cell deficient in the production of neutral protease and in the production of alkaline protease, preferably wherein the neutral protease has an amino acid sequence according to SEQ ID NO: 43 or according to an amino acid sequence at least 70% identical to SEQ ID NO: 43 and wherein the alkaline protease has an amino acid sequence according to SEQ ID NO: 45 or according to an amino acid sequence at least 70% identical to SEQ ID NO: 45.

59. A method according to embodiment 58 wherein the *Bacillus amyloliquefaciens* host cell in step a. is further deficient in the production of neutral amylase, preferably wherein the neutral amylase has an amino acid sequence according to SEQ ID NO: 57 or according to an amino acid sequence at least 70% identical to SEQ ID NO: 57.

60. A method according to any one of embodiments 29 to 55 wherein the *Bacillus* host cell in step a. is a *Bacillus licheniformis* host cell deficient in the production of alkaline protease, preferably wherein the alkaline protease has an amino acid sequence according to SEQ ID NO: 47 or according to an amino acid sequence at least 70% identical to SEQ ID NO: 47.

61. A method according to embodiment 60 wherein the *Bacillus licheniformis* host cell in step a. is further deficient in the production of neutral amylase, preferably wherein the neutral amylase has an amino acid sequence according to SEQ ID NO: 59 or according to an amino acid sequence at least 70% identical to SEQ ID NO: 59.

62. Method for the production of a compound of interest comprising
    a) culturing a recombinant *Bacillus* host cell according to any one of embodiments 1 to 28 or a recombinant *Bacillus* host cell produced according to the method for the production of a recombinant *Bacillus* host cell according to any one of embodiments 29 to 61, under conditions conducive to the production of the compound of interest, and
    b) optionally isolating the compound of interest from the culture broth.

63. Use of the recombinant *Bacillus* host cell according to any one of embodiments 1 to 28 or a recombinant *Bacillus* host cell produced according to the method of any one of embodiments 29 to 61, in the production of a compound of interest.

64. The method of embodiment 62 or the use of embodiment 63 wherein the compound of interest is a biopolymer selected from a nucleic acid, polyamine, polyol, polypeptide (or polyamide), or polysaccharide, preferably the polypeptide may be an enzyme.

The present invention is further illustrated by the following Examples which however should not be intended as to be limiting the scope of the invention.

EXAMPLES

It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Materials and Methods
Strain Construction

*Bacillus subtilis* strain BS154 (deposited on 9 Oct. 2013 as CBS136327 at the Centraalbureau voor Schimmelcultures (Fungal Biodiversity Centre), Uppsalalaan 8, 3584CT Utrecht, The Netherlands) (ΔaprE, ΔnprE, amyE$^-$, spo$^-$) is described in Quax and Broekhuizen 1994 Appl. Microbiol. Biotechnol. 41: 425-431. The *E. coli*/*B. subtilis* shuttle vector pBHA12 is described in WO2008/000632.

*Bacillus subtilus* 168 (ATCC 23857) (trpC2) is described in Anagnostopoulos C. and Spizizen J. (1961) J. Bacteriol. (1961) 81(5): 741-746.

*Bacillus stearothermophilus* (which was renamed *Geobacillus stearothermophilus*) C599 (NCIMB11873) is described in WO91/04669.

*Bacillus subtilis* strain 1A40 or BR151 (ATCC 33677) (TrpC2, lys3 and metB10) is described in Young F. E., Smith C., Reilly B. E. (1969) J. Bacteriol. 98:1087-1097.

The promoter PE4 (indicated herewith as P15 promoter) and PE5 of the *B. subtilis* bacteriophage SPO1 are described in Lee et al., 1980, Mol. Gen. Genet. 180: 57-65, and in Stewart C. R. et al (1998) Virology. 246(2): 329-340. The polynucleotide sequence of the P15 promoter is set out in SEQ ID NO: 1 and the polynucleotide sequence of the PE5 promoter is set out in SEQ ID NO: 2.

Molecular Biology Techniques

Molecular biology techniques used are known to the skilled person and described in Sambrook & Russell, *Molecular Cloning: A Laboratory Manual, 3rd Ed.*, CSHL Press, Cold Spring Harbor, N.Y., 2001). *B. subtilis* transformations were performed as described by Anagnostopolous, C., and J. Spizizen (1961, Requirements for transformation in *Bacillus subtilis*. J. Bacteriol. 81: 741-746). Polymerase chain reaction (PCR) was performed on a thermocycler with Phusion High-Fidelity DNA polymerase (Finnzymes O Y, Aspoo, Finland) according to the instructions of the manufacturer.

Glucan 1,4-α-Maltohydrolase Productivity

The glucan 1,4-α-maltohydrolase productivity was determined by measuring the glucan 1,4-α-maltohydrolase activity in the culture broth of *B. subtilis*. This was done using a Megazyme CERALPHA alpha amylase assay kit (Megazyme International Ireland Ltd., Co. Wicklow, Ireland) according to the manufacturer's instruction.

Xylanase Activity

The xylanase productivity was determined by measuring the xylanase activity in the culture broth of *B. subtilis*. This was quantified by EnzChek® Ultra Xylanase Assay Kit E33650 (Invitrogen, Ltd. Paisley, UK), this kit was used according to the instructions of the supplier.

Example 1

Construction of pDBC4XAS-1, an endo-1,4-beta-xylanase (xynA) Expression Plasmid

The DNA sequence of the xynA gene encoding the endo-1,4-beta-xylanase protein was retrieved from EMBL Nucleotide Sequence Database (http://www.ebi.ac.uk/embl/iNdex.html) Accession numbers CDS:CAB13776 (SEQ ID NO: 41). To express the endo-1,4-beta-xylanase gene from *Bacillus subtilis* 168 (*Bacillus* Genetic Stock Centre) the xynA gene was amplified from the *B. subtilis* 168 genome by PCR (Polymerase Chain Reaction) with the primers according to SEQ ID NO: 2 and 3). These primers introduced an AleI and a PacI site 5' of the xynA gene and a HindIII site 3' of the xynA gene.

The sequence of the forward primer for the 5'-flanking region of the xynA gene (including AleI, and PacI sites) (SEQ ID NO: 3)

5'-

CCAACACATTTGTGTTAATTAAAAAAGGAGCGATTTACATATGTTTAAGT

TTAAAAAGAATTTC-3'

The sequence of the reverse primer for the 3' region of the xynA gene (including HindIII site) (SEQ ID NO: 4)

5'-TAAATATAAAAGCTTCTCCAGCAATTCCAAGGCCGTTC-3'

The resulting PCR fragment was digested with the restriction enzymes AleI and HindIII and ligated with T4 DNA ligase into AleI and HindIII digested pNAPHB27 plasmid (Quax and Broekhuizen 1994 Appl. Microbiol. Biotechnol. 41: 425-431). The ligation mixture was transformed into *B. subtilis* strain BS154. A clone was selected and the xynA expression plasmid was named pDBC4XAS-1 (FIG. 1). The sequence of the plasmid was confirmed by DNA sequencing.

Example 2

Expression of Modified Expression Constructs for Endo-1, 4-Beta-Xylanase in *B. subtilis*

The xylanase expression vector pDBC4XAS-1 was transformed to *B. subtilis* strain 1A40 (TrpC2, lys3 and metB10) which resulted in strain BS1A40XAS-1 and the same plasmid was transformed to strain BS154 (ΔaprE and ΔnprE) which resulted in strain BS154XAS-1. The polynucleotide sequence of gene aprE (SEQ ID NO: 5) codes for extracellular alkaline protease AprE in *Bacillus subtilis* (SEQ ID NO: 6). The polynucleotide sequence of the gene nprE (SEQ ID NO: 7) codes for extracellular neutral protease NprE in *Bacillus subtilis* (SEQ ID NO: 8).

Figure 2:
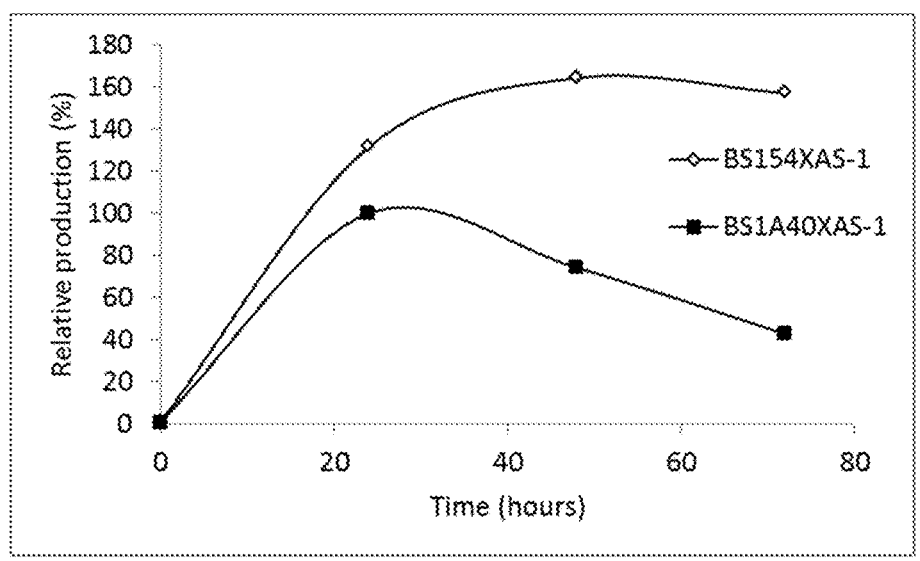
FIG. 2 sets out the relative xylanase production in shake flaks in time by strain BS154XAS-1 (ΔaprE and ΔnprE) and BS1A40XAS-1 (aprE+ and nprE+) in SMM medium.

Both strains were grown in a shake flask fermentation experiments. These shake flasks contained 20 ml SMM medium. SMM pre-medium contains 1.25% (w/w) yeast extract, 00.5% (w/w) CaCl2, 0.075% (w/w) $MgCl_2.6H_2O$, 15 µg/l $MnSO_4.4H_2O$, 10 µg/l $CoCl_2.6H_2O$, 0.05% (w/w) citric acid, 0.025% (w/w) antifoam 86/013 (Basildon Chemicals, Abingdon, UK). To complete SMM medium, 20 ml of 5% (w/v) maltose and 20 ml of a 200 mM Na-phosphate buffer stock solution (pH 6.8), both prepared and sterilized separately, were added to 60 ml SMM pre-medium. These cultures were incubated in a Microton incubator shaker (Infors AG, Bottmingen, Switzerland) for 48 hours at 3TC, 550 rpm and 80% humidity. The cultures were sampled after 24, 48 and 72 hours and the xylanase production in the supernatant was quantified by EnzChek® Ultra Xylanase Assay Kit E33650 (Invitrogen, Ltd. Paisley, UK). The xylanase production of both production strains was followed in time and is depicted in FIG. 2.

Clearly, strain BS154XAS-1 which contains the nprE and aprE deletions produces more xylanase than strain BS1A40XAS-1 which contains two intact copies of the genes coding for extracellular proteases AprE and NprE. The difference in production level increases in time and the largest difference can be observed after 72 hours. This example clearly demonstrates that the inactivation or deletion of the genes encoding the major extracellular protease AprE and NprE, in a *Bacillus* strain used for expression of useful compounds such as enzymes, leads to an increased production of said products by said strain.

Example 3. Construction of pDBC1

The multipurpose integration expression vector pDBC1 was designed to make use of type two S restriction enzyme cloning to combine promoters and genes of interest. An example of a type two S restriction enzyme is BsmBI. The amyE integration vector pBest4 as described in WO2008/148575 was modified by replacing the spectinomycin marker and lacZ gene with a synthetic DNA fragment (SEQ ID NO: 9).

(SEQ ID NO: 9)
5'-

GACGCGGTCATCAATCATACCACCAGTGATTATGCCGCGATTTCCAATGA

GGTTAAGAGTATTCCAAACTGGACACATGGAAACACACAAATTAAAAACT

GGTCTGATCGATGGGATGTCACGCAGAATTCATTGCTCGGGCTGTATGAC

TGGAATACACAAAATACACAAGTACAGTCCTATCTGAAACGGTTCTTAGA

CAGGGCATTGAATGACGGGGCAGACGGTTTTCGATTTGATGCCGCCAAAC

ATATAGAGCTTCCAGATGATGGCAGTTACGGCAGTCAATTTTGGCCGAAT

ATCACAAATACATCTGCAGAGTTCCAATACGGAGAAATCGCGGCCGCGGA

GACGCGCTCCTGTGACGGAAGATCACTTCGCAGAATAAATAAATCCTGGT

GTCCCTGTTGATACCGGGAAGCCCTGGGCCAACTTTTGGCGAAAATGAGA

CGTTGATCGGCACGTAAGAGGTTCCAACTTTCACCATAATGAAATAAGAT

CACTACCGGGCGTATTTTTTGAGTTATCGAGATTTTCAGGAGCTAAGGAA

GCTAAAATGGAGAAAAAAATCACTGGATATACCACCGTTGATATATCCCA

ATGGCATCGTAAAGAACATTTTGAGGCATTTCAGTCAGTTGCTCAATGTA

CCTATAACCAGACCGTTCAGCTGGATATTACGGCCTTTTTAAAGACCGTA

AAGAAAAATAAGCACAAGTTTTATCCGGCCTTTATTCACATTCTTGCCCG

CCTGATGAATGCTCATCCGGAATTCCGTATGGCAATGAAAGACGGTGAGC

TGGTGATATGGGATAGTGTTCACCCTTGTTACACCGTTTTCCATGAGCAA

ACTGAAACGTTTTCATCGCTCTGGAGTGAATACCACGACGATTTCCGGCA

GTTTCTACACATATATTCGCAAGATGTGGCGTGTTACGGTGAAAACCTGG

CCTATTTCCCTAAAGGGTTTATTGAGAATATGTTTTTCGTCTCAGCCAAT

CCCTGGGTGAGTTTCACCAGTTTTGATTTAAACGTGGCCAATATGGACAA

CTTCTTCGCCCCCGTTTTCACCATGGGCAAATATTATACGCAAGGCGACA

AGGTGCTGATGCCGCTGGCGATTCAGGTTCATCATGCCGTTTGTGATGGC

TTCCATGTCGGCAGAATGCTTAATGAATTACAACAGTACTGCGATGAGTG

GCAGGGCGGGCGTAAAGCGCGTCTCCATAAGTTTAAACAAATCTTTTTC

GAAAAAGGCCGCCCCGTTAAGAGGCGGCCTTATTCAAATTTCAGGATAT

GCACTTGCTTGCAAGCTTTACCGTTCGTATAATGTATGCTATACGAAGTT

ATTATTTTTAAAACAATGAATAGGTTTACACTTACTTTAGTTTTATGGAA

ATGAAAGATCATATCATATATAATCTAGAATAAAATTAACTAAAATAATT

-continued

```
ATTATCTAGATAAAAAATTTAGAAGCCAATGAAATCTATAAATAAACTAA

ATTAAGTTTATTTAATTAACAACTATGGATATAAAATAGGTACTAATCAA

AATAGTGAGGAGGATATATTTGAATACATACGAACAAATTAATAAAGTGA

AAAAAATACTTCGGAAACATTTAAAAAATAACCTTATTGGTACTTACATG

TTTGGATCAGGAGTTGAGAGTGGACTAAAACCAAATAGTGATCTTGACTT

TTTAGTCGTCGTATCTGAACCATTGACAGATCAAAGTAAAGAAATACTTA

TACAAAAAATTAGACCTATTTCAAAAAAAATAGGAGATAAAAGCAACTTA

CGATATATTGAATTAACAATTATTATTCAGCAAGAAATGGTACCGTGGAA

TCATCCTCCCAAACAAGAATTTATTTATGGAGAATGGTTACAAGAGCTTT

ATGAACAAGGATACATTCCTCAGAAGGAATTAAATTCAGATTTAACCATA

ATGCTTTACCAAGCAAAACGAAAAAATAAAAGAATATACGGAAATTATGA

CTTAGAGGAATTACTACCTGATATTCCATTTTCTGATGTGAGAAGAGCCA

TTATGGATTCGTCAGAGGAATTAATAGATAATTATCAGGATGATGAAACC

AACTCTATATTAACTTTATGCCGTATGATTTTAACTATGGACACGGGTAA

AATCATACCAAAAGATATTGCGGGAAATGCAGTGGCTGAATCTTCTCCAT

TAGAACATAGGGAGAGAATTTTGTTAGCAGTTCGTAGTTATCTTGGAGAG

AATATTGAATGGACTAATGAAAATGTAAATTTAACTATAAACTATTTAAA

TAACAGATTAAAAAAATTATAAAAAAATTGAAAAAATGGTGGAAACACTT

TTTTCAATTTTTTGTTTTATTATTTAATATTTGGGAAATATTCATTATA

ACTTCGTATAATGTATGCTATACGAACGGTACCTGCAGGATCCGTTTAGG

CTGGGCGGTGATAGCTTCTCGTTCAGGCAGTACGCCTCTTTTCTTTTCCA

GACCTGAGGGAGGCGGAAATGGTGTGAGGTTCCCGGGGAAAAGCCAAATA

GGCGATCGC -3'
```

Figure 3:
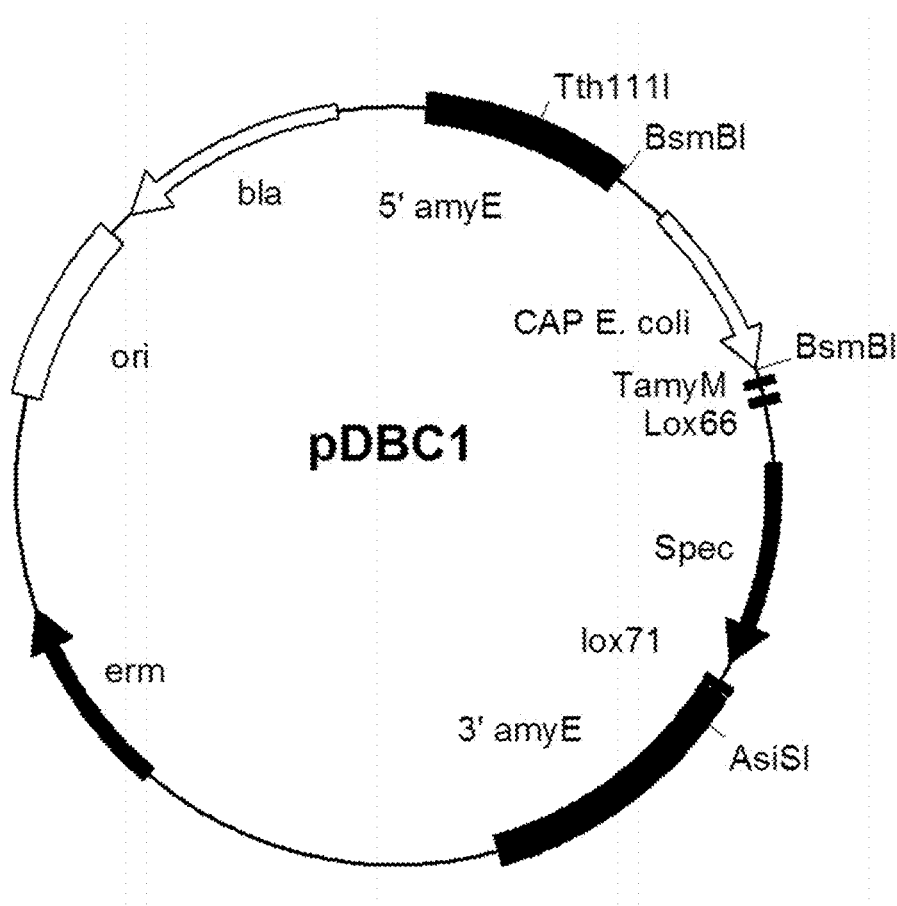
FIG. 3 sets out the physical map of the integration expression vector pDBC1. The BsmBI sites are used to exchange the CAP marker for a promoter fragment and gene of interest. The region between the amyE flanking regions integrates in the amyE locus and integrands are selected on spectinomycin.

Vector pBest4 was digested with TthIIII and AsisI and the synthetic DNA fragment (SEQ ID NO: 9) containing a TthIIII site, 340 bp of 5'-amyE, BsmBI site, chloramphenicol selection marker, amyM terminator, BsmBI site, lox 66 site, spectinomycin selection marker, lox71 site, 120 bp of 3'-amyE and AsisI site was inserted which resulted in vector pDBC1 (FIG. 3).

Example 4. Construction of Xylanase Expression Strains

Type two S restriction enzyme cloning was used to assemble the xylanase expression modules in vector pDBC1. The StarGate type two S restriction enzyme cloning system (IBA, GmbH, Göttingen, Germany) was used according to the instructions of the manufacturer. The xynA gene from *B. subtilis* 168 was amplified by PCR with: a forward primer to amplify the xynA gene from *B. subtilis* 168 and introduce a BsmBI site:

(SEQ ID NO: 10)
5'-CCAGAGCTC*AGCGCGTCTCC*TATGTTTAAGTTTAAAAAG-3' a reverse primer to amplify the xynA gene from *B. subtilis* 168 and introduce a BsmBI site:

(SEQ ID NO: 11)
5'-CTCCAGGTACC*AGCGCGTCTCC*TTATTACCACACTGTTACGTTAGAAC-3'

The two BsmBI sites were added to the 5' ends of both nucleic acids to allow cloning of the PCR product into pDBC1. This PCR product of 0.7 kb DNA fragment containing the xynA gene and two BsmBI sites was named construct XAS-1.

The modified expression module G00 (SEQ ID NO: 12) contains the *B. amyloliquefaciens* amyQ promoter, the mobU ribosome binding site sequence as present on plasmid pDBC4XAS-1, including a NdeI site at the ATG start and two BsmBI sites at the 5' and 3' ends (SEQ ID NO: 12)
5'-*AGCGCGTCTCC*CCGCCCAGACTGTCCGCTGTGTAAAAATAAGGAATAAAG

GGGGGTTGTTATTATTTTACTGATATGTAAAATATAATTTGTATAAGAAA

ATGAGAGGGAGAGGAAATTAATTAAAAAAGGAGCGATTTA<u>CATATG</u>GGAG

ACGCGCT-3'

The G01 (SEQ ID NO: 13) expression module P*Spo15*_RK41_SWITCH deletion, contain the P15 promoter, a modified RNA leader sequence as described in EP2186880 (nucleotides 31-251 of SEQ ID NO: 70 therein) and ribosome binding site and the G02 (SEQ ID NO: 15) expression module P$_{15\Omega grpE}$, contains the P15 promoter, mRNA stabilizing element as described in WO2008148575 and ribosome binding site.

((SEQ ID NO: 13)
5'-
<u>TAAAAATTTTACAAAAAGGTATTGACTTTCCCTACAGGGTGTGTAATAAT</u>

<u>TTAATTATAAGGACAAATGAATAAAGATTGTATCCTTCGGGGCAGGGTGG</u>

AAATCCCGACCGGCGGTAGTAAAGCACATTTGCTTTAGAGTCCGTGACCC

GTGTGCATAAGCACGCGGTGGATTCAGTTTAAGCTGAAGCCGACAGTGAA

AGTCTGGATGGGAGAAGGATGGACGGTAAATAACAAAAGAAAGGAGGTGA

T<u>CAT</u>-3'

(SEQ ID NO: 15)
5'-
<u>TAAAAATTTTACAAAAAGGTATTGACTTTCCCTACAGGGTGTGTAATAAT</u>

<u>TTAATTATAAGGACAAATGAATAAAGATT</u>GATTTTATCGAAGGGCAGCAC

CTGTCCTTCTCCTTACACTTTGAGGGAGGTGAACACAGACGGTAAATAAC

AAAAGAGGGGAGGGAAA<u>CAT</u>-3'

The G01 and G02 expression modules, respectively, were modified by including a NdeI site at the ATG start and two BsmBI sites at the 5' and 3' ends to yield SEQ ID NO: 14 and SEQ ID NO: 16, respectively. The expression modules G00, G01 and G02 were made synthetically.

(SEQ ID NO: 14)
5'-

*AGCGCGTCTCCCCGC*TAAAAATTTTACAAAAAGGTATTGACTTTCCCTAC

AGGGTGTGTAATAATTTAATTATAAGGACAAATGAATAAAGATTGTATCC

TTCGGGGCAGGGTGGAAATCCCGACCGGCGGTAGTAAAGCACATTTGCTT

TAGAGTCCGTGACCCGTGTGCATAAGCACGCGGTGGATTCAGTTTAAGCT

GAAGCCGACAGTGAAAGTCTGGATGGGAGAAGGATGGACGGTAAATAACA

AAAGAAAGGAGGTGATCATATGGGAGACGCGCT-3'

(SEQ ID NO: 16)
5'-

*AGCGCGTCTCCCGC*TAAAAATTTTACAAAAAGGTATTGACTTTCCCT

ACAGGGTGTGTAATAATTTAATTATAAGGACAAATGAATAAAGATTGAT

TTTATCGAAGGGCAGCACCTGTCCTTCTCCTTACACTTTGAGGGAGGTGA

ACACAGACGGTAAATAACAAAAGAGGGGAGGGAAACATATGGGAGACGCG

CT-3'

Figure 4:
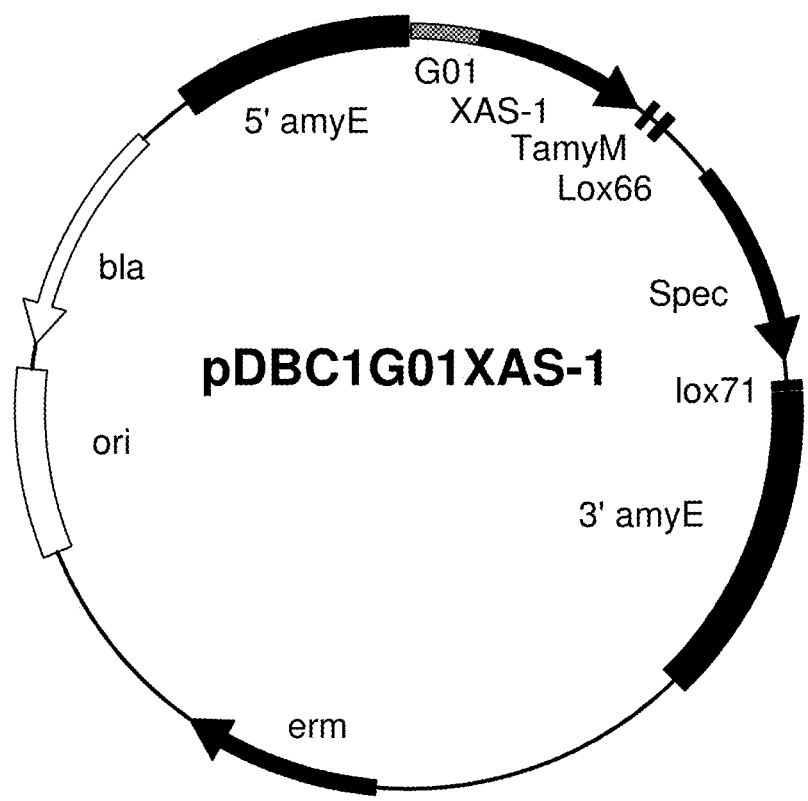
FIG. 4 sets out the schematic representation of the xynA expression integration vector pDBC1G01XAS-1 based on the pDBC1 vector.

The StarGate type two S restriction enzyme cloning system (IBA, GmbH, Göttingen, Germany) was used according to the instructions of the manufacturer to assemble two integration vectors. The first vector pDBC1G00XAS-1 was assembled from vector pDBC1, the G00 expression module and the XAS-1 module. The second vector pDBC1G01XAS-1 was assembled from the vector pDBC1, the G01 expression module and the XAS-1 module. The third vector pDBC1G02XAS-1 was assembled from the vector pDBC1, the G02 expression module and the XAS-1 module. The schematic representation of the pDBC1G01XAS-1 vector is depicted in FIG. 4 as an example. The final vectors pDBC1G00XAS-1, pDBC1G01XAS-1 and pDBC1G02XAS-1 only differ in the promoter module located 5' of the xylanase gene xynA present on the XAS-1 module.

These vectors were transformed to *B. subtilis* strains BS154 (ΔaprE and ΔnprE) and resulted in strains BS154G00XAS-1, BS154G01XAS-1, BS154G02XAS-1, which are listed in table 1. The transformants were selected in spectinomycin (100 μg/ml) containing agar plates. The amyE regions on pDBC1 targeted the constructs to the amyE locus. The double cross over transformants were only spectinomycin resistant whereas the undesired single cross-over transformants were also erythromycin resistant. The clones were also checked by PCR using the following primer combination:

a forward primer to amplify on the amyE locus:

5'-GGGAAGCGTTCACAGTTTCG-3'    (SEQ ID NO: 17)

a reverse primer on xynA:

5'-GGTTGCCGAAAACAAGCTAA-3'    (SEQ ID NO: 18)

The correct clones generated a fragment of 1.3 kb.

The polynucleotide sequence of the amyE gene (SEQ ID NO: 19) codes for the neutral amylase in *Bacillus subtilis* (SEQ ID NO: 20).

TABLE 1

| Strain | Parent strain | Vector |
|---|---|---|
| BS154G00XAS-1 | BS154 | pDBC1G00XAS-1 |
| BS154G01XAS-1 | BS154 | pDBC1G01XAS-1 |
| BS154G02XAS-1 | BS154 | pDBC1G02XAS-1 |

Example 5. Expression of endo-1,4-beta-xylanase in *B. subtilis*

*B. subtilis* strains BS154G00XAS-1, BS154G01XAS-1, and BS154G02XAS-1 expressing endo-1,4-beta-xylanase (table 1) were grown in 24 deep well plates (Axygen, Union City, USA). A 1 ml pre-culture was made in 2xTY medium composed of 1.6% (w/w) Bacto tryptone, 1% (w/w) yeast extract and 0.5% (w/w) NaCl. The 24 deep well plates were covered by a Breathseal (Greiner bio-one, Frickenhausen, Germany). After overnight growth at 37° C., 550 rpm and 80% humidity in a Microton incubator shaker (Infors AG, Bottmingen, Switzerland), 2 ml of SMM medium in 24 deep well plates (Axygen, Union City, USA) was inoculated with 1% (v/v) of the pre culture. SMM pre-medium contains 1.25% (w/w) yeast extract, 00.5% (w/w) CaCl2, 0.075% (w/w) $MgCl_2.6H_2O$, 15 μg/l $MnSO_4.4H_2O$, 10 μg/L $CoCl_2.6H_2O$, 0.05% (w/w) citric acid, 0.025% (w/w) antifoam 86/013 (Basildon Chemicals, Abingdon, UK). To complete SMM medium, 20 ml of 5% (w/v) maltose and 20 ml of a 200 mM Na-phosphate buffer stock solution (pH 6.8), both prepared and sterilized separately, were added to 60 ml SMM pre-medium. These cultures were incubated in a Microton incubator shaker (Infors AG, Bottmingen, Switzerland) for 48 hours at 37° C., 550 rpm and 80% humidity.

The cultures were sampled after 24 and 48 hours, cells were separated from the supernatant by centrifugation for 30 min at 4000 g and the endo-1,4-beta-xylanase production in the supernatants was analysed by EnzChek® Ultra Xylanase Assay Kit E33650 (Invitrogen, Ltd. Paisley, UK).

Figure 5:
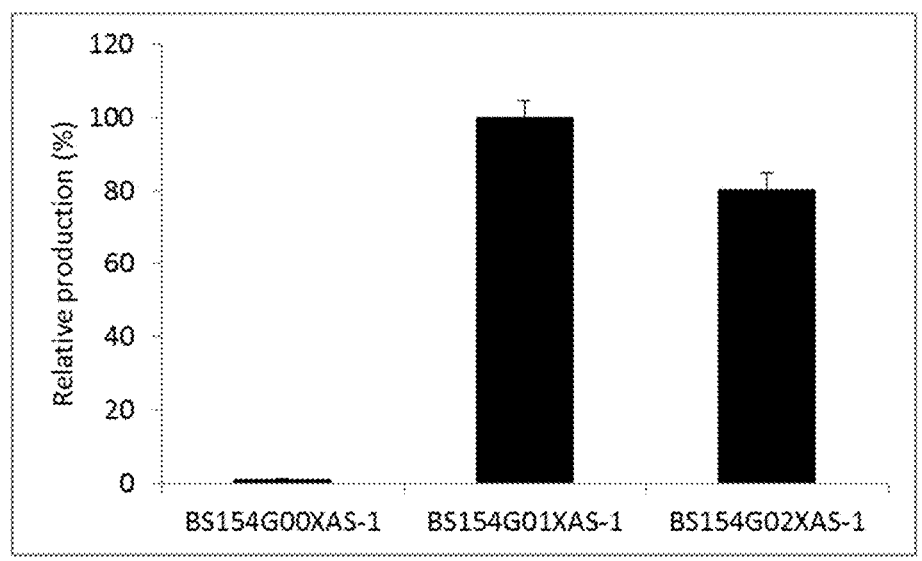
FIG. 5 sets out the relative xylanase production in 24 deep well plates by strains BS154G00XAS-1 (amyQ promoter), BS154G01XAS-1 (P15 promoter in the G01 expression module) and BS154G02XAS-1 (P15 promoter in the G02 expression module) in SMM medium.

As it can be seen in FIG. 5, the two strains BS154G01XAS-1 and BS154G02XAS-1 that contain the xynA gene behind expression modules G01 and G02 comprising the P15 promoter are expressing higher levels of xylanase if compared to strain BS154G00XAS-1 in which the xynA gene is behind the amyQ promoter. This result is clearly demonstrates the beneficial effect of the P15 promoter according to SEQ ID NO: 1 on enzyme productivity.

Example 6. Construction of Integration Vector pDBC5

Figure 6:
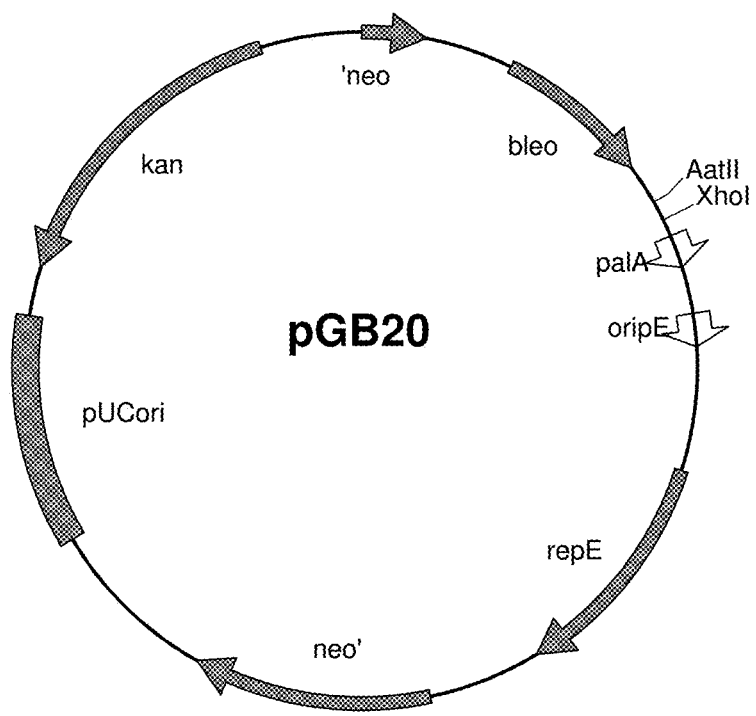
FIG. 6 sets out the schematic representation of the vector pGB20.

The pGB20 vector (FIG. 6) was made synthetically and contains the pE194 ori including oripE, palA and repE, for replication in *B. subtilis* below 37° C. and integration at 48° C. (Byeon W. H. and Weisblum B., 1990 "Replication genes of plasmid pE194-cop and repF: transcripts and encoded proteins." J Bacteriol. 10: 5892-5900), the bleomycin antibiotic marker from pUB110 giving resistance to phleomycin in *B. subtilis*. (McKenzie, et al. 1986, "The nucleotide sequence of pUB110: some salient features in relation to replication and its regulation." Plasmid. 2: 93-103), the pUC ori of pMB1 for replication in *E. coli* (Sgorbati et al., 1982, "Plasmids in the genus *Bifidobacterium*" J. Gen. Microbiol. 9: 2121-2131) and the kanamycin resistance gene for selection in *E. coli* (Nakano, et al. 1984, "Cloning of the kanamycin resistance gene from a kanamycin-producing *Streptomyces* species." J. Bacteriol. 1: 79-83).

The pGB20 vector was used to construct an integration vector that targets to the amyE locus of *B. subtilis*. The 5'- and 3'-regions of the amyE gene from *B. subtilis* 168 were amplified by polymerase chain reaction (PCR) with the following primers.

A forward primer to amplify the 5'-amyE region and introduce a StuI site:

(SEQ ID NO: 21)
5'- CCAAAGGCCTATGTTTGCAAAACGATTCAAAACCTC -3'

A reverse primer to amplify the 5'-amyE region and introduce NotI, HindIII and KnpI sites (SEQ ID NO: 22)
5'-
AGGTACCTCTAGAAGCTTACTAGTGCGGCCGCGATTTCTCCGTATTGGAA
CTCTGCAG -3'

A forward primer to amplify the 3'-amyE region and introducing NotI, HindIII and KnpI sites:

(SEQ ID NO: 23)
5'- GCGGCCGCACTAGTAAGCTTCTAGAGGTACCTGGCGTTGTGCTGGC
AAATGCAG -3'

A reverse primer to amplify the 3'-amyE region and introduce a XhoI site (SEQ ID NO: 24)
5'- GTTTCTCGAGATGGGGAAGAGAACCGCTTAAG -3'

Figure 7:
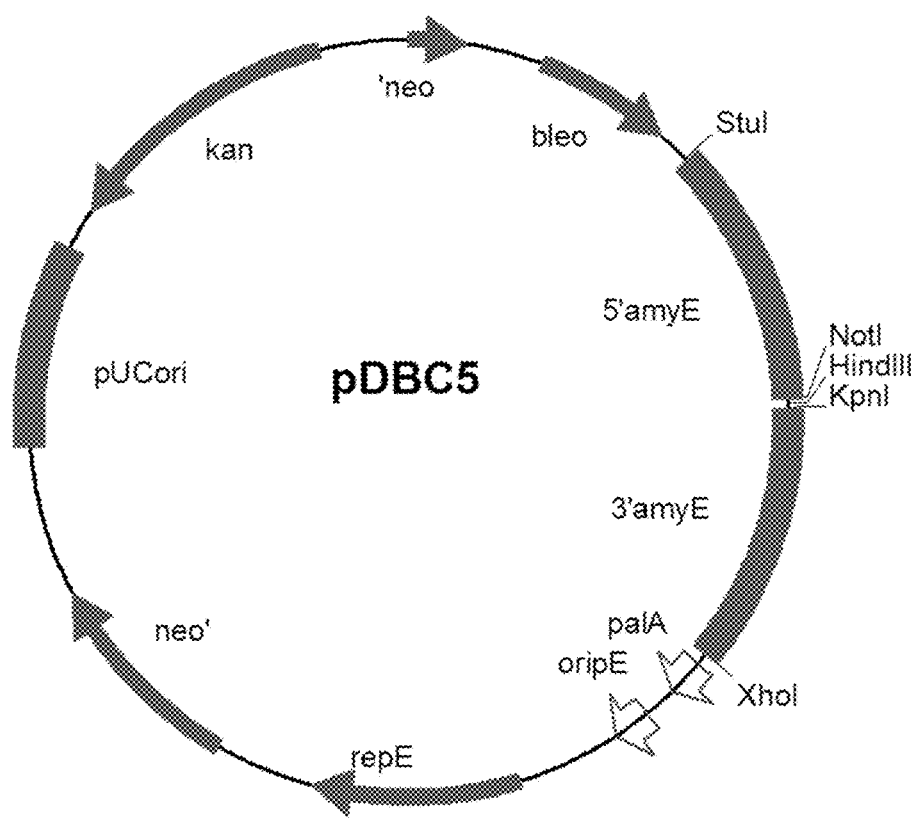
FIG. 7 sets out the schematic representation of the vector pDBC5.

The two fragments were fused by fusion PCR by adding 5 ng of the 5'-amyE and 3'-amyE fragments and primers SEQ-ID NO: 19 and SEQ-ID NO: 22 in one PCR reaction. The resulting 1500 bp PCR fragment was digested with StuI and XhoI and cloned into pGB20 which was digested with StuI and XhoI. The ligation reaction mixture was transformed to *E. coli* TOP10 cells. A clone was selected and this amyE integration plasmid was named pDBC5 (FIG. 7). The sequence of the plasmid was confirmed by DNA sequencing.

Example 7. Construction of Expression Vector pDBC5AMY1

For the construction of the glucan 1,4-α-maltohydrolase expression vector pDBC5AMY1 (FIG. 8) the amyM gene from *Geobacillus stearothermophilus* C599 including its native terminator was amplified by PCR with the following primers.

A forward primer to amplify the amyM gene and introduce a NotI site and amyQ promoter sequence, PacI and NdeI site:

(SEQ ID NO: 25)
5'-
ATCGCGGCCGCCCAGACTGTCCGCTGTGTAAAAATAAGGAATAAAGGGGG
GTTGTTATTATTTTACTGATATGTAAAATATAATTTGTATAAGAAAATGA
GAGGGAGAGGAAATTAATTAAAAAAGGAGCGATTTACATATGAAAAAGAA
AACGCTTTCTTTATTTGTGGG-3'

A reverse primer to amplify the amyM gene and introduce a HindIII site (SEQ ID NO: 26)
5'-TAAATATAAAAGCTTGCAAGCAAGTGCATATCCTG-3'

Figure 8:
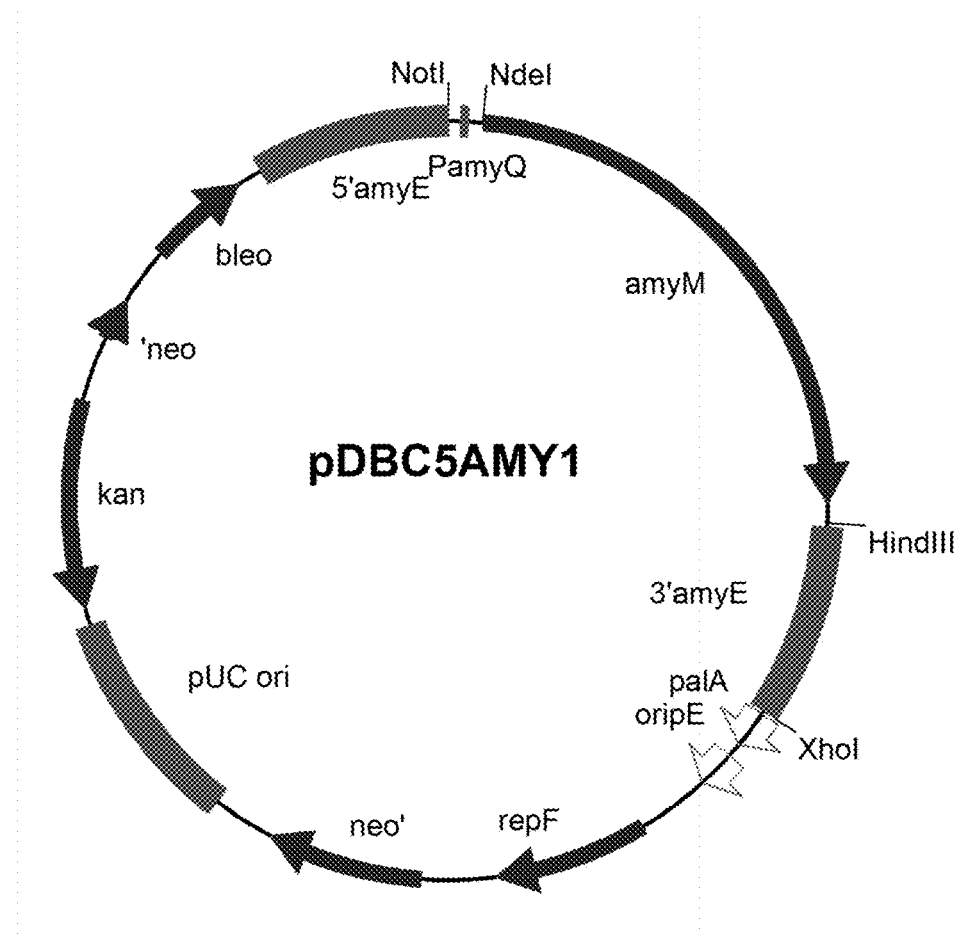
FIG. 8 sets out the schematic representation of vector pDBC5AMY1 used for the marker free integration of $P_{amyQ}$-AMY1 in the amyE locus of the *B. subtilis* genome. The amyQ promoter and mobU RBS are positioned between the NotI and NdeI sites, glucan 1,4-α-maltohydrolase (amyM) between the amyE flanks, neo$^R$, bled (gene conferring resistance to phleomycin in *Bacillus*), repE (temperature sensitive ori).

This 2.4 kb amyM DNA fragment containing amyM was digested with NotI and HindIII and cloned into pDBC5 which was digested with the same two enzymes. This expression and integration vector was named pDBC5AMY1 (FIG. 8).

The nucleotide sequence of the amyM gene obtained from *Geobacillus stearothermophilus* C599 is set out in SEQ ID NO: 27, while the amino acid sequence of the glucan 1,4-α-maltohydrolase obtained from *Geobacillus stearothermophilus* C599 encoded by the amyM gene is set out in SEQ ID NO: 28.

Example 8. Construction of Glucan 1,4-α-Maltohydrolase Expression Strains

The pDBC5AMY1 vector was transformed to BS154 (ΔaprE and ΔnprE) which resulted in strains BS154AMY1 (Table 2). Additional promoters were tested by removing the 139 bp reference expression module containing the amyQ promoter and the mobU ribosome binding site by NotI and NdeI digestion and inserting expression modules containing the promoter sequences of interest. These promoter modules (SEQ ID NO: 29-35) were made synthetically and contain a NotI site at the 5' end and a NdeI site at the 3' end.

Modified expression module G03 (SEQ ID NO: 29) contains the dual sigma 37 and sigma 55 promoter (Wang, P. Z., Doi R. H. (1984) Overlapping promoters transcribed by *Bacillus subtilis* sigma 55 and sigma 37 RNA polymerase holoenzymes during growth and stationary phases. J Biol Chem. 259(13):8619-8625), the mobU ribosome binding site, and further contains a NotI site at the 5' end and a NdeI site at the 3' end.

(SEQ ID NO: 29)
5'-
GCGGCCGCAGAAATGGGCGTGAAAAAAAGCGCGCGATTATGTAAAATATA
AAGTGATAGCGGTACCATTATAGTTAATTAAAAAAAGGAGCGATTTACATA
TG-3'

Modified expression module G04 (SEQ ID NO: 30) contains the *rapA* promoter, the mobU ribosome binding site, and further contains a NotI site at the 5' end and a NdeI site at the 3' end.

(SEQ ID NO: 30)
5'-
GCGGCCGCGAGAGCAAAGAAAAAGCCAGCGGGGAAGCTGGATGGAAAGAA
ACAAAGTCGGTTTTCACTAAAAGAAAGCACGGGTGTTTGAAAAACCCGTG
CTTTTTTGTTGCGGTTAGCCGAAATTCGACAATTGCGGTTATTTTGCGTT
CTTCTTTTTCTTGTAAATATGATAAAATATGACATATCTCGGGTAATTCA
AAATTAATTAAAAAAGGAGCGATTTACATATG-3'

Modified expression module G05 (SEQ ID NO: 31) contains the PE5 promoter the mobU ribosome binding site, and further contains a NotI site at the 5' end and a NdeI site at the 3' end.

(SEQ ID NO: 31)
5'-
GCGGCCGCGCTAAAATTCCTGAAAAATTTTGCAAAAAGTTGTTGACTTTA
TCTACAAGGTGTGGCATAATAATCTTAAAGAAAATGAGAGGGAGAGGAAA
TTAATTAAAAAAGGAGCGATTTACATATG-3'

Modified expression module G06 (SEQ ID NO: 32) contains the P15 and PE5 promoters, the mobU ribosome binding site, and further contains a NotI site at the 5' end and a NdeI site at the 3' end.

(SEQ ID NO: 32)
5'-
GCGGCCGCATCCACGCTGTGTAAAAATTTTACAAAAAGGTATTGACTTTC
CCTACAGGGTGTGTAATAATTTAATTAAGATCTGCTAAAATTCCTGAAAA
ATTTTGCAAAAAGTTGTTGACTTTATCTACAAGGTGTGGCATAATAATCT
TAAAGAAAATGAGAGGGAGAGGAAATTAATTAAAAAAGGAGCGATTTACA
TATG-3'

Modified expression module G07 (SEQ ID NO: 33) contains the P15 promoters, the mobU ribosome binding site, and further contains a NotI site at the 5' end and a NdeI site at the 3' end.

(SEQ ID NO: 33)
5'-
GCGGCCGCATCCACGCTGTGTAAAAATTTTACAAAAAGGTATTGACTTTC
CCTACAGGGTGTGTAATAATTTAATTAAAGAAAATGAGAGGGAGAGGAAA
TTAATTAAAAAAGGAGCGATTTACATATG-3'

Modified expression module G01 (SEQ ID NO: 34) contains the expression module G01 according to SEQ ID NO: 13, modified by inclusion of a NotI site at the 5' end and a NdeI site at the 3' end.

(SEQ ID NO: 34)
5'-
GCGGCCGCTAAAAATTTTACAAAAAGGTATTGACTTTCCCTACAGGGTGT
GTAATAATTTAATTATAAGGACAAATGAATAAAGATTGTATCCTTCGGGG
CAGGGTGGAAATCCCGACCGGCGGTAGTAAAGCACATTTGCTTTAGAGTC
CGTGACCCGTGTGCATAAGCACGCGGTGGATTCAGTTTAAGCTGAAGCCG
ACAGTGAAAGTCTGGATGGGAGAAGGATGGACGGTAAATAACAAAAGAAA
GGAGGTGATCATATG-3'

Modified expression module G02 (SEQ ID NO: 35) contains the expression module G02 of SEQ ID NO: 14, modified by inclusion of a NotI site at the 5' end and a NdeI site at the 3'end.

(SEQ ID NO: 35)
5'-
GCGGCCGCTAAAAATTTTACAAAAAGGTATTGACTTTCCCTACAGGGTGT
GTAATAATTTAATTATAAGGACAAATGAATAAAGATTGATTTTATCGAAG
GGCAGCACCTGTCCTTCTCCTTACACTTTGAGGGAGGTGAACACAGACGG
TAAATAACAAAAGAGGGGAGGGAAACATATG-3'

The modified expression modules G03, G04, G05, G06, G07, G01 and G02 according to SEQ ID NO: 29 to 35 were cloned into pDBC5AMY1 5' to the amyM gene, which yielded vectors pDBC5G03AMY1, pDBC5G04AMY1, pDBC5G05AMY1, pDBC5G06AMY1, pDBC5G07AMY1, pDBC5G01AMY1 and pDBC5G02AMY1, respectively.

These vectors were transformed to BS154 (ΔaprE and ΔnprE) to yield strains as indicated in Table 3. Since these vectors contain the thermo-sensitive origin of replication these vectors are integrated into the *B. subtilis* chromosome by elevating the growth temperature to 48° C. and maintaining antibiotic selection pressure (4 µg/ml phleomycin). Homologous recombination directed by the amyE regions allowed for integration into the amyE locus. The integrated clones were used for excision of the integrated plasmid by growth at a permissive temperature in the absence of antibiotic pressure. The amyM insertions and plasmid excisions were confirmed by PCR using the following primers.

A forward primer to amplify the amyE locus outside the 5'-flank:

5'-TTTTGACTCCGAAGTAAGTCTTC-3'     (SEQ ID NO: 37)

A reverse primer to on the amyE locus outside the 3'-flank:

5'-ATGGTTTCTTTCGGTAAGTCCCG-3'     (SEQ ID NO: 38)

The amplified PCR fragments were sequence verified.

TABLE 3

| Strain | Parent strain | Vector. |
| --- | --- | --- |
| BS154AMY1 | BS154 | pDBC5AMY1 |
| BS154G03AMY1 | BS154 | pDBC5G03AMY1 |
| BS154G04AMY1 | BS154 | pDBC5G04AMY1 |
| BS154G05AMY1 | BS154 | pDBC5G05AMY1 |
| BS154G06AMY1 | BS154 | pDBC5G06AMY1 |
| BS154G07AMY1 | BS154 | pDBC5G07AMY1 |
| BS154G01AMY1 | BS154 | pDBC5G01AMY1 |
| BS154G02AMY1 | BS154 | pDBC5G02AMY1 |

Example 9. Expression of Glucan 1,4-α-Maltohydrolase by *B. subtilis*

Figure 9:
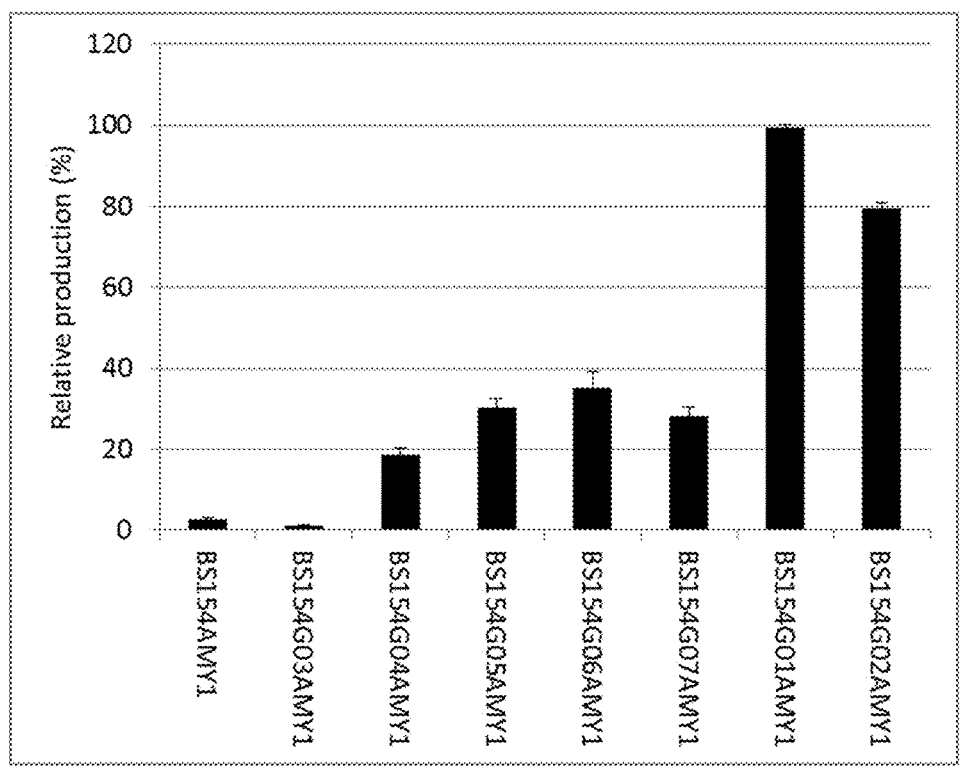
FIG. 9 sets out the relative glucan 1,4-α-maltohydrolase production in 24 deep well plates by strains BS154AMY1 (amyQ promoter), BS154G03AMY1 (P15 promoter in expression module G03), BS154G04AMY1 (P15 promoter in expression module G04), BS154G05AMY1 (P15 promoter in expression module G05), BS154G06AMY1 (P15 promoter in expression module G06), BS154G07AMY1 (P15 promoter in expression module G07), BS154G01AMY1 (P15 promoter in expression module G01) and BS154G02AMY1 (P15 promoter in expression module G02) in SMM medium.

*B. subtilis* strains expressing glucan 1,4-α-maltohydrolase BS154AMY1, BS154G03AMY1, BS154G04AMY1, BS154G05AMY1, BS154G06AMY1, BS154G07AMY1, BS154G01AMY1, BS154G02AMY1 (Table 3) were grown in 24 deep well plates (Axygen, Union City, USA). A 1 ml pre-culture was made in 2xTY medium composed of 1.6% (w/w) Bacto tryptone, 1% (w/w) yeast extract and 0.5% (w/w) NaCl. The 24 deep well plates were covered by a Breathseal (Greiner bio-one, Frickenhausen, Germany). After overnight growth at 3TC, 550 rpm and 80% humidity in a Microton incubator shaker (Infors AG, Bottmingen, Switzerland), 2 ml of SMM medium in 24 deep well plates (Axygen, Union City, USA) was inoculated with 1% (v/v) of the pre culture. SMM pre-medium contains 1.25% (w/w) yeast extract, 00.5% (w/w) CaCl2, 0.075% (w/w) MgCl$_2$.6H$_2$O, 15 µg/L MnSO$_4$. 4H$_2$O, 10 µg/L CoCl$_2$.6H$_2$O, 0.05% (w/w) citric acid, 0.025% (w/w) antifoam 86/013 (Basildon Chemicals, Abingdon, UK). To complete SMM medium, 20 ml of 5% (w/v) maltose and 20 ml of a 200 mM Na-phosphate buffer stock solution (pH 6.8), both prepared and sterilized separately, were added to 60 ml SMM pre-medium. These cultures were incubated in a Microton incubator shaker (Infors AG, Bottmingen, Switzerland) for 48 hours at 37° C., 550 rpm and 80% humidity. These cultures were incubated for at 3TC and 250 rpm. The cultures were sampled after 48 hours and the glucan 1,4-α-maltohydrolase productivity was quantified with the Megazyme CERALPHA alpha amylase assay kit (Megazyme International Ireland Ltd., Co. Wicklow, Ireland). Strains BS154G05AMY1 and BS154G06AMY1 containing the PE5 promoter and strains BS154G06AMY1, BS154G07AMY1, BS154G01AMY1, BS154G02AMY1 containing the P15 promoter 5' to the amyM gene expressed higher levels of glucan 1,4-α-maltohydrolase if compared to strains BS154AMY1 and BS154G03AMY1 containing the amyQ or sigma 37 and sigma 55 promoters 5' to the amyM gene. This result is clearly demonstrating the beneficial effect of the PE5 and P15 promoters from bacterial phage SPO1 on enzyme productivity. The results are reported in FIG. 9.

The invention claimed is:

1. A recombinant *Bacillus* host cell modified in its genome to be deficient in the production of a neutral protease and an alkaline protease which host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage Spounalikevirus *Bacillus* phage SPO1 (SPO1) promoter sequence, and wherein the bacteriophage Spounalikevirus *Bacillus* phage SPO1 (SPO1) promoter sequence is part of an expression module comprising the bacteriophage SPO1 promoter, a modified riboflavin biosynthetic genes (rib) leader and a sequence coding for a ribosome binding site (RBS), wherein the expression module further comprises a mRNA stabilizing element, and wherein the modified rib leader is located downstream of the promoter and upstream of the sequence coding for the RBS.

2. The method of producing the recombinant *Bacillus* host cell according to claim 1 comprising:
   a. providing a *Bacillus* host cell modified in its genome to be deficient in the production of a neutral protease and in the production of an alkaline protease; and
   b. transforming the *Bacillus* host cell with the nucleic acid construct of claim 1.

3. The host cell according to claim 1, wherein the mRNA stabilizing element is selected from aprE, grpE, cotG, SP82, RSBgsiB, and CryIIIA mRNA stabilizing elements.

4. The host cell according to claim 1, wherein the modified rib leader is a rib leader comprising the ribO mutation C85T, wherein the rib leader is SEQ ID NO: 55.

5. The host cell according to claim 1, wherein the expression module has a polynucleotide sequence selected from SEQ ID NO: 13, SEQ ID NO: 14, SEQ ID NO: 15, SEQ ID NO: 16, SEQ ID NO: 31, SEQ ID NO: 32, SEQ ID NO: 33, SEQ ID NO: 34, SEQ ID NO: 35.

6. The host cell according to claim 1, wherein the host cell belongs to a species selected from the group consisting of: *B. agaradherens, B. alkalophilus, B. amyloliquefaciens, B. anthracis, B. atrophaeus, B. brevis, B. cereus, B. circulans, B. clausii, B. coagulans, B. firmus, B. halodurans, B. lautus, B. lentus, B. licheniformis, B. megaterium, B. mojavensis, B. pumilus, B. puntis, B. sphaericus, B. stearothermophilus, B. subtilis, B. thuringiensis, B. vallismortis*, preferably which belongs to *B. subtilis, B. amyloliquefaciens* or *B. licheniformis*.

7. The host cell according to claim 1, wherein the host cell does not produce spores and is deficient in a sporulation-related gene selected from the group consisting of spoOA, spoIISA, spoIIAC, sigE, sigF, spoIISB, spoIIE, sigG, spoIVCB, spoIIIC, spoIIGA, spoIIAA, spoIVFB, spoIIR, and spoIII.

8. The host cell according to claim 1 wherein the host cell comprises more than one copy of the nucleic acid construct and the nucleic acid constructs are integrated into the host cell genome.

9. The host cell according to claim 1 which is a marker-free host cell.

10. A recombinant *Bacillus* host cell modified in its genome to be deficient in the production of a neutral protease and an alkaline protease which host cell comprises a nucleic acid construct, wherein the nucleic acid construct comprises a polynucleotide encoding a compound of interest or encoding a compound involved in the synthesis of a compound of interest operably linked to a promoter sequence allowing for expression of the polynucleotide in the host cell, wherein the promoter comprises a bacteriophage Spounalikevirus *Bacillus* phage SPO1 (SPO1) promoter sequence wherein the host cell is a *Bacillus subtilis* and wherein the neutral protease in which the host cell is deficient has an amino acid sequence according to SEQ ID NO: 8 or an amino acid sequence at least 90% identical to SEQ ID NO: 8 and wherein the alkaline protease has an amino acid sequence according to SEQ ID NO: 6 or an amino acid sequence at least 90% identical to SEQ ID NO: 6, wherein the *Bacillus subtilis* host cell is further deficient in the production of neutral amylase, wherein the neutral amylase has an amino acid sequence according to SEQ ID NO: 20 or an amino acid sequence at least 90% identical to SEQ ID NO: 20.

11. The method according claim 2 wherein in b. the *Bacillus* host cell is transformed with more than one copy of the nucleic acid construct, and the nucleic acid constructs are integrated into the host cell genome.

12. The method according claim 2 wherein in b. one or more nucleic acid constructs comprise a selectable marker located between two lox sites, preferably located between a lox 66 and a lox 71 site.

13. The method according to claim 12 wherein the method further comprises c. selecting the *Bacillus* host cells which have been transformed with the one or more nucleic acid constructs comprising the selectable marker; and preferably d. removing the selectable marked by Cre recombinase-mediated recombination of the lox sites, preferably of the lox66 and the lox 71 sites to yield a lox 72 site in the *Bacillus* host cell genome.

14. A method for the production of a compound of interest comprising:
 a) culturing a recombinant *Bacillus* host cell according to claim 1 under conditions conducive to the production of the compound of interest, and
 b) isolating the compound of interest from the culture broth.

15. The recombinant *Bacillus* host cell according to claim 1, wherein the recombinant host cells makes a compound of interest.

16. The host cell of claim 1, wherein the host cell is further deficient in the production of a neutral α-amylase.

17. The host cell of claim 3, wherein the mRNA stabilizing element has the sequence of one of SEQ ID NO:48 to SEQ ID NO:54.

18. The host cell of claim 17, wherein the mRNA stabilizing element has the sequence of SEQ ID NO:48 or SEQ ID NO:49.

19. The host cell of claim 4, further comprising a deletion of nucleotides corresponding to nucleotides 166 to 263 of SEQ ID NO:55.

20. The host cell of claim 10 wherein the SPO1 promoter is SEQ ID NO: 1 or SEQ ID NO: 2.

* * * * *

```
                           SEQUENCE LISTING

<160> NUMBER OF SEQ ID NOS: 59

<210> SEQ ID NO 1
<211> LENGTH: 57
<212> TYPE: DNA
<213> ORGANISM: Bacteriophage SPO1

<400> SEQUENCE: 1
taaaaatttt acaaaaaggt attgactttc cctacagggt gtgtaataat ttaatta          57

<210> SEQ ID NO 2
<211> LENGTH: 57
<212> TYPE: DNA
<213> ORGANISM: Bacteriophage SPO1

<400> SEQUENCE: 2
gaaaaatttt gcaaaaagtt gttgacttta tctacaaggt gtggcataat aatctta          57

<210> SEQ ID NO 3
<211> LENGTH: 64
<212> TYPE: DNA
<213> ORGANISM: artificial sequence
<220> FEATURE:
<223> OTHER INFORMATION: primer

<400> SEQUENCE: 3
ccaacacatt tgtgttaatt aaaaaaggag cgatttacat atgtttaagt ttaaaaagaa       60
tttc                                                                   64

<210> SEQ ID NO 4
<211> LENGTH: 38
<212> TYPE: DNA
<213> ORGANISM: artificial sequence
<220> FEATURE:
<223> OTHER INFORMATION: primer

<400> SEQUENCE: 4
taaatataaa agcttctcca gcaattccaa ggccgttc                               38

<210> SEQ ID NO 5
<211> LENGTH: 1146
<212> TYPE: DNA
<213> ORGANISM: Bacillus subtilis

<400> SEQUENCE: 5
gtgagaagca aaaaattgtg gatcagcttg ttgtttgcgt taacgttaat ctttacgatg        60
gcgttcagca acatgtctgc gcaggctgcc ggaaaaagca gtacagaaaa gaaatacatt      120
gtcggattta aacagacaat gagtgccatg agttccgcca agaaaaagga tgttatttct      180
gaaaaaggcg gaaaggttca aaagcaattt aagtatgtta acgcggccgc agcaacattg      240
```

```
gatgaaaaag ctgtaaaaga attgaaaaaa gatccgagcg ttgcatatgt ggaagaagat    300
catattgcac atgaatatgc gcaatctgtt ccttatggca tttctcaaat taaagcgccg    360
gctcttcact ctcaaggcta cacaggctct aacgtaaaag tagctgttat cgacagcgga    420
attgactctt ctcatcctga cttaaacgtc agaggcggag caagcttcgt accttctgaa    480
acaaacccat accaggacgg cagttctcac ggtacgcatg tagccggtac gattgccgct    540
cttaataact caatcggtgt tctgggcgta gcgccaagcg catcattata tgcagtaaaa    600
gtgcttgatt caacaggaag cggccaatat agctggatta ttaacggcat tgagtgggcc    660
atttccaaca atatggatgt tatcaacatg agccttggcg gacctactgg ttctacagcg    720
ctgaaaacag tcgttgacaa agccgtttcc agcggtatcg tcgttgctgc cgcagccgga    780
aacgaaggtt catccggaag cacaagcaca gtcggctacc ctgcaaaata tccttctact    840
attgcagtag gtgcggtaaa cagcagcaac caaagagctt cattctccag cgcaggttct    900
gagcttgatg tgatggctcc tggcgtgtcc atccaaagca cacttcctgg aggcacttac    960
ggcgcttata acggaacgtc catggcgact cctcacgttg ccggagcagc agcgttaatt   1020
ctttctaagc acccgacttg gacaaacgcg caagtccgtg atcgtttaga aagcactgca   1080
acatatcttg gaaactcttt ctactatgga aaagggttaa tcaacgtaca agcagctgca   1140
caataa                                                             1146

<210> SEQ ID NO 6
<211> LENGTH: 381
<212> TYPE: PRT
<213> ORGANISM: Bacillus subtilis

<400> SEQUENCE: 6

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ser Ser Thr Glu Lys Lys Tyr Ile Val Gly Phe Lys Gln Thr Met Ser
        35                  40                  45

Ala Met Ser Ser Ala Lys Lys Lys Asp Val Ile Ser Glu Lys Gly Gly
    50                  55                  60

Lys Val Gln Lys Gln Phe Lys Tyr Val Asn Ala Ala Ala Thr Leu
65                  70                  75                  80

Asp Glu Lys Ala Val Lys Glu Leu Lys Lys Asp Pro Ser Val Ala Tyr
                85                  90                  95

Val Glu Glu Asp His Ile Ala His Glu Tyr Ala Gln Ser Val Pro Tyr
            100                 105                 110

Gly Ile Ser Gln Ile Lys Ala Pro Ala Leu His Ser Gln Gly Tyr Thr
        115                 120                 125

Gly Ser Asn Val Lys Val Ala Val Ile Asp Ser Gly Ile Asp Ser Ser
    130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Ser Ile Gly Val Leu Gly Val Ala Pro
            180                 185                 190

Ser Ala Ser Leu Tyr Ala Val Lys Val Leu Asp Ser Thr Gly Ser Gly
        195                 200                 205
```

```
Gln Tyr Ser Trp Ile Ile Asn Gly Ile Glu Trp Ala Ile Ser Asn Asn
        210                 215                 220
Met Asp Val Ile Asn Met Ser Leu Gly Gly Pro Thr Gly Ser Thr Ala
225                 230                 235                 240
Leu Lys Thr Val Val Asp Lys Ala Val Ser Ser Gly Ile Val Val Ala
                245                 250                 255
Ala Ala Ala Gly Asn Glu Gly Ser Ser Gly Ser Thr Ser Thr Val Gly
            260                 265                 270
Tyr Pro Ala Lys Tyr Pro Ser Thr Ile Ala Val Gly Ala Val Asn Ser
        275                 280                 285
Ser Asn Gln Arg Ala Ser Phe Ser Ser Ala Gly Ser Glu Leu Asp Val
    290                 295                 300
Met Ala Pro Gly Val Ser Ile Gln Ser Thr Leu Pro Gly Gly Thr Tyr
305                 310                 315                 320
Gly Ala Tyr Asn Gly Thr Ser Met Ala Thr Pro His Val Ala Gly Ala
                325                 330                 335
Ala Ala Leu Ile Leu Ser Lys His Pro Thr Trp Thr Asn Ala Gln Val
            340                 345                 350
Arg Asp Arg Leu Glu Ser Thr Ala Thr Tyr Leu Gly Asn Ser Phe Tyr
        355                 360                 365
Tyr Gly Lys Gly Leu Ile Asn Val Gln Ala Ala Gln
        370                 375                 380

<210> SEQ ID NO 7
<211> LENGTH: 1566
<212> TYPE: DNA
<213> ORGANISM: Bacillus subtilis

<400> SEQUENCE: 7
gtgggtttag gtaagaaatt gtctgttgct gtcgctgctt cgtttatgag tttatcaatc      60
agcctgccag gtgttcaggc tgctgaaggt catcagctta agagaatcaa acaaatttc     120 ctctccaaaa acgcgattgc gcaatcagaa ctctctgcac caaatgacaa ggctgtcaag     180 cagttttga aaaagaacag caacatttt aaaggtgacc cttccaaaag gctgaagctt      240
gttgaaagca cgactgatgc ccttggatac aagcactttc gatatgcgcc tgtcgttaac     300
ggagtgccaa ttaaagattc gcaagtgatc gttcacgtcg ataaatccga taatgtctat     360
gcggtcaatg gtgaattaca caatcaatct gctgcaaaaa cagataacag ccaaaaagtc     420
tcttctgaaa aagcgctggc actcgctttc aaagctatcg gcaaatcacc agacgctgtt     480
tctaacggag cggccaaaaa cagcaataaa gccgaattaa aagcgataga aacaaaagac     540
ggcagctatc gtcttgctta cgacgtgacg attcgctatg tcgagcctga acctgcaaac     600
tgggaagtct tagttgacgc cgaaacaggc agcattttaa acagcaaaaa taaagtagaa     660
catgccgccg ccactggaag cggaacaacg ctaaagggcg caactgttcc tttgaacatc     720
tcttatgaag gcgaaaaata tgttctaaga gatctttcaa aaccaacagg cacccaaatc     780
atcacatatg atttgcaaaa cagacaaagc cgccttccgg gcacgcttgt ctcaagcaca     840
acgaaaacat ttacatcttc atcacagcgg gcagccgttg acgcacacta taacctcggt     900
aaagtgtacg attatttta tcaaactttt aaacgaaaca gctatgataa caaaggcagt     960
aaaatcgttt cttccgttca ctacggcact caatacaata acgctgcatg gacaggagac    1020
cagatgattt acggtgatgg cgacggttca ttcttctctc cgctttccgg ctcattagat    1080
gtgacagcgc atgaaatgac acatggcgtc acccaagaaa cagccaactt gatttatgaa    1140
```

-continued

```
aatcagccag gtgcattaaa cgagtctttc tctgacgtat tcgggtattt taacgataca   1200
gaagactggg acatcggtga agacattacg gtcagccagc ctgctcttcg cagcctgtcc   1260
aaccctacaa atacaacca gcctgacaat tacgccaatt accgaaacct tccaaacaca    1320
gatgaaggcg attatggcgg tgtacacaca aacagcggaa ttccaaacaa agccgcttac   1380
aacaccatca caaaacttgg tgtatctaaa tcacagcaaa tctattaccg tgcgttaaca   1440
acgtacctca cgccttcttc cacgttcaaa gatgccaagg cagctctcat tcagtctgcc   1500
cgtgacctct acggctcaac tgatgccgct aaagttgaag cagcctggaa tgctgttgga   1560
ttgtaa                                                              1566
```

<210> SEQ ID NO 8
<211> LENGTH: 521
<212> TYPE: PRT
<213> ORGANISM: Bacillus subtilis

<400> SEQUENCE: 8

```
Met Gly Leu Gly Lys Lys Leu Ser Val Ala Val Ala Ser Phe Met
1               5                   10                  15

Ser Leu Ser Ile Ser Leu Pro Gly Val Gln Ala Ala Glu Gly His Gln
            20                  25                  30

Leu Lys Glu Asn Gln Thr Asn Phe Leu Ser Lys Asn Ala Ile Ala Gln
        35                  40                  45

Ser Glu Leu Ser Ala Pro Asn Asp Lys Ala Val Lys Gln Phe Leu Lys
    50                  55                  60

Lys Asn Ser Asn Ile Phe Lys Gly Asp Pro Ser Lys Arg Leu Lys Leu
65                  70                  75                  80

Val Glu Ser Thr Thr Asp Ala Leu Gly Tyr Lys His Phe Arg Tyr Ala
                85                  90                  95

Pro Val Val Asn Gly Val Pro Ile Lys Asp Ser Gln Val Ile Val His
            100                 105                 110

Val Asp Lys Ser Asp Asn Val Tyr Ala Val Asn Gly Glu Leu His Asn
        115                 120                 125

Gln Ser Ala Ala Lys Thr Asp Asn Ser Gln Lys Val Ser Ser Glu Lys
    130                 135                 140

Ala Leu Ala Leu Ala Phe Lys Ala Ile Gly Lys Ser Pro Asp Ala Val
145                 150                 155                 160

Ser Asn Gly Ala Ala Lys Asn Ser Asn Lys Ala Glu Leu Lys Ala Ile
                165                 170                 175

Glu Thr Lys Asp Gly Ser Tyr Arg Leu Ala Tyr Asp Val Thr Ile Arg
            180                 185                 190

Tyr Val Glu Pro Glu Pro Ala Asn Trp Glu Val Leu Val Asp Ala Glu
        195                 200                 205

Thr Gly Ser Ile Leu Lys Gln Gln Asn Lys Val Glu His Ala Ala Ala
    210                 215                 220

Thr Gly Ser Gly Thr Thr Leu Lys Gly Ala Thr Val Pro Leu Asn Ile
225                 230                 235                 240

Ser Tyr Glu Gly Gly Lys Tyr Val Leu Arg Asp Leu Ser Lys Pro Thr
                245                 250                 255

Gly Thr Gln Ile Ile Thr Tyr Asp Leu Gln Asn Arg Gln Ser Arg Leu
            260                 265                 270

Pro Gly Thr Leu Val Ser Ser Thr Thr Lys Thr Phe Thr Ser Ser Ser
        275                 280                 285
```

Gln Arg Ala Ala Val Asp Ala His Tyr Asn Leu Gly Lys Val Tyr Asp
    290                 295                 300

Tyr Phe Tyr Ser Asn Phe Lys Arg Asn Ser Tyr Asp Asn Lys Gly Ser
305                 310                 315                 320

Lys Ile Val Ser Val His Tyr Gly Thr Gln Tyr Asn Asn Ala Ala
                325                 330                 335

Trp Thr Gly Asp Gln Met Ile Tyr Gly Asp Gly Asp Ser Phe Phe
                340                 345                 350

Ser Pro Leu Ser Gly Ser Leu Asp Val Thr Ala His Glu Met Thr His
        355                 360                 365

Gly Val Thr Gln Glu Thr Ala Asn Leu Ile Tyr Glu Asn Gln Pro Gly
370                 375                 380

Ala Leu Asn Glu Ser Phe Ser Asp Val Phe Gly Tyr Phe Asn Asp Thr
385                 390                 395                 400

Glu Asp Trp Asp Ile Gly Glu Asp Ile Thr Val Ser Gln Pro Ala Leu
                405                 410                 415

Arg Ser Leu Ser Asn Pro Thr Lys Tyr Asn Gln Pro Asn Tyr Ala
            420                 425                 430

Asn Tyr Arg Asn Leu Pro Asn Thr Asp Glu Gly Asp Tyr Gly Gly Val
            435                 440                 445

His Thr Asn Ser Gly Ile Pro Asn Lys Ala Ala Tyr Asn Thr Ile Thr
450                 455                 460

Lys Leu Gly Val Ser Lys Gln Gln Ile Tyr Tyr Arg Ala Leu Thr
465                 470                 475                 480

Thr Tyr Leu Thr Pro Ser Ser Thr Phe Lys Asp Ala Lys Ala Ala Leu
                485                 490                 495

Ile Gln Ser Ala Arg Asp Leu Tyr Gly Ser Thr Asp Ala Ala Lys Val
            500                 505                 510

Glu Ala Ala Trp Asn Ala Val Gly Leu
515                 520

<210> SEQ ID NO 9
<211> LENGTH: 2559
<212> TYPE: DNA
<213> ORGANISM: artificial sequence
<220> FEATURE:
<223> OTHER INFORMATION: synthetic DNA fragment containing a TthIIII
      site, 340 bp of 5'-amyE, BsmBI site, chloramphenicol selection
      marker, amyM terminator, BsmBI site, lox 66 site, spectinomycin
      selection marker, lox71 site, 120 bp of 3'-amyE and AsisI site

<400> SEQUENCE: 9
gacgcggtca tcaatcatac caccagtgat tatgccgcga tttccaatga ggttaagagt      60
attccaaact ggacacatgg aaacacacaa attaaaaact ggtctgatcg atgggatgtc    120
acgcagaatt cattgctcgg gctgtatgac tggaatacac aaaatacaca agtacagtcc    180
tatctgaaac ggttcttaga cagggcattg aatgacgggg cagacggttt tcgatttgat    240
gccgccaaac atatagagct tccagatgat ggcagttacg gcagtcaatt ttggccgaat    300
atcacaaata catctgcaga gttccaatac ggagaaatcg cggccgcgga gacgcgctcc    360
tgtgacggaa gatcacttcg cagaataaat aaatcctggt gtccctgttg ataccgggaa    420
gccctgggcc aacttttggc gaaatgaga cgttgatcgg cacgtaagag gttccaactt    480
tcaccataat gaataagat cactaccggg cgtattttt gagttatcga gattttcagg    540
agctaaggaa gctaaaatgg agaaaaaaat cactggatat accaccgttg atatatccca    600
atggcatcgt aaagaacatt ttgaggcatt tcagtcagtt gctcaatgta cctataacca    660

```
gaccgttcag ctggatatta cggccttttt aaagaccgta aagaaaaata agcacaagtt      720
ttatccggcc tttattcaca ttcttgcccg cctgatgaat gctcatccgg aattccgtat      780
ggcaatgaaa gacggtgagc tggtgatatg ggatagtgtt caccctggtt acaccgtttt     840
ccatgagcaa actgaaacgt tttcatcgct ctggagtgaa taccacgacg atttccggca      900
gtttctacac atatattcgc aagatgtggc gtgttacggt gaaaacctgg cctatttccc      960
taaagggttt attgagaata tgttttttcgt ctcagccaat ccctgggtga gtttcaccag    1020
ttttgattta aacgtggcca atatggacaa cttcttcgcc cccgttttca ccatgggcaa    1080
atattatacg caaggcgaca aggtgctgat gccgctggcg attcaggttc atcatgccgt    1140
ttgtgatggc ttccatgtcg gcagaatgct taatgaatta acagtact gcgatgagtg      1200 gcagggcggg gcgtaaagcg cgtctccata agtttaaaca aatctttttc gaaaaaggc     1260 cgccccgtta agaggcggcc ttattcaaat tcaggatat gcacttgctt gcaagcttta      1320
ccgttcgtat aatgtatgct atacgaagtt attatttta aaacaatgaa taggtttaca      1380
cttactttag ttttatggaa atgaaagatc atatcatata taatctagaa taaaattaac    1440
taaaataatt attatctaga taaaaaattt agaagccaat gaaatctata aataaactaa    1500
attaagttta tttaattaac aactatggat ataaaatagg tactaatcaa aatagtgagg    1560
aggatatatt tgaatacata cgaacaaatt aataaagtga aaaaaatact tcggaaacat    1620
ttaaaaaata accttattgg tacttacatg tttggatcag gagttgagag tggactaaaa    1680
ccaaatagtg atcttgactt tttagtcgtc gtatctgaac cattgacaga tcaaagtaaa    1740
gaaatactta tacaaaaaat tagacctatt tcaaaaaaaa taggagataa aagcaactta    1800
cgatatattg aattaacaat tattattcag caagaaatgg taccgtggaa tcatcctccc    1860
aaacaagaat ttatttatgg agaatggtta caagagcttt atgaacaagg atacattcct    1920
cagaaggaat taaattcaga tttaaccata atgctttacc aagcaaaacg aaaaaataaa    1980
agaatatacg gaaattatga cttagaggaa ttactacctg atattccatt ttctgatgtg    2040
agaagagcca ttatggattc gtcagaggaa ttaatagata attatcagga tgatgaaacc    2100
aactctatat taactttatg ccgtatgatt ttaactatgg acacgggtaa aatcatacca    2160
aaagatattg cgggaaatgc agtggctgaa tcttctccat agaacatag ggagagaatt     2220 ttgttagcag ttcgtagtta tcttggagag aatattgaat ggactaatga aaatgtaaat    2280
ttaactataa actatttaaa taacagatta aaaaattat aaaaaaattg aaaaaatggt      2340
ggaaacactt ttttcaattt ttttgtttta ttatttaata tttgggaaat attcattata    2400
acttcgtata atgtatgcta tacgaacggt acctgcagga tccgtttagg ctgggcggtg    2460
atagcttctc gttcaggcag tacgcctctt ttcttttcca gacctgaggg aggcggaaat    2520
ggtgtgaggt tcccggggaa aagccaaata ggcgatcgc                           2559
```

<210> SEQ ID NO 10
<211> LENGTH: 39
<212> TYPE: DNA
<213> ORGANISM: artificial sequence
<220> FEATURE:
<223> OTHER INFORMATION: primer

<400> SEQUENCE: 10

```
ccagagctca gcgcgtctcc tatgtttaag tttaaaaag                              39
```

<210> SEQ ID NO 11

```
<211> LENGTH: 48
<212> TYPE: DNA
<213> ORGANISM: artificial sequence
<220> FEATURE:
<223> OTHER INFORMATION: primer

<400> SEQUENCE: 11
ctccaggtac cagcgcgtct ccttattacc acactgttac gttagaac        48

<210> SEQ ID NO 12
<211> LENGTH: 157
<212> TYPE: DNA
<213> ORGANISM: artificial sequence
<220> FEATURE:
<223> OTHER INFORMATION: expression module

<400> SEQUENCE: 12
agcgcgtctc cccgcccaga ctgtccgctg tgtaaaaata aggaataaag ggggttgtt     60 attattttac tgatatgtaa aatataattt gtaagaaa atgagaggga gaggaaatta    120
attaaaaaag gagcgattta catatgggag acgcgct                           157

<210> SEQ ID NO 13
<211> LENGTH: 254
<212> TYPE: DNA
<213> ORGANISM: artificial sequence
<220> FEATURE:
<223> OTHER INFORMATION: expression module

<400> SEQUENCE: 13
taaaaatttt acaaaaaggt attgactttc cctacagggt gtgtaataat ttaattataa     60
ggacaaatga ataaagattg tatccttcgg ggcagggtgg aaatcccgac cggcggtagt   120
aaagcacatt tgctttagag tccgtgaccc gtgtgcataa gcacgcgtg gattcagttt    180 aagctgaagc cgacagtgaa agtctggatg ggagaaggat ggacggtaaa taacaaaaga   240
aaggaggtga tcat                                                    254

<210> SEQ ID NO 14
<211> LENGTH: 283
<212> TYPE: DNA
<213> ORGANISM: artificial sequence
<220> FEATURE:
<223> OTHER INFORMATION: expression module

<400> SEQUENCE: 14
agcgcgtctc cccgctaaaa attttacaaa aaggtattga ctttccctac agggtgtgta     60
ataatttaat tataaggaca aatgaataaa gattgtatcc ttcggggcag gtggaaatc    120 ccgaccggcg gtagtaaagc acatttgctt tagagtccgt gacccgtgtg cataagcacg   180
cggtggattc agtttaagct gaagccgaca gtgaaagtct ggatgggaga aggatggacg   240
gtaaataaca aagaaagga ggtgatcata tgggagacgc gct                     283

<210> SEQ ID NO 15
<211> LENGTH: 170
<212> TYPE: DNA
<213> ORGANISM: artificial sequence
<220> FEATURE:
<223> OTHER INFORMATION: expression module

<400> SEQUENCE: 15
taaaaatttt acaaaaaggt attgactttc cctacagggt gtgtaataat ttaattataa     60
ggacaaatga ataaagattg attttatcga agggcagcac ctgtccttct ccttacactt   120
```

```
tgagggaggt gaacacagac ggtaaataac aaaagagggg agggaaacat            170
```

```
<210> SEQ ID NO 16
<211> LENGTH: 199
<212> TYPE: DNA
<213> ORGANISM: artificial sequence
<220> FEATURE:
<223> OTHER INFORMATION: expression module

<400> SEQUENCE: 16
agcgcgtctc cccgctaaaa attttacaaa aaggtattga ctttccctac agggtgtgta   60
ataatttaat tataaggaca aatgaataaa gattgatttt atcgaagggc agcacctgtc  120
cttctcctta cactttgagg gaggtgaaca cagacggtaa ataacaaaag aggggaggga  180
aacatatggg agacgcgct                                               199
```

```
<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
gggaagcgtt cacagtttcg                                               20
```

```
<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
ggttgccgaa aacaagctaa                                               20
```

```
<210> SEQ ID NO 19
<211> LENGTH: 1977
<212> TYPE: DNA
<213> ORGANISM: Bacillus subtilis

<400> SEQUENCE: 19
atgtttgcaa acgattcaa aacctcttta ctgccgttat tcgctggatt tttattgctg    60
tttcatttgg ttctggcagg accggcggct gcgagtgctg aaacggcgaa caatcgaat   120 gagcttacag caccgtcgat caaaagcgga accattcttc atgcatggaa ttggtcgttc   180
aatacgttaa aacacaatat gaaggatatt catgatgcag gatatacagc cattcagaca   240
tctccgatta accaagtaaa ggaagggaat caaggagata aaagcatgtc gaactggtac   300
tggctgtatc agccgacatc gtatcaaatt ggcaaccgtt acttaggtac tgaacaagaa   360
tttaaagaaa tgtgtgcagc cgctgaagaa tatggcataa aggtcattgt tgacgcggtc   420
atcaatcata ccaccagtga ttatgccgcg atttccaatg aggttaagag tattccaaac   480
tggacacatg gaaacacaca aattaaaaac tggtctgatc gatgggatgt cacgcagaat   540
tcattgctcg ggctgtatga ctggaataca caaaatacac aagtacagtc ctatctgaaa   600
cggttcttag acagggcatt gaatgacggg gcagacggtt ttcgatttga tgccgccaaa   660
catatagagc ttccagatga tggcagttac ggcagtcaat tttggccgaa tatcacaaat   720
acatctgcag agttccaata cggagaaatc ctgcaggata gtgcctccag agatgctgca   780
```

```
tatgcgaatt atatggatgt gacagcgtct aactatggc attccataag gtccgcttta      840
aagaatcgta atctgggcgt gtcgaatatc tcccactatg catctgatgt gtctgcggac      900
aagctagtga catgggtaga gtcgcatgat acgtatgcca atgatgatga agagtcgaca      960
tggatgagcg atgatgatat ccgtttaggc tgggcggtga tagcttctcg ttcaggcagt     1020
acgcctcttt tcttttccag acctgaggga ggcggaaatg gtgtgaggtt cccggggaaa     1080
agccaaatag gcgatcgcgg gagtgcttta tttgaagatc aggctatcac tgcggtcaat     1140
agatttcaca atgtgatggc tggacagcct gaggaactct cgaacccgaa tggaaacaac     1200
cagatattta tgaatcagcg cggctcacat ggcgttgtgc tggcaaatgc aggttcatcc     1260
tctgtctcta tcaatacggc aacaaaattg cctgatggca ggtatgacaa taaagctgga     1320
gcgggttcat ttcaagtgaa cgatggtaaa ctgacaggca cgatcaatgc caggtctgta     1380
gctgtgcttt atcctgatga tattgcaaaa gcgcctcatg ttttccttga gaattacaaa     1440
acaggtgtaa cacattcttt caatgatcaa ctgacgatta ccttgcgtgc agatgcgaat     1500
acaacaaaag ccgtttatca aatcaataat ggaccagaga cggcgtttaa ggatggagat     1560
caattcacaa tcggaaaagg agatccattt ggcaaaacat acaccatcat gttaaaagga     1620
acgaacagtg atggtgtaac gaggaccgag aaatacagtt tgttaaaag agatccagcg     1680
tcggccaaaa ccatcggcta tcaaaatccg aatcattgga gccaggtaaa tgcttatatc     1740
tataaacatg atgggagccg agtaattgaa ttgaccggat cttggcctgg aaaaccaatg     1800
actaaaaatg cagacggaat ttacacgctg acgctgcctg cggacacgga tacaaccaac     1860
gcaaaagtga ttttaataa tggcagcgcc caagtgcccg gtcagaatca gcctggcttt     1920
gattacgtgc taaatggttt atataatgac tcgggcttaa gcggttctct tccccat       1977
```

<210> SEQ ID NO 20
<211> LENGTH: 659
<212> TYPE: PRT
<213> ORGANISM: Bacillus subtilis

<400> SEQUENCE: 20

```
Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
                20                  25                  30

Ala Glu Thr Ala Asn Lys Ser Asn Glu Leu Thr Ala Pro Ser Ile Lys
            35                  40                  45

Ser Gly Thr Ile Leu His Ala Trp Asn Trp Ser Phe Asn Thr Leu Lys
        50                  55                  60

His Asn Met Lys Asp Ile His Asp Ala Gly Tyr Thr Ala Ile Gln Thr
65                  70                  75                  80

Ser Pro Ile Asn Gln Val Lys Glu Gly Asn Gln Gly Asp Lys Ser Met
                85                  90                  95

Ser Asn Trp Tyr Trp Leu Tyr Gln Pro Thr Ser Tyr Gln Ile Gly Asn
                100                 105                 110

Arg Tyr Leu Gly Thr Glu Gln Glu Phe Lys Glu Met Cys Ala Ala Ala
            115                 120                 125

Glu Glu Tyr Gly Ile Lys Val Ile Val Asp Ala Val Ile Asn His Thr
        130                 135                 140

Thr Ser Asp Tyr Ala Ala Ile Ser Asn Glu Val Lys Ser Ile Pro Asn
145                 150                 155                 160

Trp Thr His Gly Asn Thr Gln Ile Lys Asn Trp Ser Asp Arg Trp Asp
```

```
            165                 170                 175
Val Thr Gln Asn Ser Leu Leu Gly Leu Tyr Asp Trp Asn Thr Gln Asn
            180                 185                 190

Thr Gln Val Gln Ser Tyr Leu Lys Arg Phe Leu Asp Arg Ala Leu Asn
            195                 200                 205

Asp Gly Ala Asp Gly Phe Arg Phe Asp Ala Ala Lys His Ile Glu Leu
            210                 215                 220

Pro Asp Asp Gly Ser Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                    245                 250                 255

Arg Asp Ala Ala Tyr Ala Asn Tyr Met Asp Val Thr Ala Ser Asn Tyr
                    260                 265                 270

Gly His Ser Ile Arg Ser Ala Leu Lys Asn Arg Asn Leu Gly Val Ser
                    275                 280                 285

Asn Ile Ser His Tyr Ala Ser Asp Val Ser Ala Asp Lys Leu Val Thr
            290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Ala Ser
                    325                 330                 335

Arg Ser Gly Ser Thr Pro Leu Phe Phe Ser Arg Pro Glu Gly Gly Gly
                    340                 345                 350

Asn Gly Val Arg Phe Pro Gly Lys Ser Gln Ile Gly Asp Arg Gly Ser
                    355                 360                 365

Ala Leu Phe Glu Asp Gln Ala Ile Thr Ala Val Asn Arg Phe His Asn
            370                 375                 380

Val Met Ala Gly Gln Pro Glu Glu Leu Ser Asn Pro Asn Gly Asn Asn
385                 390                 395                 400

Gln Ile Phe Met Asn Gln Arg Gly Ser His Gly Val Val Leu Ala Asn
                    405                 410                 415

Ala Gly Ser Ser Ser Val Ser Ile Asn Thr Ala Thr Lys Leu Pro Asp
                    420                 425                 430

Gly Arg Tyr Asp Asn Lys Ala Gly Ala Gly Ser Phe Gln Val Asn Asp
            435                 440                 445

Gly Lys Leu Thr Gly Thr Ile Asn Ala Arg Ser Val Ala Val Leu Tyr
450                 455                 460

Pro Asp Asp Ile Ala Lys Ala Pro His Val Phe Leu Glu Asn Tyr Lys
465                 470                 475                 480

Thr Gly Val Thr His Ser Phe Asn Asp Gln Leu Thr Ile Thr Leu Arg
                    485                 490                 495

Ala Asp Ala Asn Thr Thr Lys Ala Val Tyr Gln Ile Asn Asn Gly Pro
            500                 505                 510

Glu Thr Ala Phe Lys Asp Gly Asp Gln Phe Thr Ile Gly Lys Gly Asp
            515                 520                 525

Pro Phe Gly Lys Thr Tyr Thr Ile Met Leu Lys Gly Thr Asn Ser Asp
530                 535                 540

Gly Val Thr Arg Thr Glu Lys Tyr Ser Phe Val Lys Arg Asp Pro Ala
545                 550                 555                 560

Ser Ala Lys Thr Ile Gly Tyr Gln Asn Pro Asn His Trp Ser Gln Val
                    565                 570                 575

Asn Ala Tyr Ile Tyr Lys His Asp Gly Ser Arg Val Ile Glu Leu Thr
            580                 585                 590
```

```
Gly Ser Trp Pro Gly Lys Pro Met Thr Lys Asn Ala Asp Gly Ile Tyr
        595                 600                 605

Thr Leu Thr Leu Pro Ala Asp Thr Asp Thr Thr Asn Ala Lys Val Ile
        610                 615                 620

Phe Asn Asn Gly Ser Ala Gln Val Pro Gly Gln Asn Gln Pro Gly Phe
625                 630                 635                 640

Asp Tyr Val Leu Asn Gly Leu Tyr Asn Asp Ser Gly Leu Ser Gly Ser
                645                 650                 655

Leu Pro His

<210> SEQ ID NO 21
<211> LENGTH: 36
<212> TYPE: DNA
<213> ORGANISM: artificial sequence
<220> FEATURE:
<223> OTHER INFORMATION: primer

<400> SEQUENCE: 21
ccaaaggcct atgtttgcaa aacgattcaa aacctc                                36

<210> SEQ ID NO 22
<211> LENGTH: 58
<212> TYPE: DNA
<213> ORGANISM: artificial sequence
<220> FEATURE:
<223> OTHER INFORMATION: primer

<400> SEQUENCE: 22
aggtacctct agaagcttac tagtgcggcc gcgatttctc cgtattggaa ctctgcag        58

<210> SEQ ID NO 23
<211> LENGTH: 54
<212> TYPE: DNA
<213> ORGANISM: artificial sequence
<220> FEATURE:
<223> OTHER INFORMATION: primer

<400> SEQUENCE: 23
gcggccgcac tagtaagctt ctagaggtac ctggcgttgt gctggcaaat gcag            54

<210> SEQ ID NO 24
<211> LENGTH: 32
<212> TYPE: DNA
<213> ORGANISM: artificial sequence
<220> FEATURE:
<223> OTHER INFORMATION: primer

<400> SEQUENCE: 24
gtttctcgag atggggaaga gaaccgctta ag                                    32

<210> SEQ ID NO 25
<211> LENGTH: 171
<212> TYPE: DNA
<213> ORGANISM: artificial sequence
<220> FEATURE:
<223> OTHER INFORMATION: primer

<400> SEQUENCE: 25
atcgcggccg cccagactgt ccgctgtgta aaaataagga ataaggggg gttgttatta       60 ttttactgat atgtaaaata taatttgtat aagaaaatga gagggagagg aaattaatta    120
aaaaaggagc gatttacata tgaaaaagaa aacgctttct ttatttgtgg g             171
```

<210> SEQ ID NO 26
<211> LENGTH: 35
<212> TYPE: DNA
<213> ORGANISM: artificial sequence
<220> FEATURE:
<223> OTHER INFORMATION: primer

<400> SEQUENCE: 26

```
taaatataaa agcttgcaag caagtgcata tcctg                                35
```

<210> SEQ ID NO 27
<211> LENGTH: 2440
<212> TYPE: DNA
<213> ORGANISM: Geobacillus stearothermophilus
<220> FEATURE:
<221> NAME/KEY: misc_feature
<223> OTHER INFORMATION: amyM gene

<400> SEQUENCE: 27

```
aattccggcc caacgatggc tgatttccgg gttgacggcc ggcggaacca agggggtgatc      60
ggtcggcgga aatgaaggcc tgcggcgagt gcgggccttc tgttttgagg attataatca     120
gagtatattg aaagtttcgc gatcttttcg tataattgtt ttaggcatag tgcaatcgat     180
tgcattacga aaggagacac acatgcaatg aaaaagaaaa cgctttcttt atttgtggga     240
ctgatgctcc tcatcggtct tctgttcagc ggttctcttc cgtacaatcc aaacgccgct     300
gaagccagca gttccgcaag cgtcaaagga gacgtgattt accagattat cattgaccgg     360
ttttacgatg gggacacgac gaacaacaat cctgccaaaa gttatggact ttacgatccg     420
accaaatcga gtggaaaat gtattggggc ggggatctgg agggggttcg tcaaaaactt     480
ccttatctta aacagctggg cgtaacgaca atctggttgt ccccggtttt ggacaatctg     540
gatacactgg cgggcaccga taacacgggc tatcacggat actggacgcg cgatttttaaa    600
cagattgagg aacatttcgg gaattggacc acatttgaca cgttggtcaa tgatgctcac     660
caaaacggaa tcaaggtgat tgtcgacttt gtgcccaatc attcgactcc ttttaaggca     720
aacgattcca cctttgcgga aggcggcgcc ctctacaaca atggaaccta tatgggcaat     780
tattttgatg acgcaacaaa agggtacttc caccataatg gggacatcag caactgggac     840
gaccggtacg aggcgcaatg gaaaaacttc acggatccag ccggtttctc gcttgccgat     900
ttgtcgcagg aaaatggcac gattgctcaa tacctgaccg atgcggcggt tcaattggta     960
gcacatggag cggatggttt gcggattgat gcggtgaagc atttaattc ggggttctcc    1020
aaatcgttgg ccgataaact gtaccaaaag aaagacattt tcctggtggg ggaatggtac    1080
ggagatgacc ccggaacagc caatcatctg gaaaaggtcc ggtacgccaa caacagcggt    1140
gtcaatgtgc tggattttga tctcaacacg gtgattcgaa atgtgttcgg cacatttacg    1200
caaacgatgt acgatcttaa caatatggtg aaccaaacgg ggaacgagta caaatacaaa    1260
gaaaatctaa tcacatttat cgataaccat gatatgtcaa gatttcttc ggtaaattcg    1320
aacaaggcga atttgcacca ggcgcttgct ttcattctca cttcgcgggg tacgccctcc    1380
atctattatg gaaccgaaca atacatggca ggcggcaatg acccgtacaa ccggggggatg    1440
atgccggcgt tgatacgac aaccaccgcc tttaaagagg tgtcaactct ggcggggttg    1500
cgcaggaaca atgcggcgat ccagtacggc accaccaccc agcgttggat caacaatgat    1560
gtttacattt atgaacggaa attttttcaac gatgtcgtgt tggtggccat caatcgaaac    1620
acgcaatcct cctattcgat ttccggtttg cagacggcct tgccaaatgg cagctatgcg    1680
```

```
gattatctgt cagggctgtt gggggggaac gggatttccg tttccaatgg aagtgtcgct    1740
tcgttcacgc ttgcgcctgg agccgtgtct gtttggcagt acagcacatc cgcttcagcg    1800
ccgcaaatcg gatcggttgc tccaaatatg gggattccgg gtaatgtggt cacgatcgac    1860
gggaaaggtt ttgggacgac gcagggaacc gtgacatttg gcggagtgac agcgactgtg    1920
aaatcctgga catccaatcg gattgaagtg tacgttccca acatggccgc cgggctgacc    1980
gatgtgaaag tcaccgcggg tggagtttcc agcaatctgt attcttacaa tattttgagt    2040
ggaacgcaga catcggttgt gtttactgtg aaaagtgcgc ctccgaccaa cctgggggat    2100
aagatttacc tgacgggcaa cataccggaa ttggggaatt ggagcacgga tacgagcgga    2160
gccgttaaca atgcgcaagg gccccctgctc gcgcccaatt atccggattg gttttatgta    2220
ttcagcgttc cagcaggaaa gacgattcaa ttcaagttct tcatcaagcg tgcggatgga    2280
acgattcaat gggagaatgg ttcgaaccac gtggccacaa ctcccacggg tgcaaccggt    2340
aacattactg ttacgtggca aaactagaaa tctttttcga aaaaaggccg ccccgttaag    2400
aggcggcctt attcaaattt caggatatgc acttgcttgc                          2440
```

<210> SEQ ID NO 28
<211> LENGTH: 719
<212> TYPE: PRT
<213> ORGANISM: Geobacillus stearothermophilus
<220> FEATURE:
<221> NAME/KEY: MISC_FEATURE
<223> OTHER INFORMATION: glucan 1,4-alpha-maltohydrolase protein
      encoded by the amyM gene

<400> SEQUENCE: 28

```
Met Lys Lys Lys Thr Leu Ser Leu Phe Val Gly Leu Met Leu Leu Ile
1               5                   10                  15

Gly Leu Leu Phe Ser Gly Ser Leu Pro Tyr Asn Pro Asn Ala Ala Glu
            20                  25                  30

Ala Ser Ser Ser Ala Ser Val Lys Gly Asp Val Ile Tyr Gln Ile Ile
        35                  40                  45

Ile Asp Arg Phe Tyr Asp Gly Asp Thr Thr Asn Asn Asn Pro Ala Lys
    50                  55                  60

Ser Tyr Gly Leu Tyr Asp Pro Thr Lys Ser Lys Trp Lys Met Tyr Trp
65                  70                  75                  80

Gly Gly Asp Leu Glu Gly Val Arg Gln Lys Leu Pro Tyr Leu Lys Gln
                85                  90                  95

Leu Gly Val Thr Thr Ile Trp Leu Ser Pro Val Leu Asp Asn Leu Asp
            100                 105                 110

Thr Leu Ala Gly Thr Asp Asn Thr Gly Tyr His Gly Tyr Trp Thr Arg
        115                 120                 125

Asp Phe Lys Gln Ile Glu Glu His Phe Gly Asn Trp Thr Thr Phe Asp
    130                 135                 140

Thr Leu Val Asn Asp Ala His Gln Asn Gly Ile Lys Val Ile Val Asp
145                 150                 155                 160

Phe Val Pro Asn His Ser Thr Pro Phe Lys Ala Asn Asp Ser Thr Phe
                165                 170                 175

Ala Glu Gly Gly Ala Leu Tyr Asn Asn Gly Thr Tyr Met Gly Asn Tyr
            180                 185                 190

Phe Asp Asp Ala Thr Lys Gly Tyr Phe His His Asn Gly Asp Ile Ser
        195                 200                 205

Asn Trp Asp Asp Arg Tyr Glu Ala Gln Trp Lys Asn Phe Thr Asp Pro
    210                 215                 220
```

```
Ala Gly Phe Ser Leu Ala Asp Leu Ser Gln Glu Asn Gly Thr Ile Ala
225                 230                 235                 240

Gln Tyr Leu Thr Asp Ala Ala Val Gln Leu Val Ala His Gly Ala Asp
            245                 250                 255

Gly Leu Arg Ile Asp Ala Val Lys His Phe Asn Ser Gly Phe Ser Lys
            260                 265                 270

Ser Leu Ala Asp Lys Leu Tyr Gln Lys Lys Asp Ile Phe Leu Val Gly
        275                 280                 285

Glu Trp Tyr Gly Asp Asp Pro Gly Thr Ala Asn His Leu Glu Lys Val
    290                 295                 300

Arg Tyr Ala Asn Asn Ser Gly Val Asn Val Leu Asp Phe Asp Leu Asn
305                 310                 315                 320

Thr Val Ile Arg Asn Val Phe Gly Thr Phe Thr Gln Thr Met Tyr Asp
                325                 330                 335

Leu Asn Asn Met Val Asn Gln Thr Gly Asn Glu Tyr Lys Tyr Lys Glu
            340                 345                 350

Asn Leu Ile Thr Phe Ile Asp Asn His Asp Met Ser Arg Phe Leu Ser
        355                 360                 365

Val Asn Ser Asn Lys Ala Asn Leu His Gln Ala Leu Ala Phe Ile Leu
    370                 375                 380

Thr Ser Arg Gly Thr Pro Ser Ile Tyr Tyr Gly Thr Glu Gln Tyr Met
385                 390                 395                 400

Ala Gly Gly Asn Asp Pro Tyr Asn Arg Gly Met Met Pro Ala Phe Asp
                405                 410                 415

Thr Thr Thr Thr Ala Phe Lys Glu Val Ser Thr Leu Ala Gly Leu Arg
            420                 425                 430

Arg Asn Asn Ala Ala Ile Gln Tyr Gly Thr Thr Thr Gln Arg Trp Ile
        435                 440                 445

Asn Asn Asp Val Tyr Ile Tyr Glu Arg Lys Phe Phe Asn Asp Val Val
    450                 455                 460

Leu Val Ala Ile Asn Arg Asn Thr Gln Ser Ser Tyr Ser Ile Ser Gly
465                 470                 475                 480

Leu Gln Thr Ala Leu Pro Asn Gly Ser Tyr Ala Asp Tyr Leu Ser Gly
                485                 490                 495

Leu Leu Gly Gly Asn Gly Ile Ser Val Ser Asn Gly Ser Val Ala Ser
            500                 505                 510

Phe Thr Leu Ala Pro Gly Ala Val Ser Val Trp Gln Tyr Ser Thr Ser
        515                 520                 525

Ala Ser Ala Pro Gln Ile Gly Ser Val Ala Pro Asn Met Gly Ile Pro
    530                 535                 540

Gly Asn Val Val Thr Ile Asp Gly Lys Gly Phe Gly Thr Thr Gln Gly
545                 550                 555                 560

Thr Val Thr Phe Gly Gly Val Thr Ala Thr Val Lys Ser Trp Thr Ser
                565                 570                 575

Asn Arg Ile Glu Val Tyr Val Pro Asn Met Ala Ala Gly Leu Thr Asp
            580                 585                 590

Val Lys Val Thr Ala Gly Gly Val Ser Ser Asn Leu Tyr Ser Tyr Asn
        595                 600                 605

Ile Leu Ser Gly Thr Gln Thr Ser Val Val Phe Thr Val Lys Ser Ala
    610                 615                 620

Pro Pro Thr Asn Leu Gly Asp Lys Ile Tyr Leu Thr Gly Asn Ile Pro
625                 630                 635                 640
```

```
Glu Leu Gly Asn Trp Ser Thr Asp Thr Ser Gly Ala Val Asn Asn Ala
                645                 650                 655

Gln Gly Pro Leu Leu Ala Pro Asn Tyr Pro Asp Trp Phe Tyr Val Phe
            660                 665                 670

Ser Val Pro Ala Gly Lys Thr Ile Gln Phe Lys Phe Phe Ile Lys Arg
        675                 680                 685

Ala Asp Gly Thr Ile Gln Trp Glu Asn Gly Ser Asn His Val Ala Thr
    690                 695                 700

Thr Pro Thr Gly Ala Thr Gly Asn Ile Thr Val Thr Trp Gln Asn
705                 710                 715

<210> SEQ ID NO 29
<211> LENGTH: 102
<212> TYPE: DNA
<213> ORGANISM: artificial sequence
<220> FEATURE:
<223> OTHER INFORMATION: expression module

<400> SEQUENCE: 29
gcggccgcag aaatgggcgt gaaaaaaagc gcgcgattat gtaaaatata aagtgatagc      60
ggtaccatta tagttaatta aaaaaggagc gatttacata tg                        102

<210> SEQ ID NO 30
<211> LENGTH: 232
<212> TYPE: DNA
<213> ORGANISM: artificial sequence
<220> FEATURE:
<223> OTHER INFORMATION: expression module

<400> SEQUENCE: 30
gcggccgcga gagcaaagaa aaagccagcg gggaagctgg atggaaagaa acaaagtcgg      60
ttttcactaa aagaaagcac gggtgtttga aaaacccgtg ctttttttgtt gcggttagcc    120 gaaattcgac aattgcggtt attttgcgtt cttcttttttc ttgtaaatat gataaaatat    180
gacatatctc gggtaattca aaattaatta aaaaaggagc gatttacata tg             232

<210> SEQ ID NO 31
<211> LENGTH: 129
<212> TYPE: DNA
<213> ORGANISM: artificial sequence
<220> FEATURE:
<223> OTHER INFORMATION: expression module

<400> SEQUENCE: 31
gcggccgcgc taaaattcct gaaaattttt gcaaaaagtt gttgacttta tctacaaggt     60
gtggcataat aatcttaaag aaaatgagag ggagaggaaa ttaattaaaa aaggagcgat    120
ttacatatg                                                            129

<210> SEQ ID NO 32
<211> LENGTH: 204
<212> TYPE: DNA
<213> ORGANISM: artificial sequence
<220> FEATURE:
<223> OTHER INFORMATION: expression module

<400> SEQUENCE: 32
gcggccgcat ccacgctgtg taaaattttt acaaaaaggt attgactttc cctacagggt      60
gtgtaataat ttaattaaga tctgctaaaa ttcctgaaaa attttgcaaa agttgttga     120 ctttatctac aaggtgtggc ataataatct taaagaaaat gagagggaga ggaaattaat    180
```

```
taaaaaagga gcgatttaca tatg                                               204

<210> SEQ ID NO 33
<211> LENGTH: 129
<212> TYPE: DNA
<213> ORGANISM: artificial sequence
<220> FEATURE:
<223> OTHER INFORMATION: expression module

<400> SEQUENCE: 33
gcggccgcat ccacgctgtg taaaaatttt acaaaaaggt attgactttc cctacagggt        60
gtgtaataat ttaattaaag aaaatgagag ggagaggaaa ttaattaaaa aaggagcgat       120
ttacatatg                                                               129

<210> SEQ ID NO 34
<211> LENGTH: 265
<212> TYPE: DNA
<213> ORGANISM: artificial sequence
<220> FEATURE:
<223> OTHER INFORMATION: expression module

<400> SEQUENCE: 34
gcggccgcta aaatttttac aaaaaggtat tgactttccc tacagggtgt gtaataattt        60
aattataagg acaaatgaat aaagattgta tccttcgggg cagggtggaa atcccgaccg       120
gcggtagtaa agcacatttg ctttagagtc cgtgacccgt gtgcataagc acgcggtgga       180
ttcagtttaa gctgaagccg acagtgaaag tctggatggg agaaggatgg acggtaaata       240
acaaaagaaa ggaggtgatc atatg                                             265

<210> SEQ ID NO 35
<211> LENGTH: 181
<212> TYPE: DNA
<213> ORGANISM: artificial sequence
<220> FEATURE:
<223> OTHER INFORMATION: expression module

<400> SEQUENCE: 35
gcggccgcta aaatttttac aaaaaggtat tgactttccc tacagggtgt gtaataattt        60
aattataagg acaaatgaat aaagattgat tttatcgaag gcagcacct gtccttctcc       120 ttacactttg agggaggtga acacagacgg taaataacaa agaggggag ggaaacatat       180 g                                                                       181

<210> SEQ ID NO 36
<211> LENGTH: 29
<212> TYPE: DNA
<213> ORGANISM: Bacteriophage SPO1

<400> SEQUENCE: 36
ttgactttcc ctacagggtg tgtaataat                                          29

<210> SEQ ID NO 37
<211> LENGTH: 23
<212> TYPE: DNA
<213> ORGANISM: artificial sequence
<220> FEATURE:
<223> OTHER INFORMATION: primer

<400> SEQUENCE: 37
ttttgactcc gaagtaagtc ttc                                                23
```

```
<210> SEQ ID NO 38
<211> LENGTH: 23
<212> TYPE: DNA
<213> ORGANISM: artificial sequence
<220> FEATURE:
<223> OTHER INFORMATION: primer

<400> SEQUENCE: 38
atggtttctt tcggtaagtc ccg                                          23

<210> SEQ ID NO 39
<211> LENGTH: 2370
<212> TYPE: DNA
<213> ORGANISM: Bacillus subtilis

<400> SEQUENCE: 39
atgagtgtgg caaagaaaaa acgaaaatca agaaaaaaac aggcgaaaca gctcaatata    60
aaatacgagc tcaacggatt gctgtgtata gccatttcaa ttatcgcaat cttgcagctg   120
ggggtagtcg ggcaaacgtt tatctatttg ttccgctttt ttgctggaga gtggtttatt   180
ttatgcttgt taggtttatt ggtgttagga gtctcactgt tttggaagaa aaaaacccca   240
agccttttaa cgagacgaaa ggccggggtg tactgtatta tcgcaagcat attgctgctt   300
tctcacgtgc agctatttaa aaatttgacg cacaaagggt ctattgagtc tgcaagcgtg   360
gtgcgcaata cgtgggaatt gttttttaatg gacatgaatg gcagctctgc ttcacctgat   420
ttaggcggag ggatgatcgg tgcgctgctg tttgcggctt cacactttt tgtttgcgtcg   480 actggttctc agatcatggc aattgtcatg attttgatcg gaatgatttt agtaacagga   540
cgctcgctgc aagaaacgct aaaaagtgg atgagcccga ttggacgttt tataaaagaa   600
caatggttag catttattga tgacatgaaa tccttcaaat caaatatgca gtcatcgaaa   660
aaaacgaaag cgccgagcaa aaaacaaaaa ccggcccgca aaaacagca atggaaccg    720 gagcctcctg atgaagaggg ggattatgaa acagtatcgc ctcttattca ttcagagccg   780
attatctcaa gcttttctga tcgtaatgaa gaggaagagt ctccagttat agaaaagcgc   840
gccgaacctg tgtcgaagcc gcttcaggac atccaaccgg agacaggtga tcaggaaact   900
gtttctgctc ctcctatgac ctttacagag ctcgaaaata aggattacga gatgccgtca   960
ctggatttgc tggcagatcc gaagcatacc ggccagcagg ctgataaaaa gaatatttat  1020
gaaaatgcga gaaagcttga acgcacattc caaagctttg gcgtaaaggc gaaagtcaca  1080
caggttcatc tcggaccggc cgtaacaaaa tatgaagtat atcctgatgt cggagtgaag  1140
gttagcaaaa ttgtcaattt aagcgatgat ttagcgcttg cgcttgctgc gaaggatatc  1200
aggatcgaag cgcctatacc aggcaaatca gcaatcggaa ttgaagttcc aaacgcagaa  1260
gtggcaatgg tttcgctgaa agaagtgctg gagtctaaat tgaatgacag accggatgcg  1320
aagctgttaa ttggactcgg ccgcaatatt tcaggtgaag ctgtattggc tgagttaaac  1380
aagatgcccc accttttggt cgcaggcgca accggtagcg ggaaaagtgt ctgtgtcaac  1440
ggcattatta caagtatttt aatgcgggcg aaaccgcatg aagtgaaaat gatgatgatc  1500
gatcctaaaa tggtagagct aaatgtctac aacgggattc cgcatttgct tgctcctgtt  1560
gtaaccgatc cgaaaaaagc gtcgcaggct ttgaaaaagg ttgtcaatga atggagcgg   1620 cggtacgaat tattttctca tacgggtaca agaaatattg aaggatacaa tgattatata  1680
aaacgcgcca acaatgaaga aggagcgaaa cagccgagc tgccttatat tgttgtcatt  1740
gtggacgagc tagccgatct catgatggtc gcttcatctg atgtggaaga ttcgattacg  1800
```

-continued

```
agattgtccc aaatggcgcg ggctgccggc atccatctta ttattgcgac acagcggcca   1860
tcggtggatg ttatcacagg ggtgatcaaa gcgaacattc cgtcacgaat cgcgttcagc   1920
gtatcttcac agacggattc aaggaccatt cttgacatgg gtggcgctga aagcttctt    1980
ggccgcggcg atatgctgtt tttacctgta ggggctaaca aacctgtccg tgtgcaggga   2040
gcatttttgt cggatgacga agtggagaag gtcgtcgacc atgtgattac tcagcagaaa   2100
gcgcaatatc aagaagaaat gattcctgag gagacgacgg aaactcattc cgaggttact   2160
gatgaacttt atgatgaagc tgttgaatta atcgtcggca tgcagacggc atctgtttca   2220
atgctgcaaa gaagattcag aattggctat acgagagcgg cgcgcctgat tgacgcaatg   2280
gaggaacgcg gtgttgtcgg accgtatgaa ggcagcaaac ctagggaagt attattatca   2340
aaagagaaat atgatgagct ctcttcttaa                                    2370
```

<210> SEQ ID NO 40
<211> LENGTH: 789
<212> TYPE: PRT
<213> ORGANISM: Bacillus subtilis

<400> SEQUENCE: 40

```
Met Ser Val Ala Lys Lys Arg Lys Ser Arg Lys Lys Gln Ala Lys
1               5                   10                  15

Gln Leu Asn Ile Lys Tyr Glu Leu Asn Gly Leu Leu Cys Ile Ala Ile
            20                  25                  30

Ser Ile Ile Ala Ile Leu Gln Leu Gly Val Val Gly Gln Thr Phe Ile
            35                  40                  45

Tyr Leu Phe Arg Phe Phe Ala Gly Glu Trp Phe Ile Leu Cys Leu Leu
        50                  55                  60

Gly Leu Leu Val Leu Gly Val Ser Leu Phe Trp Lys Lys Lys Thr Pro
65                  70                  75                  80

Ser Leu Leu Thr Arg Arg Lys Ala Gly Leu Tyr Cys Ile Ile Ala Ser
                85                  90                  95

Ile Leu Leu Leu Ser His Val Gln Leu Phe Lys Asn Leu Thr His Lys
            100                 105                 110

Gly Ser Ile Glu Ser Ala Ser Val Val Arg Asn Thr Trp Glu Leu Phe
        115                 120                 125

Leu Met Asp Met Asn Gly Ser Ser Ala Ser Pro Asp Leu Gly Gly Gly
    130                 135                 140

Met Ile Gly Ala Leu Leu Phe Ala Ala Ser His Phe Leu Phe Ala Ser
145                 150                 155                 160

Thr Gly Ser Gln Ile Met Ala Ile Val Met Ile Leu Ile Gly Met Ile
                165                 170                 175

Leu Val Thr Gly Arg Ser Leu Gln Glu Thr Leu Lys Lys Trp Met Ser
            180                 185                 190

Pro Ile Gly Arg Phe Ile Lys Glu Gln Trp Leu Ala Phe Ile Asp Asp
        195                 200                 205

Met Lys Ser Phe Lys Ser Asn Met Gln Ser Lys Lys Thr Lys Ala
    210                 215                 220

Pro Ser Lys Lys Gln Lys Pro Ala Arg Lys Lys Gln Gln Met Glu Pro
225                 230                 235                 240

Glu Pro Pro Asp Glu Glu Gly Asp Tyr Glu Thr Val Ser Pro Leu Ile
                245                 250                 255

His Ser Glu Pro Ile Ile Ser Ser Phe Ser Asp Arg Asn Glu Glu Glu
            260                 265                 270
```

```
Glu Ser Pro Val Ile Glu Lys Arg Ala Glu Pro Val Ser Lys Pro Leu
        275                 280                 285

Gln Asp Ile Gln Pro Gly Thr Gly Asp Gln Glu Thr Val Ser Ala Pro
    290                 295                 300

Pro Met Thr Phe Thr Glu Leu Glu Asn Lys Asp Tyr Glu Met Pro Ser
305                 310                 315                 320

Leu Asp Leu Leu Ala Asp Pro Lys His Thr Gly Gln Gln Ala Asp Lys
                325                 330                 335

Lys Asn Ile Tyr Glu Asn Ala Arg Lys Leu Glu Arg Thr Phe Gln Ser
            340                 345                 350

Phe Gly Val Lys Ala Lys Val Thr Gln Val His Leu Gly Pro Ala Val
        355                 360                 365

Thr Lys Tyr Glu Val Tyr Pro Asp Val Gly Val Lys Val Ser Lys Ile
    370                 375                 380

Val Asn Leu Ser Asp Asp Leu Ala Leu Ala Leu Ala Ala Lys Asp Ile
385                 390                 395                 400

Arg Ile Glu Ala Pro Ile Pro Gly Lys Ser Ala Ile Gly Ile Glu Val
                405                 410                 415

Pro Asn Ala Glu Val Ala Met Val Ser Leu Lys Glu Val Leu Glu Ser
            420                 425                 430

Lys Leu Asn Asp Arg Pro Asp Ala Lys Leu Leu Ile Gly Leu Gly Arg
        435                 440                 445

Asn Ile Ser Gly Glu Ala Val Leu Ala Glu Leu Asn Lys Met Pro His
    450                 455                 460

Leu Leu Val Ala Gly Ala Thr Gly Ser Gly Lys Ser Val Cys Val Asn
465                 470                 475                 480

Gly Ile Ile Thr Ser Ile Leu Met Arg Ala Lys Pro His Glu Val Lys
                485                 490                 495

Met Met Met Ile Asp Pro Lys Met Val Glu Leu Asn Val Tyr Asn Gly
            500                 505                 510

Ile Pro His Leu Leu Ala Pro Val Val Thr Asp Pro Lys Lys Ala Ser
        515                 520                 525

Gln Ala Leu Lys Lys Val Val Asn Glu Met Glu Arg Arg Tyr Glu Leu
    530                 535                 540

Phe Ser His Thr Gly Thr Arg Asn Ile Glu Gly Tyr Asn Asp Tyr Ile
545                 550                 555                 560

Lys Arg Ala Asn Asn Glu Glu Gly Ala Lys Gln Pro Glu Leu Pro Tyr
                565                 570                 575

Ile Val Val Ile Val Asp Glu Leu Ala Asp Leu Met Met Val Ala Ser
            580                 585                 590

Ser Asp Val Glu Asp Ser Ile Thr Arg Leu Ser Gln Met Ala Arg Ala
        595                 600                 605

Ala Gly Ile His Leu Ile Ile Ala Thr Gln Arg Pro Ser Val Asp Val
    610                 615                 620

Ile Thr Gly Val Ile Lys Ala Asn Ile Pro Ser Arg Ile Ala Phe Ser
625                 630                 635                 640

Val Ser Ser Gln Thr Asp Ser Arg Thr Ile Leu Asp Met Gly Gly Ala
                645                 650                 655

Glu Lys Leu Leu Gly Arg Gly Asp Met Leu Phe Leu Pro Val Gly Ala
            660                 665                 670

Asn Lys Pro Val Arg Val Gln Gly Ala Phe Leu Ser Asp Asp Glu Val
        675                 680                 685

Glu Lys Val Val Asp His Val Ile Thr Gln Gln Lys Ala Gln Tyr Gln
```

```
                690              695              700
Glu Glu Met Ile Pro Glu Glu Thr Thr Glu Thr His Ser Glu Val Thr
705                 710                 715                 720

Asp Glu Leu Tyr Asp Glu Ala Val Glu Leu Ile Val Gly Met Gln Thr
                725                 730                 735

Ala Ser Val Ser Met Leu Gln Arg Arg Phe Arg Ile Gly Tyr Thr Arg
                740                 745                 750

Ala Ala Arg Leu Ile Asp Ala Met Glu Glu Arg Gly Val Val Gly Pro
                755                 760                 765

Tyr Glu Gly Ser Lys Pro Arg Glu Val Leu Leu Ser Lys Glu Lys Tyr
                770                 775                 780

Asp Glu Leu Ser Ser
785

<210> SEQ ID NO 41
<211> LENGTH: 639
<212> TYPE: DNA
<213> ORGANISM: Bacillus subtilis

<400> SEQUENCE: 41
atgtttaagt ttaaaaagaa tttcttagtt ggattatcgg cagctttaat gagtattagc      60
ttgttttcgg caaccgcctc tgcagctagc acagactact ggcaaaattg gactgatggg     120
ggcggtatag taaacgctgt caatgggtct ggcgggaatt acagtgttaa ttggtctaat     180
accggaaatt tgttgttggt aaaggttgg actacaggtt cgccatttag gacgataaac     240
tataatgccg gagtttgggc gccgaatggc aatggatatt taactttata tggttggacg     300
agatcacctc tcatagaata ttatgtagtg gattcatggg gtacttatag acctactgga     360
acgtataaag gtactgtaaa aagtgatggg ggtacatatg acatatatac aactacacgt     420
tataacgcac cttccattga tggcgatcgc actactttta cgcagtactg gagtgttcgc     480
cagtcgaaga gaccaaccgg aagcaacgct acaatcactt tcagcaatca tgtgaacgca     540
tggaagagcc atggaatgaa tctgggcagt aattgggctt accaagtcat ggcgacagaa     600
ggatatcaaa gtagtggaag ttctaacgta acagtgtgg                           639

<210> SEQ ID NO 42
<211> LENGTH: 1566
<212> TYPE: DNA
<213> ORGANISM: Bacillus amyloliquefaciens

<400> SEQUENCE: 42
gtgggtttag gtaagaaatt gtctgttgct gtcgccgctt cctttatgag tttaaccatc      60
agtctgccgg tgttcaggc cgctgagaat cctcagctta agaaaaacct gacgaatttt     120
gtaccgaagc attctttggt gcaatcagaa ttgccttctg tcagtgacaa agctatcaag     180
caatacttga acaaaacgg caaagtcttt aaaggcaatc cttctgaaag attgaagctg     240
attgaccaaa cgaccgatga tctcggctac aagcacttcc gttatgtgcc tgtcgtaaac     300
ggtgtgcctg tgaaagactc tcaagtcatt attcacgtcg ataaatccaa caacgtctat     360
gcgattaacg tgaattaaa caacgatgtt tccgccaaaa cggcaaacag caaaaaatta     420
tctgcaaatc aggcgctgga tcatgcttat aaagcgatcg gcaaatcacc tgaagccgtt     480
tctaacggaa ccgttgcaaa caaaacaaa gccgagctga agcagcagc cacaaaagac     540 ggcaaatacc gcctcgccta tgatgtaacc atccgctaca tcgaaccgga acctgcaaac     600
tgggaagtaa ccgttgatgc ggaaacagga aaaatcctga aaagcaaaa caaagtggag     660
```

```
catgccgcca caaccggaac aggtacgact cttaaaggaa aaacggtctc attaaatatt    720
tcttctgaaa gcggcaaata tgtgctgcgc gatctttcta aacctaccgg aacacaaatt    780
attacgtacg atctgcaaaa ccgcgagtat aacctgccgg gcacactcgt atccagcacc    840
acaaaccagt ttacaacttc ttctcagcgc gctgccgttg atgcgcatta caacctcggc    900
aaagtgtatg attatttcta tcagaagttt aatcgcaaca gctacgacaa taaaggcggc    960
aagatcgtat cctccgttca ttacggcagc agatacaata acgcagcctg gatcggcgac   1020
caaatgattt acggtgacgg cgacggttca ttcttctcac ctctttccgg ttcaatggac   1080
gtaaccgctc atgaaatgac acatggcgtt acacaggaaa cagccaacct gaactacgaa   1140
aatcagccgg gcgctttaaa cgaatccttc tctgatgtat tcgggtactt caacgatact   1200
gaggactggg atatcggtga agatattacg gtcagccagc cggctctccg cagcttatcc   1260
aatccgacaa aatacggaca gcctgataat ttcaaaaatt acaaaaacct tccgaacact   1320
gatgccggcg actacggcgg cgtgcataca aacagcggaa tcccgaacaa agccgcttac   1380
aatacgatta caaaaatcgg cgtgaacaaa gcggagcaga tttactatcg tgctctgacg   1440
gtatacctca ctccgtcatc aacttttaaa gatgcaaaag ccgctttgat tcaatctgcg   1500
cgggaccttt acggctctca agatgctgca agcgtagaag ctgcctggaa tgcagtcgga   1560
ttgtaa                                                              1566

<210> SEQ ID NO 43
<211> LENGTH: 521
<212> TYPE: PRT
<213> ORGANISM: Bacillus amyloliquefaciens

<400> SEQUENCE: 43

Val Gly Leu Gly Lys Lys Leu Ser Val Ala Val Ala Ala Ser Phe Met
1               5                   10                  15

Ser Leu Thr Ile Ser Leu Pro Gly Val Gln Ala Ala Glu Asn Pro Gln
            20                  25                  30

Leu Lys Glu Asn Leu Thr Asn Phe Val Pro Lys His Ser Leu Val Gln
        35                  40                  45

Ser Glu Leu Pro Ser Val Ser Asp Lys Ala Ile Lys Gln Tyr Leu Lys
    50                  55                  60

Gln Asn Gly Lys Val Phe Lys Gly Asn Pro Ser Glu Arg Leu Lys Leu
65                  70                  75                  80

Ile Asp Gln Thr Thr Asp Asp Leu Gly Tyr Lys His Phe Arg Tyr Val
                85                  90                  95

Pro Val Val Asn Gly Val Pro Val Lys Asp Ser Gln Val Ile Ile His
            100                 105                 110

Val Asp Lys Ser Asn Asn Val Tyr Ala Ile Asn Gly Glu Leu Asn Asn
        115                 120                 125

Asp Val Ser Ala Lys Thr Ala Asn Ser Lys Lys Leu Ser Ala Asn Gln
    130                 135                 140

Ala Leu Asp His Ala Tyr Lys Ala Ile Gly Lys Ser Pro Glu Ala Val
145                 150                 155                 160

Ser Asn Gly Thr Val Ala Asn Lys Asn Lys Ala Glu Leu Lys Ala Ala
                165                 170                 175

Ala Thr Lys Asp Gly Lys Tyr Arg Leu Ala Tyr Asp Val Thr Ile Arg
            180                 185                 190

Tyr Ile Glu Pro Glu Pro Ala Asn Trp Glu Val Thr Val Asp Ala Glu
        195                 200                 205
```

```
Thr Gly Lys Ile Leu Lys Lys Gln Asn Lys Val Glu His Ala Ala Thr
    210                 215                 220
Thr Gly Thr Gly Thr Thr Leu Lys Gly Lys Thr Val Ser Leu Asn Ile
225                 230                 235                 240
Ser Ser Glu Ser Gly Lys Tyr Val Leu Arg Asp Leu Ser Lys Pro Thr
                245                 250                 255
Gly Thr Gln Ile Ile Thr Tyr Asp Leu Gln Asn Arg Glu Tyr Asn Leu
            260                 265                 270
Pro Gly Thr Leu Val Ser Ser Thr Asn Gln Phe Thr Thr Ser Ser
        275                 280                 285
Gln Arg Ala Ala Val Asp Ala His Tyr Asn Leu Gly Lys Val Tyr Asp
    290                 295                 300
Tyr Phe Tyr Gln Lys Phe Asn Arg Asn Ser Tyr Asp Asn Lys Gly Gly
305                 310                 315                 320
Lys Ile Val Ser Ser Val His Tyr Gly Ser Arg Tyr Asn Asn Ala Ala
                325                 330                 335
Trp Ile Gly Asp Gln Met Ile Tyr Gly Asp Gly Asp Gly Ser Phe Phe
            340                 345                 350
Ser Pro Leu Ser Gly Ser Met Asp Val Thr Ala His Glu Met Thr His
        355                 360                 365
Gly Val Thr Gln Glu Thr Ala Asn Leu Asn Tyr Glu Asn Gln Pro Gly
    370                 375                 380
Ala Leu Asn Glu Ser Phe Ser Asp Val Phe Gly Tyr Phe Asn Asp Thr
385                 390                 395                 400
Glu Asp Trp Asp Ile Gly Glu Asp Ile Thr Val Ser Gln Pro Ala Leu
                405                 410                 415
Arg Ser Leu Ser Asn Pro Thr Lys Tyr Gly Gln Pro Asp Asn Phe Lys
            420                 425                 430
Asn Tyr Lys Asn Leu Pro Asn Thr Asp Ala Gly Asp Tyr Gly Gly Val
        435                 440                 445
His Thr Asn Ser Gly Ile Pro Asn Lys Ala Ala Tyr Asn Thr Ile Thr
    450                 455                 460
Lys Ile Gly Val Asn Lys Ala Glu Gln Ile Tyr Tyr Arg Ala Leu Thr
465                 470                 475                 480
Val Tyr Leu Thr Pro Ser Ser Thr Phe Lys Asp Ala Lys Ala Ala Leu
                485                 490                 495
Ile Gln Ser Ala Arg Asp Leu Tyr Gly Ser Gln Asp Ala Ala Ser Val
            500                 505                 510
Glu Ala Ala Trp Asn Ala Val Gly Leu
        515                 520

<210> SEQ ID NO 44
<211> LENGTH: 1149
<212> TYPE: DNA
<213> ORGANISM: Bacillus amyloliquefaciens

<400> SEQUENCE: 44
gtgagaggca aaaagtatg  gatcagtttg ctgtttgctt tagcgttaat ctttacgatg      60
gcgttcggca gcacatcctc tgcccaggcg gcagggaaat caaacgggga aagaaatat     120 attgtcgggt ttaaacagac aatgagcacg atgagcgccg ctaagaagaa agatgtcatt    180
tctgaaaaag gcgggaaagt gcaaaagcaa ttcaaatatg tagacgcagc ttcagctaca    240
ttaaacgaaa aagctgtaaa agaattgaaa aaagacccga gcgtcgctta cgttgaagaa    300
```

```
gatcacgtag cacatgcgta cgcgcagtcc gtgccttacg gcgtatcaca aattaaagcc      360
cctgctctgc actctcaagg ctacactgga tcaaatgtta agtagcggt tatcgacagc       420
ggtatcgatt cttctcatcc tgatttaaag gtagcaggcg gagccagcat ggttccttct      480
gaaacaaatc ctttccaaga caacaactct cacggaactc acgttgccgg cacagttgcg      540
gctcttaata actcaatcgg tgtattaggc gttgcgccaa gcgcatcact ttacgctgta      600
aaagttctcg gtgctgacgg ttccggccaa tacagctgga tcattaacgg aatcgagtgg      660
gcgatcgcaa acaatatgga cgttattaac atgagcctcg gcggaccttc tggttctgct      720
gctttaaaag cggcagttga taaagccgtt gcatccggcg tcgtagtcgt tgcggcagcc      780
ggtaacgaag gcacttccgg cagctcaagc acagtgggct accctggtaa ataccctcct      840
gtcattgcag taggcgctgt tgacagcagc aaccaaagag catctttctc aagcgtagga      900
cctgagcttg atgtcatggc acctggcgta tctatccaaa gcacgcttcc tggaaacaaa      960
tacggggcgt acaacggtac gtcaatggca tctccgcacg ttgccggagc ggctgctttg     1020
attctttcta agcacccgaa ctggacaaac actcaagtcc gcagcagttt agaaaacacc     1080
actacaaaac ttggtgattc tttctactat ggaaaagggc tgatcaacgt acaggcggca     1140
gctcagtaa                                                              1149
```

<210> SEQ ID NO 45
<211> LENGTH: 382
<212> TYPE: PRT
<213> ORGANISM: Bacillus amyloliquefaciens

<400> SEQUENCE: 45

```
Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220
```

```
Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
        290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
                340                 345                 350

Val Arg Ser Ser Leu Glu Asn Thr Thr Lys Leu Gly Asp Ser Phe
                355                 360                 365

Tyr Tyr Gly Lys Gly Leu Ile Asn Val Gln Ala Ala Gln
370                 375                 380

<210> SEQ ID NO 46
<211> LENGTH: 1140
<212> TYPE: DNA
<213> ORGANISM: Bacillus licheniformis

<400> SEQUENCE: 46
atgatgagga aaaagagttt ttggcttggg atgctgacgg ccttaatgct cgtgttcacg      60
atggccttca gcgattccgc gtctgctgct cagccggcga aaaatgttga aaaggattat     120
attgtcggat ttaagtcggg agtgaaaacc gcatccgtca aaaaggacat catcaaagag     180
agcggcggaa aagtggacaa gcagtttaga atcatcaacg cggcaaaagc gaagctagac     240
aaagaagcgc ttgaggaagt caaaaatgat ccggatgtcg cttatgtgga agaggatcac     300
gtagctcatg ctttggcgca aaccgttcct tacggcattc ctctcattaa agcggacaaa     360
gtgcaggctc aaggctacaa gggagcgaac gtaaaagtcg ccgtcctgga tacaggaatc     420
caagcttctc atccggactt gaacgtagtc ggcgagcaa gcttcgtagc tggcgaagct     480
tataacaccg acggcaacgg acacggcacg catgttgccg gtacagtagc tgcgcttgac     540
aatacaacgg tgtattaggc gttgcgccg aacgtatcct tgtacgcggt taaagtgctg     600
aattcaagcg gaagcggatc ttacagcggc attgtaagcg gaatcgagtg ggcgacgaca     660
aacggcatgg atgttatcaa catgagcctt ggaggaccat caggctcaac agcgatgaaa     720
caggcggttg acaatgcata tgcaagaggg gttgtcgttg tggcggctgc tgggaacagc     780
ggatcttcag gaaacacgaa tacaatcggc tatcctgcga aatacgactc tgtcatcgca     840
gttggcgcgg tagactctaa cagcaacaga gcttcatttt ccagcgtcgg agcagagctt     900
gaagtcatgg ctcctggcgc aggcgtgtac agcacttacc caaccagcac ttatgcaaca     960
ttgaacggaa cgtcaatggc ttctcctcat gtagcgggag cagcagcttt gatcttgtca    1020
aaacatccga acctttcagc ttcacaagtc cgcaaccgtc tctccagtac ggcgacttat    1080
ttgggaagct ccttctacta tggaaaaggt ctgatcaatg tcgaagctgc cgctcaataa    1140

<210> SEQ ID NO 47
```

<211> LENGTH: 379
<212> TYPE: PRT
<213> ORGANISM: Bacillus licheniformis

<400> SEQUENCE: 47

```
Met Met Arg Lys Lys Ser Phe Trp Leu Gly Met Leu Thr Ala Leu Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Glu Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Tyr Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Asn Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Ser Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Gln
    370                 375
```

```
<210> SEQ ID NO 48
<211> LENGTH: 41
<212> TYPE: DNA
<213> ORGANISM: Bacillus subtilis

<400> SEQUENCE: 48
acagaatagt cttttaagta agtctactct gaattttttt a                 41

<210> SEQ ID NO 49
<211> LENGTH: 57
<212> TYPE: DNA
<213> ORGANISM: Bacillus subtilis

<400> SEQUENCE: 49
attttatcga agggcagcac ctgtccttct ccttacactt tgagggaggt gaacaca  57

<210> SEQ ID NO 50
<211> LENGTH: 27
<212> TYPE: DNA
<213> ORGANISM: Bacillus subtilis

<400> SEQUENCE: 50
aaggatcttc atccttaaca tattttt                                27

<210> SEQ ID NO 51
<211> LENGTH: 42
<212> TYPE: DNA
<213> ORGANISM: Bacteriophage SP82

<400> SEQUENCE: 51
ggagccgctg agctaccaca gattgtgaaa ggagaggtta ac                42

<210> SEQ ID NO 52
<211> LENGTH: 19
<212> TYPE: DNA
<213> ORGANISM: Bacillus subtilis

<400> SEQUENCE: 52
aaaggaggaa ttcaaaatg                                         19

<210> SEQ ID NO 53
<211> LENGTH: 546
<212> TYPE: DNA
<213> ORGANISM: Bacillus thuringiensis

<400> SEQUENCE: 53
agcttaatta aagataatat ctttgaattg taacgcccct caaaagtaag aactacaaaa   60
aaagaatacg ttatatagaa atatgtttga accttcttca gattacaaat atattcggac  120
ggactctacc tcaaatgctt atctaactat agaatgacat acaagcacaa ccttgaaaat  180
ttgaaaatat aactaccaat gaacttgttc atgtgaatta tcgctgtatt taattttctc  240
aattcaatat ataatatgcc aatacattgt tacaagtaga aattaagaca cccttgatag  300
ccttactata cctaacatga tgtagtatta aatgaatatg taaatatatt tatgataaga  360
agcgacttat ttataatcat tacatatttt tctattggaa tgattaagat tccaatagaa  420
tagtgtataa attatttatc ttgaaaggag ggatgcctaa aaacgaagaa cattaaaaac  480
atatatttgc accgtctaat ggatttatga aaaatcattt tatcagtttg aaaattatgt  540
attatg                                                           546

<210> SEQ ID NO 54
```

<211> LENGTH: 42
<212> TYPE: DNA
<213> ORGANISM: Bacillus thuringiensis

<400> SEQUENCE: 54
ggagccgctg agctaccaca gattgtgaaa ggagaggtta ac 42

<210> SEQ ID NO 55
<211> LENGTH: 263
<212> TYPE: DNA
<213> ORGANISM: Bacillus subtilis

<400> SEQUENCE: 55
ataaggacaa atgaataaag attgtatcct tcggggcagg gtggaaatcc cgaccggcgg 60
tagtaaagca catttgcttt agagcccgtg acccgtgtgc ataagcacgc ggtggattca 120
gtttaagctg aagccgacag tgaaagtctg gatgggagaa ggatgatgag ccgctatgca 180
aaatgtttaa aaatgcatag tgttatttcc tattgcgtaa aatacctaaa gccccgaatt 240
ttttataaat tcggggcttt ttt 263

<210> SEQ ID NO 56
<211> LENGTH: 1545
<212> TYPE: DNA
<213> ORGANISM: Bacillus amyloliquefaciens

<400> SEQUENCE: 56
atgattcaaa aacgaaagcg gacagtttcg ttcagacttg tgcttatgtg cacgctgtta 60
tttgtcagtt tgccgattac aaaaacatca gccgtaaatg gcacgctgat gcagtatttt 120
gaatggtata cgccgaacga cggccagcat tggaaacgat tgcagaatga tgcggaacat 180
ttatcggata tcggaatcac tgccgtctgg attcctcccg catacaaagg attgagccaa 240
tccgataacg gatacggacc ttatgatttg tatgatttag gagaattcca gcaaaaaggg 300
acggtcagaa cgaaatacgg cacaaaatca gagcttcaag atgcgatcgg ctcactgcat 360
tcccggaacg tccaagtata cggagatgtg gttttgaatc ataaggctgg tgctgatgca 420
acagaagatg taactgccgt cgaagtcaat ccggccaata gaaatcagga aacttcggag 480
gaatatcaaa tcaaagcgtg gacggatttt cgttttccgg gccgtggaaa cacgtacagt 540
gattttaaat ggcattggta tcatttcgac ggagcggact gggatgaatc ccggaagatc 600
agccgcatct ttaagtttcg tggggaagga aaagcgtggg attgggaagt atcaagtgaa 660
aacggcaact atgactattt aatgtatgct gatgttgact acgaccaccc tgatgtcgtg 720
gcagagacaa aaaaatgggg tatctggtat gcgaatgaac tgtcattaga cggcttccgt 780
attgatgccg ccaaacatat taaattttca tttctgcgtg attgggttca ggcggtcaga 840
caggcgacgg gaaaagaaat gtttacggtt gcggagtatt ggcagaataa tgccgggaaa 900
ctcgaaaact acttgaataa aacaagcttt aatcaatccg tgtttgatgt tccgcttcat 960
ttcaatttac aggcggcttc ctcacaagga ggcggatatg atatgaggcg tttgctggac 1020
ggtaccgttg tgtccaggca tccggaaaag gcggttacat ttgttgaaaa tcatgacaca 1080
cagccgggac agtcattgga atcgacagtc caaacttggt ttaaaccgct tgcatacgcc 1140
tttattttga caagagaatc cggttatcct caggtgttct atggggatat gtacgggaca 1200
aaagggacat cgccaaagga aattccctca ctgaaagata atatagagcc gattttaaaa 1260
gcgcgtaagg agtacgcata cgggccccag cacgattata ttgaccaccc ggatgtgatc 1320
ggatggacga gggaaggtga cagctccgcc gccaaatcag gtttggccgc tttaatcacg 1380

```
gacggacccg gcggatcaaa gcggatgtat gccggcctga aaaatgccgg cgagacatgg   1440
tatgacataa cgggcaaccg ttcagatact gtaaaaatcg gatctgacgg ctggggagag   1500
tttcatgtaa acgatgggtc cgtctccatt tatgttcaga aataa                   1545
```

<210> SEQ ID NO 57
<211> LENGTH: 514
<212> TYPE: PRT
<213> ORGANISM: Bacillus amyloliquefaciens

<400> SEQUENCE: 57

```
Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Val
                20                  25                  30

Asn Gly Thr Leu Met Gln Tyr Phe Glu Trp Tyr Thr Pro Asn Asp Gly
            35                  40                  45

Gln His Trp Lys Arg Leu Gln Asn Asp Ala Glu His Leu Ser Asp Ile
        50                  55                  60

Gly Ile Thr Ala Val Trp Ile Pro Pro Ala Tyr Lys Gly Leu Ser Gln
65                  70                  75                  80

Ser Asp Asn Gly Tyr Gly Pro Tyr Asp Leu Tyr Asp Leu Gly Glu Phe
                85                  90                  95

Gln Gln Lys Gly Thr Val Arg Thr Lys Tyr Gly Thr Lys Ser Glu Leu
            100                 105                 110

Gln Asp Ala Ile Gly Ser Leu His Ser Arg Asn Val Gln Val Tyr Gly
        115                 120                 125

Asp Val Val Leu Asn His Lys Ala Gly Ala Asp Ala Thr Glu Asp Val
    130                 135                 140

Thr Ala Val Glu Val Asn Pro Ala Asn Arg Asn Gln Glu Thr Ser Glu
145                 150                 155                 160

Glu Tyr Gln Ile Lys Ala Trp Thr Asp Phe Arg Phe Pro Gly Arg Gly
                165                 170                 175

Asn Thr Tyr Ser Asp Phe Lys Trp His Trp Tyr His Phe Asp Gly Ala
            180                 185                 190

Asp Trp Asp Glu Ser Arg Lys Ile Ser Arg Ile Phe Lys Phe Arg Gly
        195                 200                 205

Glu Gly Lys Ala Trp Asp Trp Glu Val Ser Ser Glu Asn Gly Asn Tyr
    210                 215                 220

Asp Tyr Leu Met Tyr Ala Asp Val Asp Tyr Asp His Pro Asp Val Val
225                 230                 235                 240

Ala Glu Thr Lys Lys Trp Gly Ile Trp Tyr Ala Asn Glu Leu Ser Leu
                245                 250                 255

Asp Gly Phe Arg Ile Asp Ala Ala Lys His Ile Lys Phe Ser Phe Leu
            260                 265                 270

Arg Asp Trp Val Gln Ala Val Arg Gln Ala Thr Gly Lys Glu Met Phe
        275                 280                 285

Thr Val Ala Glu Tyr Trp Gln Asn Asn Ala Gly Lys Leu Glu Asn Tyr
    290                 295                 300

Leu Asn Lys Thr Ser Phe Asn Gln Ser Val Phe Asp Val Pro Leu His
305                 310                 315                 320

Phe Asn Leu Gln Ala Ala Ser Ser Gln Gly Gly Gly Tyr Asp Met Arg
                325                 330                 335

Arg Leu Leu Asp Gly Thr Val Val Ser Arg His Pro Glu Lys Ala Val
```

```
            340              345              350
Thr Phe Val Glu Asn His Asp Thr Gln Pro Gly Gln Ser Leu Glu Ser
            355              360              365
Thr Val Gln Thr Trp Phe Lys Pro Leu Ala Tyr Ala Phe Ile Leu Thr
            370              375              380
Arg Glu Ser Gly Tyr Pro Gln Val Phe Tyr Gly Asp Met Tyr Gly Thr
385              390              395              400
Lys Gly Thr Ser Pro Lys Glu Ile Pro Ser Leu Lys Asp Asn Ile Glu
                405              410              415
Pro Ile Leu Lys Ala Arg Lys Glu Tyr Ala Tyr Gly Pro Gln His Asp
                420              425              430
Tyr Ile Asp His Pro Asp Val Ile Gly Trp Thr Arg Glu Gly Asp Ser
                435              440              445
Ser Ala Ala Lys Ser Gly Leu Ala Ala Leu Ile Thr Asp Gly Pro Gly
                450              455              460
Gly Ser Lys Arg Met Tyr Ala Gly Leu Lys Asn Ala Gly Glu Thr Trp
465              470              475              480
Tyr Asp Ile Thr Gly Asn Arg Ser Asp Thr Val Lys Ile Gly Ser Asp
                485              490              495
Gly Trp Gly Glu Phe His Val Asn Asp Gly Ser Val Ser Ile Tyr Val
            500              505              510
Gln Lys
```

<210> SEQ ID NO 58
<211> LENGTH: 1539
<212> TYPE: DNA
<213> ORGANISM: Bacillus licheniformis

<400> SEQUENCE: 58

```
atgaaacaac aaaaacggct ttacgcccga ttgctgccgc tgttatttgc gctcatcttc    60
ttgctgcctc attctgcagc agcggcggca aatcttaaag gacgctgat gcagtatttt   120
gaatggtaca tgcccaatga cggccaacat tggaagcgct tgcaaaacga ctcggcatat   180
ttggctgaac acggtattac tgccgtctgg attcccccgg catataaggg aacgagccaa   240
gcggatgtgg gctacggtgc ttacgacctt tatgatttag gggagtttca tcaaaaaggg   300
acggttcgga caaagtacgg cacaaaagga gagctgcaat ctgcgatcaa aagtcttcat   360
tcccgcgaca ttaacgtttta cggggatgtg gtcatcaacc acaaaggcgg cgctgatgcg   420
accgaagatg taaccgcggt tgaagtcgat cccgctgacc gcaaccgcgt aatttcagga   480
gaacaccgaa ttaaagcctg gacacatttt catttccgg ggcgcggcag cacatacagc   540
gattttaaat ggcattggta ccattttgac ggaaccgatt gggacgagtc ccgaaagctg   600
aaccgcatct ataagtttca aggaaaggct tgggattggg aagtttccaa tgaaaacggc   660
aactatgatt atttgatgta tgccgacatc gattatgacc atcctgatgt cgcagcagaa   720
attaagagat ggggcacttg gtatgccaat gaactgcaat ggacgggttt ccgtcttgat   780
gctgtcaaac acattaaatt ttctttttttg cgggattggg ttaatcatgt cagggaaaaa   840
acggggaagg aaatgtttac ggtagctgaa tattggcaga tgacttgggg cgcgctggaa   900
aactatttga caaaacaaa ttttaatcat tcagtgtttg acgtgccgct tcattatcag   960
ttccatgctg catcgacaca gggaggcggc tatgatatga ggaaattgct gaacggtacg  1020
gtcgtttcca agcatccgtt gaaagcggtt acatttgtcg ataaccatga tacacagccg  1080
ggcaatcgc ttgagtcgac tgtccaaaca tggtttaagc cgcttgctta cgcttttatt  1140
```

```
ctcacaaggg aatctggata ccctcaggtt ttctacgggg atatgtacgg gacgaaagga   1200
gactcccagc gcgaaattcc tgccttgaaa cacaaaattg aaccgatctt aaaagcgaga   1260
aaacagtatg cgtacggagc acagcatgat tatttcgacc accatgacat tgtcggctgg   1320
acaagggaag cgacagctc ggttgcaaat tcaggtttgg cggcattaat aacagacgga   1380
cccggtgggg caaagcgaat gtatgtcggc cggcaaaacg ccggtgagac atggcatgac   1440
attaccggaa accgttcgga gccggttgtc atcaattcgg aaggctgggg agagtttcac   1500
gtaaacggcg ggtcggtttc aatttatgtt caaagatag                          1539
```

<210> SEQ ID NO 59
<211> LENGTH: 512
<212> TYPE: PRT
<213> ORGANISM: Bacillus licheniformis

<400> SEQUENCE: 59

Met Lys Gln Gln Lys Arg Leu Tyr Ala Arg Leu Leu Pro Leu Leu Phe
1               5                   10                  15

Ala Leu Ile Phe Leu Leu Pro His Ser Ala Ala Ala Ala Asn Leu
            20                  25                  30

Lys Gly Thr Leu Met Gln Tyr Phe Glu Trp Tyr Met Pro Asn Asp Gly
        35                  40                  45

Gln His Trp Lys Arg Leu Gln Asn Asp Ser Ala Tyr Leu Ala Glu His
    50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Arg Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Asn Glu Asn Gly Asn Tyr Asp Tyr
    210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
    290                 295                 300

-continued

```
Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ala Val Thr Phe
            340                 345                 350

Val Asp Asn His Asp Thr Gln Pro Gly Gln Ser Leu Glu Ser Thr Val
        355                 360                 365

Gln Thr Trp Phe Lys Pro Leu Ala Tyr Ala Phe Ile Leu Thr Arg Glu
    370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
        435                 440                 445

Ala Asn Ser Gly Leu Ala Ala Leu Ile Thr Asp Gly Pro Gly Gly Ala
    450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510
```